(12) United States Patent
Narbad et al.

(10) Patent No.: US 6,664,088 B2
(45) Date of Patent: Dec. 16, 2003

(54) PRODUCTION OF VANILLIN

(75) Inventors: Arjan Narbad, Norfolk (GB); Michael John Charles Rhodes, Norfolk (GB); Michael John Gasson, Norfolk (GB); Nicholas John Walton, Norfolk (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/733,383

(22) Filed: Dec. 7, 2000

(65) Prior Publication Data

US 2001/0014467 A1 Aug. 16, 2001

Related U.S. Application Data

(62) Division of application No. 09/155,183, filed as application No. PCT/GB97/00809 on Mar. 24, 1997, now Pat. No. 6,323,011.

(30) Foreign Application Priority Data

Mar. 23, 1996 (GB) .............................. 9606187

(51) Int. Cl.$^7$ ........................... C12N 9/14; C12N 9/00; C12N 9/15; C12N 1/20; C07H 21/04

(52) U.S. Cl. ....................... 435/195; 435/183; 435/195; 435/219; 435/232; 435/147; 435/874; 435/252.3; 435/320.1; 435/278; 435/295; 536/23.2

(58) Field of Search ................................ 435/183, 195, 435/219, 232, 147, 252.3, 320.1, 278, 295, 874; 536/23.2

(56) References Cited

U.S. PATENT DOCUMENTS

| | | | |
|---|---|---|---|
| 5,128,253 A | 7/1992 | Labuda et al. | 435/147 |
| 5,262,315 A | 11/1993 | Gross et al. | 435/147 |
| 5,279,950 A | 1/1994 | Labuda et al. | 435/147 |
| 5,510,252 A | 4/1996 | Hopp et al. | 435/146 |
| 5,610,041 A | * 3/1997 | Somerville et al. | 800/264 |

FOREIGN PATENT DOCUMENTS

| | | |
|---|---|---|
| DE | 3604874 A1 | 2/1986 |
| DE | 3604874 A | 8/1987 |
| EP | 0 405 197 A1 | 6/1990 |
| EP | 0 405 197 A1 | 1/1991 |
| EP | 0 845 532 A2 | 6/1998 |
| JP | 2195871 | 8/1990 |
| JP | 2200192 | 8/1990 |
| JP | 5227980 | 9/1993 |
| JP | 678765 | 3/1994 |
| WO | WO 93/14214 | 7/1993 |
| WO | WO 93/21338 | 10/1993 |
| WO | WO 93/25088 | 12/1993 |
| WO | WO 94/01564 | 1/1994 |
| WO | WO 94/02621 | 2/1994 |
| WO | WO 94/06925 | 3/1994 |
| WO | WO 94/13614 | 6/1994 |

OTHER PUBLICATIONS

Zenk et al., "Procedure for the Enzymatic Synthesis and Isolation of Cinnamoyl–CoA Thiolesters Using a Bacterial System," *Anal. Biochem.*, 101:182–187 (1980).

Toms et al., "The Degradation of trans–Ferulic Acid by *Pseudomonas acidovorans*," *Biochem.*, 9:337–343 (1970).

Huang et al., "Mechanisms of Ferulic Acid Conversions to Vanillic Acid and Guaiacol by *Rhodotorula rubra*," *J. Biol. Chem.*, 268(32):23954–23958 (1993).

Baré et al., "Bioconversion of Vanillin into Vanillic Acid by *Pseudomonas fluorescens* Strain BTP9," *Appl. Biochem. Biotech.*, 45/46:599–610 (1994).

Huang et al., "Microbial Transformations of Ferulic Acid by *Saccharomyces cerevisiae* and *Pseudomonas fluorescens*," *Appl. Environ. Microbiol.*, 59(7):2244–2250 (1993).

Zenk, "Biosynthesis von Vanillin in *Vanilla planifolia* Andr.," *Z. Pflanzenphysiol. Bd.*, 53:404–414 (1965).

Rhodes et al., "Reduction of the CoA Thioesters of ρ–Coumaric and Ferulic Acids by Extracts of Aged *Brassica Napo–Brassica* Root Tissue," *Phytochem.*, 13:107–110 (1974).

Rosazza et al., "Review: Biocatalytic Transformations of Ferulic Acid: An Abundant Aromatic Natural Product," *J. Indust. Microbiol.*, 15:457–471 (1995).

Hagedorn et al., "Microbial Biocatalysis in the Generation of Flavor and Fragrance Chemicals," *Annu. Rev. Microbiol.*, 48:773–800 (1994).

Andreoni et al., "Ferulic Acid Degradation Encoded by a Catabolic Plasmid," *FEMS Microbiol. Ecol.*, 53:129–132 (1988).

Funk et al., "Phenylpropanoid Metabolism in Suspension Cultures of *Vanilla planifolia* Andr. II. Effects of Precursor Feeding and Metabolic Inhibitors," *Plant Physiol.*, 94:95–101 (1990).

Funk et al., "Phenylpropanoid Metabolism in Suspension Cultures of *Vanilla planifolia* Andr. IV. Induction of Vanillic Acid Formation," *Plant Physiol.*, 99:256–262 (1992).

Löscher et al., "Biosynthesis of ρ–Hydroxybenzoate from ρ–Coumarate and ρ–Coumaroyl–Coenzyme A in Cell–Free Extracts Of *Lithospermum erythrorhizon* Cell Cultures," *Plant Physiol.*, 106:271–279 (1994).

(List continued on next page.)

*Primary Examiner*—Tekchand Saidha
(74) *Attorney, Agent, or Firm*—Nixon Peabody LLP

(57) ABSTRACT

A method of producing vanillin comprising the steps of: (1) providing trans-ferulic acid or a salt thereof; and (2) providing trans-ferulate: CoASH ligase activity (enzyme activity I), trans-feruloyl ScoA hydratase activity (enzyme activity II), and 4-hydroxy-3-methoxyphenyl-β-hydroxypropionyl SCoA (HMPHP SCoA) cleavage activity (enzyme activity III). Conveniently the enzymes are provided by *Pseudomonas fluorescens* Fe3 or a mutant or derivative thereof. Polypeptides with enzymes activities II and III and polynucleotides encoding the polypeptides. Use of the polypeptides or the polynucleotides in a method for producing vanillin is also provided.

16 Claims, 27 Drawing Sheets

OTHER PUBLICATIONS

Omori et al., "Protocatechuic Acid Production from *Trans*-ferulic Acid by *Pseudomonas* sp. HF–1 Mutants Defective on Protocatechuic Acid Catabolism," *Appl. Microbiol. Biotechnol.*, 29:497–500 (1988).

Cain, "The Uptake and Catabolism of Lignin–Related Aromatic Compounds and Their Regulation in Microorganisms," in Kirk, eds., *Lignin Biodegradation*, Boca Raton, FL.:CRC Press, pp. 21–60 (1980).

Hall et al., "Enzymatic Transformations of Lignin," in Kirk, eds., *Lignin Biodegradation*, Boca Raton, FL.:CRC Press, pp. 33–49 (1980).

Kawakami, "Degradation of Lignin–Related Aromatics and Lignins by Several Pseudomonads," in Kirk, eds., *Lignin Biodegradation*, Boca Raton, FL.:CRC Press, pp. 103–125 (1980).

Gibson et al. "Microbial Degradation of Aromatic Hydrocarbons," in Gibson, ed., *Microbial Degradation of Organic Compounds*, New York, New York:Marcel Dekker, pp. 181–251 (1984).

Bayly et al., "The Degradation of Aromatic Compounds by the Meta and Gentisate Pathways," in Gibson, ed., *Microbial Degradation of Organic Compounds*, New York, New York: Marcel Dekker, pp. 253–294 (1984).

Reinke, "Microbial Degradation of Halogenated Aromatic Compounds," in Gibson, ed., *Microbial Degradation of Organic Compounds*, New York, New York:Marcel Dekker, pp. 319–359 (1984).

Safe, "Microbial Degradation of Polychlorinated Biphenyls," in Gibson, ed., *Microbial Degradation of Organic Compounds*, New York, New York:Marcel Dekker, pp. 361–369 (1984).

Ribbons et al., "Microbial Degradation of Phthalates," in Gibson, ed., *Microbial Degradation of Organic Compounds*, New York, New York:Marcel Dekker, pp. 371–397 (1984).

Kirk, "Degradation of Lignin," in Gibson, ed., *Microbial Degradation of Organic Compounds*, New York, New York: Marcel Dekker, pp. 399–437 (1984).

Ramos et al., "Redesigning Metabolic Routes: Manipulation of TOL Plasmid Pathway for Catabolism of Alkylbenzoates," *Science*, 235:593–596 (1987).

Romero–Steiner et al., "Characterization of the *pcaR* Regulatory Gene from *Pseudomonas putida*, Which is Required for the Complete Degradation of ρ–Hydroxybenzoate," *J. Bacteriol.*, 176:5771–5779 (1994).

Inoue et al., "Overlapping Substrate Specificities of Benzaldehyde Dehydrogenase (the xylC Gene Product) and 2–Hydroxymuconic Semialdehyde Dehydrogenase (the xylG Gene Product) Encoded by TOL Plasmid pWW0 of *Pseudomonas putida*," *J. Bacteriol.*, 177:1196–1201 (1995).

Casey et al., "Microbial Routes to Aromatic Aldehydes," *Enzyme Microbiol. Technol.*, 14:739–747 (1992).

Christov et al., "Esterases of Xylan–Degrading Microorganisms: Production, Properties, and Significance," *Enzyme Microbiol. Technol.*, 15:460–475 (1993).

Faulds et al., "Release of Ferulic Acid from Wheat Bran by a Ferulic Acid Esterase (FAE–III) from *Aspergillus niger*," *Appl. Microbiol. Biotechnol.*, 43:1082–1087 (1995).

Faulds et al., "Release of Ferulic Acid from Maize Bran and Derived Oligosaccharides by *Aspergillus niger* Esterases," *Carbohydrate Polymers* 27:187–190 (1995).

Faulds et al., "The Purification and Characterization of 4–Hydroxy–3–Methoxycinnamic (Ferulic) Acid Esterase from *Streptomyces olivochromogenes*," *J. Gen. Mcrobiol.*, 137:2339–2345 (1991).

Castanares et al., "Purification and Properties of a Feruloyl/ρ–Coumaroyl Esterase from the Fungus *Penicillium phiophilum*," *Enzyme Microb. Technol.*, 14:875–884 (1992).

Borneman et al., "Feruloyl and ρ–Coumaroyl Esterase from Anaerobic Fungi in Relation to Plant Cell Wall Degradation," *Appl. Microbiol. Biotechnol.*, 33:345–351 (1990).

MacKenzie et al., "Ferulic Acid Esterase Activity from *Schizophyllum commune*," *Appl. Enviorn. Microbiol.*, 54:1170–1173 (1988).

Tenkanen et al., "Production, Purification and Characterization of an Esterase Liberating Phenolic Acids from Lignocellulosics," *J. Biotechnol.*, 18:69–84 (1991).

Faulds et al., "Purification and Characterization of a Ferulic Acid Esterase (FAE–III) from *Aspergillus niger:* Specificity for The Phenolic Moiety and Binding to Microcrystalline Cellulose," *Microbiol.*, 140:779–787 (1994).

Ferreira et al., "A Modular Esterase from *Pseudomonas fluorescens* Subsp. Cellulosa Containing a Non–Catalytic Cellulose–Binding Domain," *Biochem. J.*, 294:349–355 (1993).

Hazelwood et al., "The Molecular Architecture of Xylanases from *Psuedomonas fluorescens* Subsp. Cellulosa," in Visser, eds., *Xylans and Xylanases*, Amsterdam:Elsevier, pp. 259–273 (1992).

Perestelo et al., "Production of Vanillic Acid from Vanillin by Resting Cells of *Serratia marcescens*," *Appl. Environ. Microbiol.*, 55:1660–1662 (1989).

Pometto III et al., "Whole–Cell Bioconversion of Vanillin to Vanillic Acid by *Stretomyces viridosporus*," *Appl. Environ. Microbiol.*, 45:1582–1585 (1983).

Bengtson et al., "Extraction of Bioproducts with Homogeneous Membranes," in Étiévant, eds., *Bioflavour 95*, Paris, France:INRA, pp. 393–403 (1995).

Zhang et al., "Pervaporation Membranes," *Separ. Sci. Technol.*, 30:1–31 (1995).

Rajagopalan et al., "Pervaproation of Grape Juice Aroma," *J. Membrane Sci.*, 104:243–250 (1995).

Boyadzhiev et al., "Extraction of Phenylalanine from Dilute Solutions by Rotating Film Pertraction," *Process Biochem.*, 29:237–243 (1994).

Yazaki et al., "Formation of ρ–Hydroxybenzoic Acid from ρ–Coumaric Acid by cell Free Extract of *Lithospermum erythrorhizon* Cell Cultures," *Phytochemistry*, 30:2233–2236 (1991).

Leffemberg et al., "Enzymatic Preparations of Coniferaldehyde from Coniferyl Benzoate ex. Siam Benzoin," *Appl. Biochem. Biotechnol.*, 37:43–52 (1992)

Yamanaka et al., "A New Dye–Linked Alcohol Dehydrogenase (Vanillyl Alcohol Dehydrogenase) from *Rhodopseudomonas acidophila* M402 Purification, Identification of reaction Product and Substrate Specificity," *Agric. Biol. Chem.*, 47:2173–2183 (1983).

Yamanaka et al., "Occurence of Dehydrogenases for the Metabolism of Vanillyl Alcohol in *Rhodospeudomonas acidophila* M402," *Agric. Biol. Chem.*, 47:1361–1362 (1983).

Sparnins et al., "Catabolism of L–Tyrosine in *Trichosporon cutaneum*," *J. Bacteriol.*, 138(2):425–430 (1979).

Gasson et al., "Metabolism of Ferulic Acid to Vanillin," *J. Biol. Chem.* 273(13):4163–4170 (1998).

Lute, "The Pathway of Phenylpropanoid Degradation in *Pseudomonas putida* mt–2," (Ph.D. Thesis) The University of Michigan, University Microfilms International, No. 8621334 (1986).

Derwent Abstract No. 94–07039 for WO 9406925, "Production of Glyoxylic Acid by Oxidizing Glycolic Acid in the Prescence of Immobilized Glycolate–Oxidase and Catalase," (1994).

Derwent Abstract No. 94–04068 for WO 9402621, "Aroma and/or Flavor Production Using a Lipoxygenase," (1994).

Derwent Abstract No. 94–03513 for U.S. Patent No. 5,279,950, "Vanillin Production from a Vanilla Fragrans, Vanilla Phaentha, Vanila Pompona and Vanilla Tahetensis Call Culture Containing Ferulic Acid," (1994).

Derwent Abstract No. 94–03418 for WO 9401564, "Jerusalem Artichoke of *Arabidopsis thaliana* Cytochrome–P450 and NADPH Cytochrome–P450–Reductase Expression in *Saccharomyces cerevisiae*," (1994).

Derwent Abstract No. 94–02808 for WO 9325088, "High Yield Vanilla Flavor Production from Vanilla Pod," (1994).

Derwent Abstract No. 94–00236 for WO 9314214, "Isolating Microorganisms Which Produce Taxane Compounds, Particularly Taxol," (1994).

Derwent Abstract No. 93–08187, Leffemberg et al., "Enzymatic Preparation of Coniferaldehyde from Coniferyl Benzoate ex. Sian Benzion," *Appl. Biochem. Biotechnol.* 37(1):43–52 (1992).

Derwent Abstract No. 92–00354 for J02200192, "Vanilla Production by Culture of Pycnoporus sp.," (1992).

Derwent Abstract No. 90–14831 for J02195871, "Novel Pseudomonas sp. and Dioxygenase Enzyme," (1990).

Derwent Abstract No. 87–12443, "Coniferylaldehyde Preparation," (1987).

* cited by examiner

| | |
|---|---|
| 97.4 kDa | Phosphorylase b |
| 66.2 kDa | Bovine serum albumin |
| 45.5 kDa | Hen egg white ovalbumin |
| 31.0 kDa | Bovine carbonic anhydrase |
| 21.5 kDa | Soybean trypsin inhibitor |
| 14.4 kDa | Hen egg white lysozyme |

Redundant primers designed from 20 N-terminal amino acid sequence

```
  1   2   3   4   5   6   7   8   9  10  11  12  13  14  15  16  17  18  19  20
 Ser Thr Tyr Glu Gly Arg Trp Lys Thr Val Lys Val Glu Ile Gln Asp Gly Ile Ala Phe
 TCC ACG TAC GAG GGC CGC TGG AAG ACG GTC AAG GTC GAG ATC CAG GAC GGC ATC GCG TTT
 GG   C   T   A   T   G   A        A   C   G   A   A   T   A   T   T   C   C
                                                                              C
         └──────────── Primer P66 ────────────┘         └──────── Primer P67 ────────┘
```

Figure 10

Nucleotide and amino acid sequence of the cleavage enzyme and vanillin dehydrogenase.
Sequence determined from sub-cloned fragments pFI989 and pFI1056 and from the cosmid
clone pFI794

| | | |
|---:|:---|---:|
| 1 | GAATTCTCTCGCGCTTTGCCCAGTCCTACCCGCTGGTGCAGATCGAGGTG | 50 |
| 51 | CATTGCGAGTCGTCCAAGCAACTTCTCTTGCGCCAGGACCTCGACCTGTC | 100 |
| 101 | CATCGTGACCCGCGAACCCGGCAACGAAATCGGCCAGCTGTTGCGCAAGG | 150 |
| 151 | AGCGTTTTGTCTGGGCCCAGGCCCAGTGCTACAACCCTGTCGAGCAATCA | 200 |
| 201 | CCCTTGCCGCTGGCGATGTTCAACAGTGACTGCTTCTGCCGTCTTTGGGC | 250 |
| 251 | CTGTAATGCGCTGGATGCCGCCGGACGTGAATACCGCATCGCCTACAACA | 300 |
| 301 | GTTCGAGCCTGTCGGCGCTGATGGCAGTGGTCAGCGCCGGGCTGGCGGTG | 350 |
| 351 | ACCGCTCAATTGGAAAGCCTGATCCCGCAGGACATGCGCATCCTCGGCGA | 400 |
| 401 | GGCCGAAGGCCTGCCCCAACTGCCCGAGGCGAGCATCATGCTGCTGCGCA | 450 |
| 451 | ATCTGCATAATCCGTCGCCGATTACCGAATGTCTGGCGGAGCACATCGTC | 500 |
| 501 | GAAGGCTTCAAACTTTAAAGGCGAGCATCACCGCGCAGAGCACCAGAAAA | 550 |
| 551 | CCGCAGAACAAACCGCGTAGTAGCCGCTCCGGCAGGGCGTGGGCAATCTT | 600 |
| 601 | CACGCCCCAACTGATACTGAGCAGACCGCCCACCGCCATGGGCAACGCGA | 650 |
| 651 | TGTGCCAGTCGACTTGCTGGTGCAGGGCGTAGGTCGCCAGGGTTACACCG | 700 |
| 701 | GTGCTGGGTAAAGCCAGTGCCAACGACAGGCCCTGGGCCACCACCTGGGT | 750 |
| 751 | GGTGCCAAACAAGCTGGTCAATACCGGCGTTGCGACCACAGCGCCGCCCA | 800 |
| 801 | CCCCGAACAAGCCACCCATGACGCCGGACGCCGCGCCCAGCACCCCGAGC | 850 |
| 851 | CAGGGCCACGAATAGCGCATCTGCGCAGTCGGTGCCGCCGCAGTCATGAA | 900 |
| 901 | CATGCGCATCAGGTTGTAGACCGACAAGGCCACCAGAAACACCACGAACC | 950 |
| 951 | CGATGCGCATCACCTGAGCGTCGATCCCCACCGCCCAGATCGAACCGAGC | 1000 |
| 1001 | CAGGCAAAGCAGAACCCCATGGAGGCCAACGGCAGCGCGTGGCGCAACTC | 1050 |
| 1051 | GATGCGATTACGTTGGTGATAACGCCATAACGCCAGCATCACGTTCGGCA | 1100 |
| 1101 | CCACCATGACCAGAGCTGTGCCCTGGGCAAGCTGCTGATCCAGGCCAAAT | 1150 |
| 1151 | AACACGCCCAGAGCGGGAATGGCGATCAAGCCACCGCCGATTCCAAACAA | 1200 |
| 1201 | ACCACCTACGGTCCCCAAGGCTGCACCGAGCAGCAGGTACATCGTCAACT | 1250 |
| 1251 | CAATCACAGGTCAAATTCCCTCACGTCAATGGGTGCATCCTACGCAGTCG | 1300 |

Figure 12A

| 1301 | GGGCTAGCGGGGAAACGCACAGCAACGCACAATGGCTATGCCAAATTCGC | 1350 |
| 1351 | ACAAGCAATCCTCCATGAACCCCACAACGCTCACCGATCAATTGGGTCTA | 1400 |
| 1401 | TTCCTTGATGTCGTGGAAACCGGCAGTTTTTCCGCTGCGTCCCGACGCCA | 1450 |
| 1451 | TCCGCTGACACCCTCCGCCGTCGCCAGGCGTATCGATAGTCTGGAACAGG | 1500 |
| 1501 | CGCTCGACAGCCAATTGTTCGTGCGCACCACTCATGCTGTGCGTCCTACG | 1550 |
| 1551 | CCAGCGGGATTGGCGTTTGCCGAGCGAGCCCGACGCATTGTCGGCGAGTT | 1600 |
| 1601 | GCGCCTGGCGCGGGCCGAGGTCGCCTCCCTGAGCAGCGCGCCTGAAGGAC | 1650 |
| 1651 | TGATTCGGGTCGACGCCCCCGCAGCCTTCGGCCGCAGGCACCTGGCGCCG | 1700 |
| 1701 | GTGATCTATGACTACGACTTCGCCGCCTCCGGCGTGCCCGGGCTGCGGGG | 1750 |
| 1751 | CCGGTTGCGCTACCTGCGCGGCGACAACATCGAGTTGAAAGCCTTCAACG | 1800 |
| 1801 | CCGAAGACCGCAAGGAGCGCGAGTTCCAGATGGAGCTGGGCTACGTGGTG | 1850 |
| 1851 | CAAAGCGGTCCGCTGAAAAACGTCGGCCTGGTGGCGCGCAAGGCAATCTA | 1900 |
| 1901 | CCGCAATGACTTCCCCACTGGCGCCGCCTTCCGCGATGAAAACCAGACGC | 1950 |
| 1951 | GGTTTCTGGTGACCTATACCTTGCCGATCTGGTGAGTGCGCGTGTTGCGG | 2000 |
| 2001 | TGGGGCTGATGGCCCCATCGCGAGCGGGCTCGCTCCTACAGTGGGTTTGG | 2050 |
| 2051 | TGTTAATCACAGAGGCTGTGGAGCTTGCAGCCCCTGTAGGCGCTGGCTTG | 2100 |
| 2101 | CCAGCGAGGCGTAGGCACTGCTGGCGCAAGGCTCAAGGCCCCACAGGCCC | 2150 |
| 2151 | GCTCCCACCCTTCAGATTTTCTATTCCTGATAAATCTTCTTCAGCAGCCG | 2200 |
| 2201 | CAGCAGCTCGTCGCGTTCCTGGTCGTCCAGTGCCGAGGTGGCGTCGAGGT | 2250 |
| 2251 | CGCTTTGGGCGGCGATCTGGTTCAGTTCCTTGAGCAGGGTCTCGCCGGTC | 2300 |
| 2301 | TTGCTGAGGAATATCCCGTACGAGCGCTTGTCCGGCTTGCAGCGCACACG | 2350 |
| 2351 | CACCGCCAGCGCCCGGCTTTCCAGCTTATTCAGCAGCGGTACCACCTGGG | 2400 |
| 2401 | GCGGCTCGATGCTCAGAGCCCGGGCCAGGTCGGCCTGCATCAGGCCGGGG | 2450 |
| 2451 | TTCTGATTGATGATCGCCAGCGCCGAGAATTGCGCGGGGCGCAGATCGTG | 2500 |
| 2501 | GGCCGAGAGGCGGCTGATCAGGTTCTGGAACAGTTTCAGTTGCGCACGGC | 2550 |
| 2551 | GCATGGCGTAGCCGATCAGATCATTCAGCGCCGAATCCATGGGCGCCTGG | 2600 |
| 2601 | GTCTCGGCGGGAGTCGACGCAGCCTCGACCGACTCGGCGAGGGGGAGGG | 2650 |
| 2651 | CTTGGCCATTGCGGGGAAGTCCTGAAGATGGAGGTTAACAAGACTATCTA | 2700 |
| 2701 | GTTTGCCGACCTTGGCCGGTGATTGCTACGGCCAATATCGCTCGGCGCCA | 2750 |

Figure 12B

```
2751  AGACCGACCAGTCCATCACCTGCGAGAAAATTGGTTAAATCAATTAATAG  2800

2801  TTAATTGACATAACTAATTCGCTGCTTTAATTTCGAGTCATCTTCAAAAC  2850

2851  CCAGAACAAGAGAGCATCGCCATGAGCACATACGAAGGTCGCTGGAAAAC  2900
                        MetSerThrTyrGluGlyArgTrpLysTh

2901  GGTCAAGGTCGAAATCGAAGACGGCATCGCGTTTGTCATCCTCAATCGCC  2950
      rValLysValGluIleGluAspGlyIleAlaPheValIleLeuAsnArgP

2951  CGGAAAAACGCAACGCGATGAGCCCGACCCTGAACCGCGAGATGATCGAT  3000
      roGluLysArgAsnAlaMetSerProThrLeuAsnArgGluMetIleAsp

3001  GTTCTGGAAACCCTCGAGCAGGACCCTGCCGCCGGTGTGCTGGTGCTGAC  3050
      ValLeuGluThrLeuGluGlnAspProAlaAlaGlyValLeuValLeuTh

3051  CGGTGCGGGCGAAGCCTGGACCGCAGGCATGGACCTCAAGGAATACTTCC  3100
      rGlyAlaGlyGluAlaTrpThrAlaGlyMetAspLeuLysGluTyrPheA

3101  GCGAAGTGGACGCCGGCCCGGAAATCCTCCAGGAAAAAATCCGCCGCGAA  3150
      rgGluValAspAlaGlyProGluIleLeuGlnGluLysIleArgArgGlu

3151  GCCTCGCAATGGCAATGGAAACTGCTGCGCATGTACGCCAAGCCGACCAT  3200
      AlaSerGlnTrpGlnTrpLysLeuLeuArgMetTyrAlaLysProThrIl

3201  CGCCATGGTCAATGGCTGGTGCTTCGGCGGCGGTTTCAGCCCGCTGGTGG  3250
      eAlaMetValAsnGlyTrpCysPheGlyGlyGlyPheSerProLeuValA

3251  CCTGCGACCTGGCGATCTGCGCCGACGAAGCAACCTTCGGTCTCTCGGAA  3300
      laCysAspLeuAlaIleCysAlaAspGluAlaThrPheGlyLeuSerGlu

3301  ATCAACTGGGGTATCCCGCCGGGCAACCTGGTGAGCAAGGCCATGGCCGA  3350
      IleAsnTrpGlyIleProProGlyAsnLeuValSerLysAlaMetAlaAs

3351  CACCGTGGGCCACCGCCAGTCGCTCTACTACATCATGACCGGCAAGACCT  3400
      pThrValGlyHisArgGlnSerLeuTyrTyrIleMetThrGlyLysThrP

3401  TCGGTGGGCAGAAAGCCGCCGAGATGGGCCTGGTCAACGAAAGCGTGCCC  3450
      heGlyGlyGlnLysAlaAlaGluMetGlyLeuValAsnGluSerValPro

3451  CTGGCGCAACTGCGCGAAGTCACCATCGAGCTGGCGCGTAACCTGCTCGA  3500
      LeuAlaGlnLeuArgGluValThrIleGluLeuAlaArgAsnLeuLeuGl

3501  AAAAAACCCGGTGGTGCTGCGTGCCGCCAAACACGGTTTCAAACGCTGCC  3550
      uLysAsnProValValLeuArgAlaAlaLysHisGlyPheLysArgCysA

3551  GCGAACTGACCTGGGAGCAGAACGAGGATTACCTGTACGCCAAGCTCGAT  3600
      rgGluLeuThrTrpGluGlnAsnGluAspTyrLeuTyrAlaLysLeuAsp

3601  CAGTCGCGTTTGCTGGACACCGAAGGCGGTCGCGAGCAGGGCATGAAGCA  3650
      GlnSerArgLeuLeuAspThrGluGlyGlyArgGluGlnGlyMetLysGl

3651  ATTCCTCGACGACAAGAGCATCAAGCCTGGCCTGCAAGCGTATAAACGCT  3700
      nPheLeuAspAspLysSerIleLysProGlyLeuGlnAlaTyrLysArgE

3701  GAAGGACGACGCTGCGGGCGCATTGCGCGAAGGCGAGTGCGCCCTGAAGC  3750
      nd
```

Figure 12C

| | | |
|---|---|---|
| 3751 | TGCGTTTACATCACTGCTAAGCATTCCGATAAAGACGATAAAGAGGAATC | 3800 |
| 3801 | ACCATGCTGGACGTGCCCCTGCTGATTGGCGGCCAGTCGTGCCCCGCGCG<br>     MetLeuAspValProLeuLeuIleGlyGlyGlnSerCysProAlaAr | 3850 |
| 3851 | CGACGGTCGAACCTTCGAGCGCCGCAACCCGGTGACTGGCGAGTTGGTGT<br>gAspGlyArgThrPheGluArgArgAsnProValThrGlyGluLeuValS | 3900 |
| 3901 | CGCGGGTTGCCGCCGCCACCCTGGAAGATGCCGACGCCGCCGTGGCCGCT<br>erArgValAlaAlaAlaThrLeuGluAspAlaAspAlaAlaValAlaAla | 3950 |
| 3951 | GCCCAGCAAGCGTTTCCCGCGTGGGCCGCGCTGGCGCCCAATGAACGGCG<br>AlaGlnGlnAlaPheProAlaTrpAlaAlaLeuAlaProAsnGluArgAr | 4000 |
| 4001 | CAGCCGTTTGCTCAAGGCCGCCGAACAATTGCAGGCGCGCAGCGGCGAGT<br>gSerArgLeuLeuLysAlaAlaGluGlnLeuGlnAlaArgSerGlyGluP | 4050 |
| 4051 | TCATCGAGGCGGCGGGCGAGACCGGCGCCATGGCCAACTGGTACGGGTTC<br>heIleGluAlaAlaGlyGluThrGlyAlaMetAlaAsnTrpTyrGlyPhe | 4100 |
| 4101 | AACGTACGGCTGGCGGCCAACATGCTGCGTGAAGCGGCATCGATGACCAC<br>AsnValArgLeuAlaAlaAsnMetLeuArgGluAlaAlaSerMetThrTh | 4150 |
| 4151 | CCAGGTCAATGGTGAAGTGATTCCCTCGGACGTTCCCGGCAGTTTCGCCA<br>rGlnValAsnGlyGluValIleProSerAspValProGlySerPheAlaM | 4200 |
| 4201 | TGGCCCTGCGCCAGCCCTGTGGCGTGGTGCTGGGCATCGCCCCCTGGAAC<br>etAlaLeuArgGlnProCysGlyValValLeuGlyIleAlaProTrpAsn | 4250 |
| 4251 | GCCCCGGTGATTCTCGCCACCCGGGCGATTGCCATGCCGCTGGCCTGTGG<br>AlaProValIleLeuAlaThrArgAlaIleAlaMetProLeuAlaCysGl | 4300 |
| 4301 | CAACACCGTGGTGCTGAAGGCTTCCGAGCTGAGTCCGGCGGTGCATCGCT<br>yAsnThrValValLeuLysAlaSerGluLeuSerProAlaValHisArgL | 4350 |
| 4351 | TGATCGGCCAGGTGCTGCAGGACGCCGGCCTGGGCGATGGCGTGGTCAAC<br>euIleGlyGlnValLeuGlnAspAlaGlyLeuGlyAspGlyValValAsn | 4400 |
| 4401 | GTCATCAGTAATGCGCCGGCGGATGCGGCACAGATTGTCGAGCGCCTGAT<br>ValIleSerAsnAlaProAlaAspAlaAlaGlnIleValGluArgLeuIl | 4450 |
| 4451 | TGCCAACCCGGCCGTACGCCGGGTCAATTTCACCGGTTCGACCCACGTCG<br>eAlaAsnProAlaValArgArgValAsnPheThrGlySerThrHisValG | 4500 |
| 4501 | GGCGCATTGTCGGCGAGCTCTCGGCGCGCCACCTCAAACCGGCGTTGCTC<br>lyArgIleValGlyGluLeuSerAlaArgHisLeuLysProAlaLeuLeu | 4550 |
| 4551 | GAGCTGGGCGGCAAGGCACCGTTGCTGGTGCTCGACGATGCCGACCTGGA<br>GluLeuGlyGlyLysAlaProLeuLeuValLeuAspAspAlaAspLeuGl | 4600 |
| 4601 | GGCTGCCGTGCAGGCGGCGGCGTTTGGCGCCTACTTCAACCAGGGACAGA<br>uAlaAlaValGlnAlaAlaAlaPheGlyAlaTyrPheAsnGlnGlyGlnI | 4650 |
| 4651 | TCTGTATGTCCACCGAGCGCCTGATTGTCGATGCCAAGGTGGCCGACGCC<br>leCysMetSerThrGluArgLeuIleValAspAlaLysValAlaAspAla | 4700 |

Figure 12D

| | | |
|---|---|---|
| 4701 | TTTGTCGCCCAGTTGGCGGCCAAGGTCGAGACCCTGCGCGCCGGTGATCC<br>PheValAlaGlnLeuAlaAlaLysValGluThrLeuArgAlaGlyAspPr | 4750 |
| 4751 | TGCCGACCCGGAGTCGGTGCTCGGTTCGCTGGTGGACGCCAGCGCTGGCA<br>oAlaAspProGluSerValLeuGlySerLeuValAspAlaSerAlaGlyT | 4800 |
| 4801 | CGCGGATCAAAGCGTTGATCGATGATGCCGTGGCCAAGGGCGCGCGCCTG<br>hrArgIleLysAlaLeuIleAspAspAlaValAlaLysGlyAlaArgLeu | 4850 |
| 4851 | GTAATCGGCGGGCAACTGGAGGGCAGCATCTTGCAGCCGACCCTGCTCGA<br>ValIleGlyGlyGlnLeuGluGlySerIleLeuGlnProThrLeuLeuAs | 4900 |
| 4901 | CGGTGTCGACGCGAGCATGCGTTTGTACCGCGAAGAGTCCTTCGGCCCGG<br>pGlyValAspAlaSerMetArgLeuTyrArgGluGluSerPheGlyProV | 4950 |
| 4951 | TGGCGGTGGTGCTGCGCGGCGAGGGCGAAGAAGCGCTGTTGCAACTGGCC<br>alAlaValValLeuArgGlyGluGlyGluGluAlaLeuLeuGlnLeuAla | 5000 |
| 5001 | AACGACTCCGAGTTCGGTTTGTCGGCGGCGATTTTCAGTCGTGACACCGG<br>AsnAspSerGluPheGlyLeuSerAlaAlaIlePheSerArgAspThrGl | 5050 |
| 5051 | CCGTGCCCTGGCCCTGGCCCAGCGGGTCGAATCGGGCATCTGCCACATCA<br>yArgAlaLeuAlaLeuAlaGlnArgValGluSerGlyIleCysHisIleA | 5100 |
| 5101 | ACGGCCCGACCGTGCACGACGAAGCGCAAATGCCTTTTGGCGGGGTCAAG<br>snGlyProThrValHisAspGluAlaGlnMetProPheGlyGlyValLys | 5150 |
| 5151 | TCCAGCGGCTACGGCAGTTTTGGCGGCAAGGCATCGATTGAGCATTTCAC<br>SerSerGlyTyrGlySerPheGlyGlyLysAlaSerIleGluHisPheTh | 5200 |
| 5201 | TCAGTTGCGCTGGGTCACCCTCCAGAATGGTCCACGGCACTATCCGATCT<br>rGlnLeuArgTrpValThrLeuGlnAsnGlyProArgHisTyrProIleE | 5250 |
| 5251 | GA<br>nd | 5252 |

Figure 12E

Nucleotide sequence of pFI901 (1.8Kb EcoRI/PstI fragment ex pFI973)

```
   1  GAATTCGGGA TCTGGGCTGC CAACCAGTTG GAAGAAAAGA TTCTCGAAGT
  51  CGGTGTCGAC AACGTCGGCG CCTTCATTGC CGAGCCGATC CAGGGCGCCG
 101  GCGGCGTGAT CGTGCCGCCA GAAAGCTACT GGCCGCGCAT CAAGGAAATC
 151  CTCGCCAAGT ACGACATCCT GTTCGTCGCC GATGAAGTGA TTTGCGGTTT
 201  CGGCCGTACC GGCGAGTGGT TCGGCAGCGA TTTCTACGAC CTCAAGCCCG
 251  ACATGATGAC CATCGCCAAG GGCCTGACTT CCGGCTACAT CCCGATGGGT
 301  GGTCTGATCG TGCGCGATTC GGTGGTCGAA GTGCTGAACG AAGGCGGCGA
 351  TTTCAACCAC GGATTCACCT ACTCCGGTCA CCCGGTAGCG GCGGCTGTTG
 401  CCCTGGAAAA CATCCGCATC ATGCGCGAAG AGAAGATTAT CGAGCGCGTC
 451  CAGGAAGAAA CGGCACCGTA TTTGCAAAAG CGTCTGCGTG AACTCAACGA
 501  TCATCCATTG GTGGGTGAAG TTCGCGGGGT AGGGTTGCTG GGCGCTATCG
 551  AACTGGTTCA GGACAAAGCC ACGCGCAAAC GTTACGAAGG CAAGGGCGTG
 601  GGCATGATCT GCCGGCAGTT CTGCTTCGAC AACGGGCTGA TCATGCGCGC
 651  GGTTGGCGAC ACCATGATCA TCGCGCCGCC ACTGGTGATT ACCAAGGCGG
 701  AAATCGATGA GCTGGTGAGC AAGGCACGCA AGTGCCTGGA CCTGACCCTG
 751  AGTGTGTTGC AGGGCTAAGT GCTAGGCTCT GAGCGGGAGT TGTATGAACT
 801  TTCGCTCAGA GCGGTCAGAA AGCTTGGCCT TTCCTTGAAA GACCGCCATG
 851  GATGTTGCCA GACTAGCCAC CGTTCCAAAT GCCCGGGTTC GGCGCGGAAC
 901  AGGTGGTTCA AAAAGCAAA AATTTGGAGC ATTACGCATG AAGGCACTCG
 951  GTAAAAAGCT CGCCGGCAAG ACACTCCTTG CCATGTCCCT GATGGGCATC
1001  ATGGCGGGCG CGGTTCAGGC AGATGACAAA GTCTTGCACG TGTACAACTG
1051  GTCCGATTAC ATCGCGCCGG ACACCATCAA GAAGTTTGAA GACGAGTCGG
1101  GCATCAAGGT GGTCTACGAC GTCTTCGACA GTAACGAAAC CCTCGAAGCC
1151  AAGTTGCTGG CCGGCAAGTC CGGTTACGAC ATCGTGGTGC CTTCGAACAA
1201  CTTCCTGGCC AAGCAGATCA AGGCCGGCGT CTACCAGAAG CTGGACAAGT
1251  CCAAGCTGCC GAACTGGAAG AACCTGAACA CCGATCTGCT CAAGGCCGTT
1301  TCGGTCAGCG ACCCTGGTAA CGAGCACGCC TTCCCGTACA TGTGGGGCTC
```

Figure 13A

```
1351  GATCGGCATC GGCTTCAACG CCGAGAAGGT CAAGGCCGCG CTGGGTCCGG

1401  ATGCACCGAC CAATTCCTGG GACCTGATCT TCAAACCGGA AAACGCCGCC

1451  AAGCTGAAAT CCTGTGGCAT CAGCGTGCTG GATTCGCCAA CCGAGATGAT

1501  TCCGGTGGCC CTGCACTACC TGGGCTACCC GACCGACAGC CAGGACAAGA

1551  AACAACTGGC CGAGGCCGAG GCACTGTTCC TCAAAGTTCG TCCTTCGATC

1601  GGTTACTTCC ACTCCTCCAA GTACATTTCC GACCTGGCCA ACGGCAACAT

1651  CTGCGTGGCG ATCGGCTACT CGGGTGACAT CTATCAGGCC AAGACTCGCG

1701  CCGCCGAAGC CGGTGACAAG GTCAAGGTCA GCTACAACAT TCCCAAAGAA

1751  GGTGCAGGCA GCTTCTACGA CATGGTCGCC ATCCCTAAAG ATGCCGAAAA

1801  CGTCGAAGGC GCCTACAAGT TCATGACCTT CCTGCAG
```

Figure 13B

Nucleotide sequence pFI911 (850bp EcoRI/PstI fragment ex pFI973)

```
  1  CTGCAGACCT TCTGCCAGGC GCACCGGCTC ACGCAGGGTT TTGACTTCCT
 51  GGATCATCAG GCGCTGGTTG CGTTTGACCG ACTGGCCAAT CATCAGGCGA
101  AACGCATTGG AGCCCAGGTC GATAGCGGCG AATAGCGATG CGTCTTCTTT
151  CACGTGAGGA ACTCCTGGCA ACTTCGTCCG CCGAGGGCAA AAAACCGGTT
201  TTGCCGATCC TGCACGGGGT AGATGACATC AGGATGACAT GGAAATTTT
251  TCTGACAGAC GTTTCGTCAC CAGAACGTCA CAGTCGCGGG GCTAGCATCG
301  GGGCTTCCAA TCGGGTCGGG AGCCTTGAAC ATGCTGTTAA CCAACGACAC
351  CCTGATGCAT CGCATCCACC GCGAGTTGCT CGACCACAGT GACGAAGAGC
401  TGGAACTGGA GTTGCTGGAA GACGATCACG ACCTGGCTTC GCTGTTCGCG
451  GATCAACCGG GCGATACCCC GGCCAAGGCC GAGCGCCGTC GTTACTTCAG
501  CGAGTTGTTC CGTTTGCAGG GCGAGTTGGT CAAGTTGCAA AGCTGGGTGG
551  TGAAGACCGG GCACAAGGTG GTGATTCTGT TCGAAGGCCG CGATGCCGCT
601  GGCAAAGGGG GCGTGATCAA GCGCATCACC CAGCGTCTTA ATCCACGGGT
651  CTGCCGGGTC GCGGCGCTTC CCGCGCCGAG TGACCGCGAG CGCACCCAGT
701  GGTATTTCCA GCGTTATGTC TCGCACCTGC CCGCCGCCGG CGAGATCGTC
751  CTGTTCGACC GCAGCTGGTA CAACCGCGCC GGTGTCGAGC AGGTGATGGG
801  CTTTTGCAAC GAGGAACAGT ACGAAGAATT TTTCCGCAGC GTGCCGGAAT
851  TC
```

Figure 14

Nucleotide sequence pFI912 (958bp EcoRI/PstI fragment ex pFI793)

```
  1  CTGCAGGGCC TGGGGCATGC CGAGTCGGCG TCGCAGAACG CCTCTGCCTA
 51  TGCGCTGGAA CGCAAGCAAA TGCGTGCGCC CGCTCGCCCG GTCGGAGTCG
101  AAGCCGAAGT GGCCGACCCC ATTCATTTTC ATCCGGCCAT GCGCCGGGTG
151  TTGCTGGAAC TGAGGGCCTA TGCCGAGGGC ATGCGTGCGG TCGGTTACTG
201  GGCGGCGCAT TTGTTGGATC AGTCCGAGCA GGCCGAGGAT CTGCCCACTC
251  GTCAGCGCGC CTTGCAACTG GCGGAGCTGC TGACGCCGGT GATCAAGGCG
301  TTCTTCACCG AGCAGGGTTT TCGCCTGGCC AGCAACGCCT TGCAGGTGTT
351  CGGTGGCTAC GGCTACGTCA GCGAGTTCGC CATCGAACAG ACCCTGCGCG
401  ACAGCCGGAT CGCGATGATT TACGAGGGCA GCAACGAAAT CCAGGCCAAT
451  GACCTGCTGC TGCGCAAAGT GCTGGGGGAT GAAGGTCGCG CCTTTGGCCA
501  ACTGTTGGCG GTCATGCGCG AAGAGGCCGA ACTGGCCTGT AACGACACCC
551  GCTTTGGCGC TGAGCTGGTG CAGCTGTGCG ACAAACTCGA GACAGTGCAA
601  CTTGAGATAG GGGACCTCGC CGTCACGGAG CGCGAATACC CGTATCGAGC
651  CGCTGGCGAT TTCCTGCGCC TGTGTGGCGT GGCGCTGTTG GGGTTTTCCT
701  GGGCGAGAGC GGCACGGGTG TCTCGCCTGT TACCTGACAG CGATCCACTG
751  CGTCCCAACA AACTGGAAAC CGCGCGTTTC TTCTTTGCCT ACCTGCTGCC
801  AGAAGCCGAT CAACGCCTCG CAGCCATTCG GGCGGCGAGA GCGCCGTTGC
851  CGTTTTTGAT CTGAAAAAAC GCCCGCCAGG CCCAATGTGG CTCGCTCCCA
901  CAAACAGCGC GAACCACATC GAGCCACCGC CGCCACGCCA GTTGTACAGG
951  CCGAATTC
```

Figure 15

Nucleotide sequence pFI913 (959bp EcoRI/PstI fragment ex pFI793)

```
  1  CTGCAGGCTT GCCATATCAG TGGCGACAGC TTCGTCCGCG CTCCAGGCGC
 51  AAGGGCCAAC GACCTGCCGA CGGTGCCGAA TAGGCTGTCG GCGTCCGTTA
101  TTCTGGACGC ACCGCAAAAA CTGTTATTTA CCCGGTCTTC TTCCACTGTA
151  GAACCTTTTC ACTATAGCGG CCCTGCGTGT TCTGCGGGAG CTGCTCATGA
201  TTCTGCACGC GATTCCACTT CCAGCCCGTT GCCGCGCCGT GCTGTTGCGG
251  TTTCTGCACG CACGGCTTTT GCATCAGGCT TGCACAGCCA GCCACAAGGG
301  CAGGTAAGCT CTAGCTCGCA CGTCCTGGGC GTCTCCAGG TCTGCCAACG
351  CGACGCGGAC GCGTCAAACA ACGCCCGGCC CCTAATGAAG CCGGGACACT
401  CAGCCCAGAG GCATTTATGA GTAACAACCT CGACCAGCTC ACCGATTGGT
451  TGAAAGACCA CAAGATCACA GAAGTCGAAT GCATGATTGG CGACTTGACC
501  GGGATCACCC GCGGCAAGAT CTCGCCAACC AACAAGTTCA TTGCCGAAAA
551  AGGCATGCGC CTGCCCGAGA GTGTGCTGTT GCAGACAGTG ACGGGCGACT
601  ATGTCGAAGA CGACATCTAT TACGAACTGC TCGACCCGGC CGACATCGAC
651  ATGATCTGCC GCCCCGACCA GAACGCGGTG TTCCTCGTGC CATGGGCCAT
701  CGAGCCGACC GCGCAGGTGA TTCACGACAC CTACGACAAG CAGGGCAACC
751  CGATCGAGCT GTCGCCACGC AACGTCCTCA GAAAGTCCT CAAACTCTAT
801  TCCGACAAGG GCTGGCAGCC GATCGTGGCG CCGGAAATGG AGTTCTACCT
851  GACCAAGCGC AGTGACGACC CGGATTACCC ATTGCAACCG CCGGTTGGCC
901  GTTCCGGACG TCCGGAAATC GGTCGCCAAT CGTTCTCTAT CGAAGCGGCC
951  AACGAATTC
```

Figure 16

Nucleotide sequence merged contigs pFI913/PCR product/pFI901(4259bp)

```
   1  CTGCAGGCTT GCCATATCAG TGGCGACAGC TTCGTCCGCG CTCCAGGCGC
  51  AAGGGCCAAC GACCTGCCGA CGGTGCCGAA TAGGCTGTCG GCGTCCGTTA
 101  TTCTGGACGC ACCGCAAAAA CTGTTATTTA CCCGGTCTTC TTCCACTGTA
 151  GAACCTTTTC ACTATAGCGG CCCTGCGTGT TCTGCGGGAG CTGCTCATGA
 201  TTCTGCACGC GATTCCACTT CCAGCCCGTT GCCGCGCCGT GCTGTTGCGG
 251  TTTCTGCACG CACGGCTTTT GCATCAGGCT TGCACAGCCA GCCACAAGGG
 301  CAGGTAAGCT CTAGCTCGCA CGTCCTGGGC GTCTCCCAGG TCTGCCAACG
 351  CGACGCGGAC GCGTCAAACA ACGCCCGGCC CCTAATGAAG CCGGGACACT
 401  CAGCCCAGAG GCATTTATGA GTAACAACCT CGACCAGCTC ACCGATTGGT
 451  TGAAAGACCA CAAGATCACA GAAGTCGAAT GCATGATTGG CGACTTGACC
 501  GGGATCACCC GCGGCAAGAT CTCGCCAACC AACAAGTTCA TTGCCGAAAA
 551  AGGCATGCGC CTGCCCGAGA GTGTGCTGTT GCAGACAGTG ACGGGCGACT
 601  ATGTCGAAGA CGACATCTAT TACGAACTGC TCGACCCGGC CGACATCGAC
 651  ATGATCTGCC GCCCCGACCA GAACGCGGTG TTCCTCGTGC CATGGGCCAT
 701  CGAGCCGACC GCGCAGGTGA TTCACGACAC CTACGACAAG CAGGGCAACC
 751  CGATCGAGCT GTCGCCACGC AACGTCCTCA GAAAGTCCT CAAACTCTAT
 801  TCCGACAAGG GCTGGCAGCC GATCGTGGCG CCGGAAATGG AGTTCTACCT
 851  GACCAAGCGC AGTGACGACC CGGATTACCC ATTGCAACCG CCGGTTGGCC
 901  GTTCCGGACG TCCGGAAATC GGTCGCCAAT CGTTCTCTAT CGAAGCGGCC
 951  AACGAATTCG ACCCGCTGTT CGAAGACGTC TACGACTGGT GCGAACTGCA
1001  GGAGCTGGAT CTCGATACGC TGATCCACGA AGACGGCACG CGCAGATGG
1051  AAATCAACTT CCGTCACGGC GACGCGCTGT CCCTGGCCGA CCAGATCCTG
1101  GTGTTCAAGC GCACCATGCG CGAGGCCGCG CTCAAGCACA ACGTGGCCGC
1151  CACGTTCATG GCCAAGCCGA TGACCGGCGA GCCTGGCAGC GCCATGCACC
1201  TGCACCAGAG CATCATCGAT ATCGAGACCG GCAAGAACGT CTTCTCCAAT
1251  GAAGACGGGA GCATGAGCCA GTTGTTCCTC AACCACATCG GCGGCCTGCA
1301  GAAATTCATC CCTGAACTGC TGCCGCTGTT CGCGCCCAAC GTCAACTCGT
```

Figure 19A

```
1351  TCCGCCGCTT CCTGCCGGAC ACTTCGGCGC CGGTGAACGT CGAGTGGGGC
1401  GAAGAAAACC GTACCGTGGG CCTGCGGGTG CCGGATGCCG GCCCTCAAAA
1451  CCGTCGGGTG GAAAACCGCC TGCCGGGTGC CGACGCCAAC CCGTACCTGG
1501  CGATTGCCGC GAGCCTGCTG TGCGGCTACA TCGGCATGGT CGAAGGTATC
1551  AACCCAAGCG CGCCTGTGGT GGGTCGTGGT TACGAGCGGC GCAACCTGCG
1601  TCTGCCGCTG ACCATCGAAG ACGCTCTGGA ACGCATGGAA AACAGCAAGA
1651  CCATCGAGAA ATACCTGGGT CACAACTTCA TCACTGGCTA CGTCGCGGTC
1701  AAGCGGGCCG AGCATGAAAA CTTCAAGCGC GTGATCAGCT CATGGGAACG
1751  GGAATTCCTG TTGTTCGCCG TCTGACACGC CGGGTGCGGC CCTCAAAAGC
1801  CGCACTCCAA CCTCACTAGG AGAGCTTTAT GAGCAACAAC CCGCAAACCC
1851  GTGAATGGCA GAACCTGAGC GCCGAACACC ACCTGGCCCC CTTCAGTGAC
1901  TTCAAGCAAT TGAAGGAAAA AGGCCCGCGC GTCATCACCA GCGCCAAGGG
1951  CGTTTACCTG TGGGACAGCG AAGGCAATCA GATCCTCGAC GGCATGGCCG
2001  GCCTGTGGTG CGTGGCCATC GGTTACGGCC GCGACGAGTT GGCCGAGGCT
2051  GCCAGCAAGC AGATGCGCGA GTTGCCGTAC TACAACCTGT TTTTCCAGAC
2101  CGCTCACCCG CCCGTCCTCG AGCTGGCCAA GGCAATTTCC GATATCGCGC
2151  CAGCAGGCAT GAACCACGTG TTCTTCACCG GTTCCGGCTC CGAAGGCAAT
2201  GACACCATGC TGCGCATGGT TCGCCACTAC TGGGCGATCA AAGGTCAGCC
2251  AAACAAGAAA GTCATTATCA GCCGCAAGAA CGGCTACCAC GGTTCGACCG
2301  TGGCCGGCGC CAGCCTGGGC GGCATGACCT ACATGCACGA ACAGGGCGAC
2351  TTGCCGATCC CGGGCATCGT GCACATTCCG CAGCCGTACT GGTTCGGTGA
2401  AGGCGGCGAC ATGACCCCGG AAGAATTCGG GATCTGGGCT GCCAACCAGT
2451  TGGAAGAAAA GATTCTCGAA GTCGGTGTCG ACAACGTCGG CGCCTTCATT
2501  GCCGAGCCGA TCCAGGGCGC CGGCGGCGTG ATCGTGCCGC CAGAAAGCTA
2551  CTGGCCGCGC ATCAAGGAAA TCCTCGCCAA GTACGACATC CTGTTCGTCG
2601  CCGATGAAGT GATTTGCGGT TTCGGCCGTA CCGGCGAGTG GTTCGGCAGC
2651  GATTTCTACG ACCTCAAGCC CGACATGATG ACCATCGCCA AGGGCCTGAC
2701  TTCCGGCTAC ATCCCGATGG GTGGTCTGAT CGTGCGCGAT CGGTGGTCG
2751  AAGTGCTGAA CGAAGGCGGC GATTTCAACC ACGGATTCAC CTACTCCGGT
```

Figure 19B

```
2801  CACCCGGTAG CGGCGGCTGT TGCCCTGGAA ACATCCGCA TCATGCGCGA
2851  AGAGAAGATT ATCGAGCGCG TCCAGGAAGA AACGGCACCG TATTTGCAAA
2901  AGCGTCTGCG TGAACTCAAC GATCATCCAT TGGTGGGTGA AGTTCGCGGG
2951  GTAGGGTTGC TGGGCGCTAT CGAACTGGTT CAGGACAAAG CCACGCGCAA
3001  ACGTTACGAA GGCAAGGGCG TGGGCATGAT CTGCCGGCAG TTCTGCTTCG
3051  ACAACGGGCT GATCATGCGC GCGGTTGGCG ACACCATGAT CATCGCGCCG
3101  CCACTGGTGA TTACCAAGGC GGAAATCGAT GAGCTGGTGA GCAAGGCACG
3151  CAAGTGCCTG GACCTGACCC TGAGTGTGTT GCAGGGCTAA GTGCTAGGCT
3201  CTGAGCGGGA GTTGTATGAA CTTTCGCTCA GAGCGGTCAG AAAGCTTGGC
3251  CTTTCCTTGA AGACCGCCA TGGATGTTGC CAGACTAGCC ACCGTTCCAA
3301  ATGCCCGGGT TCGGCGCGGA ACAGGTGGTT CAAAAAAGCA AAATTTGGA
3351  GCATTACGCA TGAAGGCACT CGGTAAAAAG CTCGCCGGCA AGACACTCCT
3401  TGCCATGTCC CTGATGGGCA TCATGGCGGG CGCGGTTCAG GCAGATGACA
3451  AAGTCTTGCA CGTGTACAAC TGGTCCGATT ACATCGCGCC GGACACCATC
3501  AAGAAGTTTG AAGACGAGTC GGGCATCAAG GTGGTCTACG ACGTCTTCGA
3551  CAGTAACGAA ACCCTCGAAG CCAAGTTGCT GGCCGGCAAG TCCGGTTACG
3601  ACATCGTGGT GCCTTCGAAC AACTTCCTGG CCAAGCAGAT CAAGGCCGGC
3651  GTCTACCAGA AGCTGGACAA GTCCAAGCTG CCGAACTGGA AGAACCTGAA
3701  CACCGATCTG CTCAAGGCCG TTTCGGTCAG CGACCCTGGT AACGAGCACG
3751  CCTTCCCGTA CATGTGGGGC TCGATCGGCA TCGGCTTCAA CGCCGAGAAG
3801  GTCAAGGCCG CGCTGGGTCC GGATGCACCG ACCAATTCCT GGGACCTGAT
3851  CTTCAAACCG GAAAACGCCG CCAAGCTGAA ATCCTGTGGC ATCAGCGTGC
3901  TGGATTCGCC AACCGAGATG ATTCCGGTGG CCCTGCACTA CCTGGGCTAC
3951  CCGACCGACA GCCAGGACAA GAAACAACTG GCCGAGGCCG AGGCACTGTT
4001  CCTCAAAGTT CGTCCTTCGA TCGGTTACTT CCACTCCTCC AAGTACATTT
4051  CCGACCTGGC CAACGGCAAC ATCTGCGTGG CGATCGGCTA CTCGGGTGAC
4101  ATCTATCAGG CCAAGACTCG CGCCGCCGAA GCCGGTGACA AGGTCAAGGT
4151  CAGCTACAAC ATTCCCAAAG AAGGTGCAGG CAGCTTCTAC GACATGGTCG
4201  CCATCCCTAA AGATGCCGAA AACGTCGAAG GCGCCTACAA GTTCATGACC
```

Figure 19C

4251 TTCCTGCAG

Figure 19D

PRODUCTION OF VANILLIN

This application is a divisional of U.S. patent application Ser. No. 09/155,183 (now U.S. Pat. No. 6,323,011 B1), which was filed on May 3, 1999 (and accepted May 3, 1999) under 35 U.S.C. §371 as a national stage application of PCT/GB97/00809 filed Mar. 24, 1997, claiming priority of Great Britain Application No. 9606187.4 filed Mar. 23, 1996.

The biological material listed below has been deposited under the Budapest Treaty at The National Collections of Industrial and Marine Bacteria Limited (23 St. Machar Drive, Aberdeen AB2 1RY, Scotland, UK):

| NCIMB No. | Description | Date of Deposit |
|---|---|---|
| 40783 | *Pseudomonas fluorescens* biovar V (strain AN103) | Jan. 15, 1996 |
| 40777 | *Escherichia coli* (strain pFI793) containing cosmid pFI703 | Dec. 15, 1995 |

The present invention relates principally to the production of vanillin (4-hydroxy-3-methoxybenzaldehyde), particularly to the production of vanillin other than by extraction from the Vanilla pod.

Vanillin is an important food and drink flavouring agent and a major flavour component of natural vanilla from the Vanilla pod. The use of natural vanilla is limited by its high price. Synthetic vanillin, commonly derived from sulphite liquors produced during the processing of wood pulp for paper manufacture, is frequently used as a low-cost vanilla substitute. Alternative biological processes for the production of natural vanillin and allied flavourings would have considerable industrial value and utility, most particularly if such processes could facilitate the production of vanillin and/or allied flavourings directly in a fermented food or beverage.

The mechanism of vanillin biosynthesis in Vanilla remains substantially uncharacterised. M. H. Zenk (*Anal. Z. Pflanzenphysiol* 53, 404–414 (1965)) showed that vanillin was derived from trans-ferulate (4-hydroxy-3-methoxy-trans-cinnamate) and proposed a mechanism analogous to the classical β-oxidation of fatty acids, with cleavage of a β-keto thioester to produce acetyl SCoA and vanilloyl SCoA (4hydroxy-3-methoxybenzoyl SCoA) and subsequent reduction and CoASH release to generate vanillin. C. Funk and P. E. Brodelius (*Plant Physiol.* 94, 95–101; 102–108 (1990); 99, 256–262 (1992)), proposed a different route, in which the 4-hydroxy group of trans-ferulate became successively methylated and demethylated during the pathway of vanillin biosynthesis; however, the detailed enzymology was not elucidated. In potato tubers and in the fungus, *Polyporus hispidus* (C. J. French, C. P. Vance and G. H. N. Towers, *Phytochemistry* 15, 564–566 (1976)), in cell cultures of *Lithospermum erythrorhizon* (K. Yazaki, L. Heide and M. Tabata, *Phytochemistry* 30, 2233–2236 (1991)) and in cell cultures of carrot (J.-P. Schnitzler, J. Madlung, A. Rose and H. U. Seitz, *Planta* 188, 594–600 (1992)), evidence was obtained from in vitro studies that the corresponding analogue of vanillin, 4-hydroxybenzaldehyde, was an intermediate in the formation of 4-hydroxybenzoate from 4-coumarate (4-hydroxy-trans-cinnamate). There was no requirement for ATP or CoASH, thus apparently ruling out a β-oxidation mechanism. Further studies with cell-free extracts of *Lithospermum erythrorhizon*, however, have in contrast recently established the presence of a β-oxidation route for the conversion of 4-coumarate to 4-hydroxybenzoate (R. Löscher and L. Heide, *Plant Physiol.* 106, 271–279 (1994)); in this case, the conversion was dependent on ATP, $Mg^{2+}$ ions and $NAD^+$ and proceeded via 4-hydroxybenzoyl SCoA, without the intermediate formation of 4-hydroxybenzaldehyde.

In the Gram-negative bacterium, *Pseudomonas acidovorans*, trans-ferulate was shown to be catabolised to vanillate and acetate, apparently via vanillin (A. Toms and J. M. Wood, *Biochemistry* 9, 337–343 (1970)). Although in cell-free extracts $NAD^+$ was necessary for the oxidation of vanillin to vanillate and for the further oxidation of vanillate to protocatechuate and formate, no mention was made of any other cofactor requirements. Further studies of ferulate utilisation in Pseudomonas species have been reported (V. Andreoni and G. Bestetti, *FEMS Microbiology Ecology* 53, 129–132 (1988); T. Omori, K. Hatakeyama and T. Kodama, *Appl. Microbiol. Biotechnol.* 29, 497–500 (1988); Z. Huang, L. Dostal and J. P. N. Rosazza, *Appl. Env. Microbiol.* 59, 2244–2250 (1993)); however, these have not sought to elucidate further the mechanism of the two-carbon cleavage of ferulate. Zenk et al (1980) *Anal. Biochem.* 101, 182–187 describe a procedure for the enzymatic synthesis and isolation of cinnamoyl-CoA thioesters using a bacterial system. In contrast, the enzymology and genetics of the utilisation of simple benzene derivatives, including benzoic acids and phenols, by Pseudomonas have been intensively studied (T. K. Kirk, T. Higuchi and H.-M. Chang (eds.), "*Lignin biodegradation*", CRC Press, Boca Raton, Fla, USA (1980); D. T. Gibson (ed.), "*Microbial degradation of organic compounds*", Marcel Dekker, New York (1984); J. L. Ramos, A. Wasserfallen, K. Rose and K. N. Timmis, *Science* 235, 593–596 (1987); C. S. Harwood, N. N. Nichols, M. K. Kim, J. L. Ditty and R. E. Parales, *J. Bacteriol.* 176, 6479–6488 (1994); S. Romerosteiner, R. E. Parales, C. S. Harwood and J. E. Houghton, *J. Bacteriol.* 176, 5771–5779 (1994); J. Inoue, J. P. Shaw, M. Rekik and S. Harayama, *J. Bacteriol.* 177, 1196–1201 (1995)).

A survey of potential microbial routes to aromatic aldehydes, including routes (i) from trans-cinnamic acids, (ii) from benzoic acids by reduction and (iii) by conversion of aromatic amino acids to phenylpyruvic acids followed by treatment with base, has been presented by J. Casey and R. Dobb (*Enzyme Microb. Technol.* 14, 739–747 (1992)).

U.S. Pat. No. 5,128,253 describes a method of producing vanillin from ferulic acid by various microorganisms and extracts thereof or enzymes derived therefrom in the presence of a sulphydryl compound but does not disclose what any of the enzymes involved in the conversion of ferulic acid to vanillin are. U.S. Pat. No. 5,279,950 is a continuation-in-part application of U.S. Pat. No. 5,128,253 which additionally describes that Vanilla calluses can be used in the process.

WO 94/13614 describes the production of vanillin from ferulic acid by the action of Vanilla root material and makes use of an adsorbent, such as charcoal, to extract vanillin but does not disclose the specific enzymes involved.

EP 0 453 368 describes that a culture of Pycnoporus can convert trans-ferulic acid into vanillin but does not disclose the specific enzymes involved.

WO 94/02621 describes the production of vanillin from trans-ferulic acid by the action of a lipoxygenase enzyme. EP 0 405 197 describes the production of vanillin from eugenol/isoeugenol by bacteria from the genera Serratia, Klebsiella and Enterobacter by oxidation.

Vanillin may also be produced from phenolic stilbenes as is mentioned in Hagedorn & Kaphammer (1994) *Ann. Rev. Microbiol.* 48, 773–800.

Vanillic acid is also a useful compound as it can be polymerised into oligomers or used as a monomer in the synthesis of polyesters; similarly p-hydroxybenzoic acid is also useful for polymer synthesis.

A first aspect of the invention provides a method of producing vanillin comprising the steps of (1) providing trans-ferulic acid or a salt thereof; and
(2) providing trans-ferulate:CoASH ligase activity (enzyme activity I), trans-feruloyl ScoA hydratase activity (enzyme activity II), and 4-hydroxy-3-methoxyphenyl-β-hydroxy-propionyl SCoA (HMPHP SCoA) cleavage activity (enzyme activity III).

The advantages of the present invention over chemical synthesis or extraction from the Vanilla pod include (i) economic advantage over extraction from Vanilla pod and freedom from geographical dependence on Vanilla growing areas; (ii) the ability to produce vanillin by a natural process, involving biological catalysts; (iii) the benefits of generating a natural flavour in situ in a fermented food or beverage, if the genes are expressed in appropriate food-grade hosts—eg lactic acid bacteria or yeasts; and (iv) the possibility of expanding the range of plants in which vanillin and related substances might be produced and from which they might be extracted. These and other examples of the methods of the invention are described in more detail below.

We have determined the mechanism of chain-shortening of trans-ferulate (trans-ferulic acid) by a strain of *Pseudomonas fluorescens* (named *Ps. fluorescens* biovar. V, strain AN103 and which we have abbreviated at some points to AN103) isolated from soil. Our data indicate clearly that vanillin (4-hydroxy-3-methoxy benzaldehyde) is an intermediate and that the mechanism does not involve β-oxidation. The vanillin pathway of *Ps. fluorescens* biovar. V, strain AN103 is described in FIG. 1. Trans-ferulic acid (or a salt thereof) is interconverted with trans-feruloyl ScoA in the presence of CoASH; trans-feruloyl SCoA is interconverted with 4-hydroxy-3-methoxyphenyl-β-hydroxypropionyl SCoA (HMPHP SCoA); and HMPHP SCoA is interconverted with vanillin.

For convenience, trans-ferulate:CoASH ligase activity is called enzyme activity I, trans-feruloyl SCoA hydratase activity is called enzyme activity II; and HMPHP SCoA cleavage activity is called enzyme activity III. The interconversions performed by these enzyme activities is shown in FIG. 1.

The method of producing vanillin provided by the invention therefore includes the steps of exposing trans-ferulic acid or a salt thereof to enzyme activity I and forming a product, exposing the said product of enzyme activity I to enzyme activity II to form a product and exposing the said product of enzyme activity II to enzyme activity III to form a product.

Trans-ferulic acid or a salt thereof may be provided directly, for example by supplying pre-prepared trans-ferulic acid or a salt thereof, or it may be provided indirectly, for example by supplying a precursor of trans-ferulic acid or a precursor of a salt of trans-ferulic acid and means to convert the said precursor into trans-ferulic acid or a salt thereof. As is described in more detail below, it is convenient if the precursor is an ester of trans-ferulic acid and the means to convert said ester is a suitable esterase. By "providing trans-ferulate:CoASH ligase activity (enzyme activity I), trans-feruloyl ScoA hydratase activity (enzyme activity II), and 4-hydroxy-3-methoxyphenyl-β-hydroxy-propionyl SCoA (HMPHP ScoA) cleavage activity (enzyme activity III)" we include the provision of the enzyme activities in any suitable form to effect the said production of vanillin. For example, as is discussed in more detail below, the method of the invention specifically includes, but is not limited to, the provision of the enzyme activities (a) by intact or permeabilised *Ps. fluorescens* biovar. V, strain AN103 or a mutant thereof, (b) at least one of enzyme activities II or III of which is in a form substantially free of cellular material, (c) by intact or permeabilised cells in culture, particularly microorganisms, which have been genetically modified to contain genes which encode enzyme activities II or III (for example, food grade microorganisms such as lactic acid bacteria and brewing yeast), and (d) by plants which have been genetically modified to contain genes which encode said enzyme activities.

It is preferred if means for converting vanillin to a non-vanillin product is absent or reduced. Of course, the enzyme activity III is not such a means. Conveniently, these enzyme activities are provided by the soil bacterium *Pseudomonas fluorescens* biovar. V, strain AN103 the said bacterium being that deposited under the Budapest Treaty at the National Collection of Industrial and Marine Bacteria Limited, AURIS Business Centre, 23 St. Machar Drive, Aberdeen AB2 1RY, Scotland under Accession No NCIMB 40783, or a mutant or variant thereof. By "mutant or variant thereof" we include any mutant or variant of the said bacterium provided that the bacterium retains the said enzyme activities whether or not at the same levels. It will be appreciated that the said enzyme activities can be retained even if the genes encoding said enzymes are mutated. For example, mutants which constitutively express (as opposed to conditionally or inducibly express) the said enzyme activities are particularly useful mutants of *Ps. fluorescens* biovar. V, strain AN103, as are variants in which one or more of the enzymes with the said activities exhibit more favourable kinetic characteristics (for example, an increased turn-over number or a decreased $K_m$)

When *Ps. fluorescens* biovar. V, strain AN103 is growing on trans-ferulate it will derive maximum benefit if vanillin is catabolised further in order to provide more energy. However, in order to maximise the production of vanillin by *Ps. fluorescens* biovar. V, strain AN103 it is preferred that the means for converting vanillin to a non-vanillin product is absent or reduced. We have found that in *Ps. fluorescens* biovar. V, strain AN103 vanillin is converted to vanillic acid or a salt thereof by vanillin:$NAD^+$ oxidoreductase. It is preferred if a mutant of *Ps. fluorescens* biovar. V, strain AN103 wherein the vanillin:$NAD^+$ oxidoreductase activity is absent or reduced is used in the method. Such a mutant can be made using a gene replacement strategy with a disrupted vanillin:NAD oxidoreductase gene, or a sequence of DNA from which this gene has been deleted. Gene replacement is well known in the art of bacterial genetics. Alternatively, isolation of such a mutant may be achieved by classical chemical mutagenesis, selecting on the basis of inability to grow on vanillin.

It will be appreciated that there are other means for converting vanillin to a non-vanillin product and it is preferred if these are absent or reduced in the method.

Although *Ps. fluorescens* biovar. V, strain AN103 or mutants or variants thereof themselves are useful in the method of the invention as whole cells or permeabilised or immobilised cells, it is preferred if the enzyme activities I, II and III are provided by an intact-cell-free system of *Ps. fluorescens* biovar, V, stain AN103 or a mutant or variant thereof. Suitable systems and extracts may be used by methods well known in the art, for example by French pressure cell or sonication followed by centrifugation. Alternatively, whole cells may be permeabilised using methods well known in the art, for example using detergents such as dimethyl sulphoxide (DMSO).

Using such an intact-cell-free system allows the necessary substrates and any cofactors to reach readily the relevant enzymes and for the products to be released readily into the reaction medium if this is necessary for further reaction; however as discussed below, at least some of the enzymes of the invention may be involved in substrate (metabolic) channelling.

We have found that none of the enzyme activities I, II and III from *Ps. fluorescens* biovar. V, strain AN103 is dependent on $NAD^+$ whereas enzyme activity IV from *Ps. fluorescens* (vanillin:$NAD^+$ oxido-reductase) requires $NAD^+$.

Thus, a preferred way of reducing means for converting vanillin to a non-vanillin product in an intact-cell-free system of *Ps. fluorescens* biovar. V, strain AN103 (or in a cell-permeabilised system of *Ps. fluorescens* biovar. V, strain AN103) is to omit NAD$^+$ from the reaction system. Any exogenous NAD$^+$ is readily and rapidly depleted by the presence of trans-ferulate in the system.

For the microorganisms of the present invention which can be used in the method of vanillin production, including *Ps. fluorescens* biovar. V, strain AN103, at least three main types of bioreactor may be used for the biotransformation reactions: the batch tank, the packed bed and the continuous-flow stirred tank; their applications and characteristics have been reviewed (M. D. Lilly in "Recent Advances in Biotechnology", eds. F. Vardar-Sukan and S. S. Sukan, Kluwer Academic Publishers, Dordrecht, 1992, pp 47–68 and loc. cit.).

As is described in more detail below, enzyme activities II and III are available free from other enzyme activities, for example directly or indirectly from *Ps. fluorescens* biovar. V, strain AN103 and from other organisms or cells which have been genetically modified to express genes encoding the said enzyme activities.

It will be appreciated that other microorganisms will be found which will be useful in the methods of the invention, for example, by screening. Such microorganisms and methods of screening and methods of use form part of the invention. The method of screening for other microorganisms possessing activities I, II and III is essentially that already described in the Materials and Methods section in the Examples for the isolation of AN 103. The important aspect is isolation from an environment rich in trans-ferulate or related compounds (eg 4-trans-coumarate, trans-caffeate [3,4-dihydroxy-trans-cinnamate] which, as described below, may also be substrates for enzyme activity I) and selection for growth on trans-ferulate (preferably) as sole carbon source. In practice, preferred sources are those in which plant-derived materials are being degraded; in addition to soil or compost, this would include the outflow or residues from factories or other installations processing such materials—eg sugar-beet factories, cocoa fermentation heaps etc—and the contents of the gastro-intestinal tract, particularly of ruminants and other herbivores. It is possible that anaerobes might be found possessing these activities and due account can readily be taken of this in the isolation procedure. A priori, isolation of organisms with these activities might also be possible from marine environments.

Genera in which further microorganisms useful in the invention will be found include Pseudomonas, Arthrobacter, Alcaligenes, Acinetobacter, Flavobacterium, Agrobacterium, Rhizobium, Streptomyces, Saccharomyces, Penicillium and Aspergillus.

An alternative or additional approach is to use any one of the Pseudomonas genes encoding enzyme activities II or III described herein or redundant sequences designed from the Pseudomonas enzyme amino-acid sequences in DNA probes or PCR amplification strategies to find related genes in other organisms. As is made more clear below, enzymes and nucleotide sequences which are functionally equivalent to those of isolated from AN103 but which differ in sequence form part of the invention.

Our studies indicate that the enzyme which interconverts trans-ferulate and trans-feruloyl SCoA in *Ps. fluorescens* biovar. V, strain AN103 uses Coenzyme A (CoASH), ATP and Mg$^{2+}$ or other functionally equivalent cofactors. Thus, it is preferred that the method further comprises the step of (3) providing any one of the cofactors CoASH, ATP or Mg$^{2+}$ or other functionally equivalent cofactors. ATP is adenosine triphosphate. It is well known that other functionally equivalent cofactors can substitute in some cases for CoASH, ATP or Mg$^{2+}$. For example Mn$^{2+}$ may be used in place of Mg$^{2+}$ and derivatives or analogues of ATP, preferably with a hydrolysable γ-phosphate, may be used in place of ATP.

We have also determined that, at least when the enzyme activity I is provided by the Pseudomonas AN103 enzyme which interconverts trans-ferulate and trans-feruloyl SCoA and which enzyme uses ATP and Coenzyme ASH, it is convenient to include a system wherein either one, or both, of the cofactors Coenzyme ASH and ATP is recycled. The following ATP generation and CoASH recycling systems are preferred.

ATP generation:

(i) trans-Ferulate+CoASH+ATP+H$_2$O→Vanillin+Acetyl SCoA+AMP+PPi (overall reaction catalysed by *Ps. fluorescens* biovar. V, strain AN103 extract)

(ii) AMP+ATP⇌2 ADP (adenylate kinase)

(iii) Acetyl~P+ADP⇌Acetate+ATP (acetate kinase)

(iv) Sum: trans-Ferulate+CoASH+2 Acetyl~P+ H$_2$O→Vanillin+Acetyl SCoA+2 Acetate+PPi CoASH recycling is achievable using commercially-available citrate synthase (EC 4.1.3.7) and citrate lyase (EC 4.1.3.6), viz:

(v) Acetyl SCoA+Oxaloacetate+H$_2$O⇌Citrate+CoASH (citrate synthase)

(vi) Citrate⇌Oxaloacetate+Acetate (citrate lyase)

Overall sum, (iv)–(vi):

(vii) trans-Ferulate+2 Acetyl~P+2 H$_2$O→Vanillin+3 Acetate+PPi

The acetyl~P used in the overall process, (vii), would not itself be generated by enzymic means; however, none of its atoms would appear in the vanillin product.

Acetyl phosphate is commercially available or can be synthesised using the method described by Stadtman (1957) *Meth. Enzymol.* 3, 228–231.

The reagents are commercially available from, for example Sigma Chemical Co, Fancy Road, Poole, Dorset, UK. Citrate lyase is typically from *Enterobacter aerogenes*; citrate synthase is typically from chicken heart, pigeon breast muscle or porcine heart.

Thus, it is preferred if coenzyme ASH is recycled using the enzymes citrate synthase and citrate lyase; and it is preferred if the ATP is generated using the enzymes adenylate kinase (EC 2.7.4.3) and acetate kinase (EC 2.7.2.1).

The co-factor recycling system is particularly preferred when using an intact-cell-free system.

Trans-ferulic acid or a salt thereof is readily available from plant material. Suitably, trans-ferulic acid or a salt thereof is released from the plant material by the action of ferulic acid esterase. Thus, in a particularly preferred embodiment of the invention the trans-ferulic acid or salt thereof is provided by the action of ferulic acid esterase on plant material.

Trans-ferulic acid and trans4-coumaric acid can together represent up to 1.5% by weight of the cell walls of temperate grasses (R. D. Hartley and E. C. Jones, *Phytochemistry* 16, 1531–1534 (1977)). Trans-ferulic acid is reported to comprise 0.5% (w/w) of wheat bran (M. C. Ralet, J.-F. Thibault and G. Della Valle, *J. Cereal Sci.* 11, 249–259 (1990)), 3.1% of maize bran (L. Saulnier, C. Marot, E. Chanliaud and J.-F. Thibault, *Carbohydr. Polym.* 26, 279–287 (1995)) and 0.8% of sugar beet pulp (V. Micard, G. M. G. C. Renard and J.-F. Thibault, *Lebensm.-Wiss. u-Technol.* 27, 59–66 (1994)). These materials are amongst the preferred sources of trans-ferulic acid. Since trans-ferulic acid is present esterified with cell-wall polysaccharides, hydrolysis is essential. Alkaline or acid hydrolysis is possible, but enzymic hydrolysis is preferred. Typically, the initial step is the partial enzymic hydrolysis of carbohydrates (arabinans, xylans, rhamnogalacturanans) to which trans-ferulate is linked, followed by the release of trans-ferulate from the oligosaccharide fragments by trans-ferulic acid esterase activity. In practice, both steps may occur simultaneously in the reaction mixture. Descriptions of representative laboratory-scale processes are available in the literature (for example see L.

P. Christov and B. A. Prior, *Enzyme Microb. Technol.* 15, 460–475 (1993)); C. B. Faulds and G. Williamson, *Appl. Microbiol. Biotechnol.* 43, 1082–1087 (1995); C. B. Faulds, P. A. Kroon, L. Saulnier, J.-F. Thibault and G. Williamson, *Carbohydrate Polymers* 27, 187–190 (1995)). Phenolic acid-releasing enzymes have been reported from a number of microorganisms, including *Streptomyces olivochromogenes* (C. B. Faulds and G. Williamson, *J. Gen. Microbiol.* 137, 2337–2345 (1991)), *Penicillium pinophilum* (A. Castanares, S. I. McCrae and T. M. Wood, *Enzyme Microb. Technol.* 14, 875–884 (1992)), Neocallimastix spp. (W. S. Borneman, R. D. Hartley, W. H. Morrison, D. E. Akin and L. G. Ljungdahl, *Appl. Microbiol. Biotechnol.* 33, 345–35,1 (1990)), *Schizophyllum commune* (R. C. MacKenzie and D. Bilous, *Appl. Envir. Microbiol.* 54, 1170–1173 (1988)) and Aspergillus spp. (M. Tenkanen, J. Schuseil, J. Puls and K. Poutanen, *J. Biotechnol.* 18, 69–84 (1991); C. B. Faulds and G. Williamson, *Microbiology* 140, 779–787 (1994)). A trans-ferulic acid esterase (XYLD) has been characterised from *Pseudomonas fluorescens* subsp. cellulosa, together with an arabinofuranosidase (XYLC) and an endoxylanase (XYLB; L. M. A. Ferreira, T. M. Wood, G. Williamson, C. B. Faulds, G. P. Hazlewood and H. J. Gilbert, *Biochem. J.* 294, 349–355 (1993)). The genes for all three enzymes have been isolated (G. P. Hazlewood and H. J. Gilbert, in "Xylans and Xylanases", eds. J. Visser, G. Beldman, M. A. Kustersvan Someren and A. G. J. Voragen, Elsevier, Amsterdam, pp 259–273 (1992)). All of these references are incorporated herein by reference.

Thus, advantageously the trans-ferulic acid or a salt thereof may be provided by the action of trans-ferulic acid esterase on said ester. More particularly, it is advantageous to introduce a gene encoding said esterase into a host cell or organism which is being used in the methods of the invention. Thus, it is convenient to introduce a trans-ferulic acid esterase gene, such as the aforementioned XYLD gene, into a plant which is being used in the methods of the invention.

Although, as described above, the method may be performed using enzyme activities I, II and III which are provided by *Ps. fluorescens* biovar. V, strain AN103 or mutants or variants thereof themselves, or intact-cell-free extracts thereof, it is preferred if at least one of the enzyme activities II and III is provided by a substantially purified enzyme. Substantially purified enzymes with enzyme activities II and III are described below.

In a particularly preferred embodiment of the invention the method of the first aspect of the invention further comprises providing a compound, in addition to trans-ferulic acid or a salt thereof, which may be converted by any one of enzyme activities I, II or III into a desirable product. Suitably said compound is converted by any one or more of said enzyme activities into a product which is found in, and preferably contributes to the taste or aroma of, vanilla as extracted from Vanilla pod.

Vanilla as extracted from Vanilla pod contains vanillin as a major component but also smaller quantities of desirable components such as p-hydroxybenzoic acid, p-hydroxybenzaldehyde and vanillic acid. Typically these components, and vanillin, are present as glucosides in green vanilla pods as well as in the free form. However, upon hydrolysis or fermentation of the green pods or of hydrolysis of the fermented pods, most of the components are present in the free form.

Thus, it is particularly preferred if said compound is any one of trans-4-coumaric acid or a salt thereof, trans-4-coumaroyl SCoA, trans-caffeic acid or a salt thereof, trans-caffeoyl SCoA, or 3,4-methylenedioxy-trans-cinnamic acid or a salt thereof. By the action of one or more of enzyme activities I, II or III trans4-coumaric acid or a salt thereof and trans-4-coumaroyl SCoA are converted to p-hydroxybenzaldehyde; trans-caffeic acid or a salt thereof and trans-caffeoyl SCoA are converted to 3,4-dihydroxybenzaldehyde; and 3,4methylenedioxy-transcinnamic acid or a salt thereof is converted to heliotropin.

It is preferred if the compound is trans4-coumaric acid or a salt thereof or trans-4-coumaroyl SCoA and that the desirable product is 4-hydroxybenzaldehyde which is a significant component of natural Vanilla extract.

The enzyme activities I, II and III from *Ps. fluorescens* biovar V, strain AN103 are able to use trans-caffeate and trans-4-coumarate, (and, as appropriate, the products of their reaction with enzyme activity I) with reasonable efficiency whereas cinnamate and 3,4-methylenedioxy-transcinnamate, although may be used as substrates, are poor substrates of the AN103 enzymes.

Thus, the method of the first aspect of the invention is suited to make vanilla flavourings and aromas which more closely resemble the vanilla from Vanilla pod.

The method of the first aspect of the invention may, in certain circumstances, also be performed using the host cells and genetically modified cells and organisms as described below in more detail.

A second aspect of the invention provides a method of producing vanillic acid, or a salt thereof, comprising the steps of (1) providing trans-ferulic acid or a salt thereof;

(2) providing trans-ferulate:CoASH ligase activity, trans-feruloyl SCoA hydratase activity, and 4-hydroxy-3-methoxyphenyl-β-hydroxy-propionyl SCoA (HMPHP SCoA) cleavage activity; and (3) providing an activity that interconverts vanillin and vanillic acid.

For convenience, the activity that interconverts vanillin and vanillic acid is called enzyme activity IV. Conveniently the activity is provided by vanillin:NAD$^+$ oxidoreductase (vanillin dehydrogenase). Suitably, this activity is provided by *Ps. fluorescens* biovar. V, strain AN103. Methods of converting vanillin to vanillic acid or a salt thereof are also known in the art, for example Perestelo et al (1989) *App. Environ. Microbiol.* 55, 1660–1662 describes the production of vanillic acid from vanillin by resting cells of *Serratia marcescens* and Pomelto & Crawford (1983) *App. Environ. Microbiol.* 45, 1582–1585 describe whole-cell bioconversion of vanillin to vanillic acid by *Streptomyces viridosporus*.

The method of producing vanillic acid provided by the invention therefore includes the steps of exposing trans-ferulic acid or a salt thereof to enzyme activity I and forming a product, exposing the said product of enzyme activity I to enzyme activity II to form a product, exposing the said product of enzyme activity II to enzyme activity III to form a product, and exposing the said product of enzyme activity III to enzyme activity IV to form a product.

It will be appreciated that vanillic acid can be made by the same means as vanillin is made in the method of the first aspect of the invention provided, of course, that enzyme activity IV is supplied.

A further preferred embodiment of the first aspect of the invention comprises the further step of separating vanillin from the other reaction components.

Vanillin, and other aromatic aldehydes, are, for example, recoverable by extraction with solvent, including supercritical carbon dioxide, and by organophilic pervaporation, using membranes constructed of hydrophobic polymers (G. Bengston and K. W. Bodekker, in "Bioflavour 95", eds. P. Étiévant and P. Schreier, INRA, Paris, pp 393–403 (1995); S. M. Zhang and E. Drioli, *Separ. Sci. Technol.* 8, 1–31 (1994)); pervaporation technology has been applied, for example, to the recovery of flavour compounds of wine (N. Rajagopalan and M. Cheryan, *J. Membrane Sci.* 104, 243–250 (1995)). Solid-phase extraction, followed by desorption with solvent, is also possible, though less preferred.

However, in some circumstances, particularly where minor reaction products are present which are similar to compounds present in the vanilla isolated from Vanilla pod, vanillin is not isolated.

A further preferred embodiment of the second aspect of the invention comprises the further step of separating vanillic acid or a salt thereof from the other reaction components.

Vanillic acid and other carboxylic acids may, for example, be recovered by solid-phase extraction, by solvent extraction under acidic conditions, or by pertraction; for example, L. Boyadzhiev and I. Atanassova (*Process Biochemistry* 29, 237–243 (1994)) describe the recovery of the aromatic amino acid, phenylalanine, by pertraction.

A third aspect of the invention provides *Pseudomonas fluorescens* biovar. V, strain AN103 as deposited under the Budapest Treaty at the National Collections of Industrial and Marine Bacteria Limited, AURIS Business Centre, 23 St Machar Drive, Aberdeen AB2 1RY, Scotland under Accession No NCIMB 40783, or a mutant or variant thereof. Preferred mutants and variants are the same as those preferred in the first aspect of the invention. A particularly preferred mutant of *Ps. fluorescens* biovar. V, strain AN103 is one which accumulates vanillin when provided with trans-ferulic acid or a salt thereof. Conveniently, this is a mutant of *Ps. fluorescens* biovar. V, strain AN103 wherein vanillin:NAD+ oxidoreductase activity is absent or reduced. Suitably, there is a mutation in the gene encoding vanillin:NAD+ oxidoreductase such that the enzyme activity is absent or substantially reduced. Such a mutant can be made as described above.

A fourth aspect of the invention provides a polypeptide which, in the presence of appropriate cofactors if any, is capable of catalysing the interconversion of trans-feruloyl SCoA and 4-hydroxy-3-methoxy-phenyl-β-hydroxypropionyl SCoA (HMPHP SCoA). Such a polypeptide has enzyme activity II. Conveniently, the polypeptide comprises trans-feruloyl SCoA hydratase; more conveniently the polypeptide comprises trans-feruloyl SCoA hydratase from *Ps. fluorescens* biovar. V, strain AN103 or fragments or variants thereof which have at least 1% of the specific activity of the native enzyme (in relation to trans-feruloyl SCoA hydratase activity), preferably at least 10%, more preferably at least 100%.

The enzyme activity is readily purified as described in the Examples. Modifications to this procedure may be readily made by the person skilled in the art so that a polypeptide with enzyme activity II can be obtained from any suitable source making use of the enzyme activity II assay procedure described in the Examples.

It is preferred if the polypeptide of the fourth aspect of the invention comprises the amino acid sequence.

```
MetSerThrTyrGluGlyArgTrpLysThrValLysValGluIleGluAspGlyIleAla      (SEQ ID No 2)

PheValIleLeuAsnArgProGluLysArgAsnAlaMetSerProThrLeuAsnArgGlu

MetIleAspValLeuGluThrLeuGluGlnAspProAlaAlaGlyValLeuValLeuThr

GlyAlaGlyGluAlaTrpThrAlaGlyMetAspLeuLysGluTyrPheArgGluValAsp

AlaGlyProGluIleLeuGlnGluLysIleArgArgGluAlaSerGlnTrpGlnTrpLys

LeuLeuArgMetTyrAlaLysProThrIleAlaMetValAsnGlyTrpCysPheGlyGly

GlyPheSerProLeuValAlaCysAspLeuAlaIleCysAlaAspGluAlaThrPheGly

LeuSerGluIleAsnTrpGlyIleProProGlyAsnLeuValSarLysAlaMetAlaAsp

ThrValGlyHisArgGlnSerLeuTyrTyrIleMetThrGlyLysThrPheGlyGlyGln

LysAlaAlaGluMetGlyLeuValAsnGluSerValProLeuAlaGlnLeuArgGluVal

ThrIleGluLeuAlaArgAsnLeuLeuGluLysAsnProValValLeuArgAlaAlaLys

HisGlyPheLysArgCysArgGluLeuThrTrpGluGlnAsnGluAspTyrLeuTyrAla

LysLeuAspGlnSerArgLeuLeuAspThrGluGlyGlyArgGluGlnGlyMetLysGln

PheLeuAspAspLysSerIleLysProGlyLeuGlnAlaTyrLysArg,
``` or a fragment or variant thereof.

The amino acid sequence is that given in FIG. 12 as that encoded by nucleotides 2872 to 3699.

A fifth aspect of the invention provides a polypeptide which, in the presence of appropriate cofactors if any, is capable of catalysing the interconversion of 4-hydroxy-3-methoxyphenyl-β-hydroxy-propionyl SCoA (HMPHP SCoA) and vanillin. Such a polypeptide has enzyme activity III. Conveniently, the polypeptide comprises HMPHP SCoA cleavage enzyme; more conveniently the polypeptide comprises HMPHP SCoA cleavage enzyme from *Ps. fluorescens* biovar. V, strain AN103 or fragments or variants thereof which have at least 1% of the specific activity of the native enzyme (in relation to HMPHP SCoA cleavage activity), preferably at least 10%, more preferably at least 100%.

The enzyme activity is readily purified as described in the Examples. Modifications to this procedure may be readily made by the person skilled in the art so that a polypeptide with enzyme activity III can be obtained from any suitable source-making use of the enzyme activity III assay procedure described in the Examples.

It is preferred if the polypeptide of the fifth aspect of the invention comprises the amino acid sequence MetSerThrTyrGluGlyArgTrpLysThrValLysValGluIleGluAspGlyIleAla    (SEQ ID No 2)

PheValIleLeuAsnArgProGluLysArgAsnAlaMetSerProThrLeuAsnArgGlu

MetIleAspValLeuGluThrLeuGluGlnAspProAlaAlaGlyValLeuValLeuThr

GlyAlaGlyGluAlaTrpThrAlaGlyMetAspLeuLysGluTyrPheArgGluValAsp

AlaGlyProGluIleLeuGlnGluLysIleArgArgGluAlaSerGlnTrpGlnTrpLys

LeuLeuArgMetTyrAlaLysProThrIleAlaMetValAsnGlyTrpCysPheGlyGly

GlyPheSerProLeuValAlaCysAspLeuAlaIleCysAlaAspGluAlaThrPheGly

LeuSerGluIleAsnTrpGlyIleProProGlyAsnLeuValSerLysAlaMetAlaAsp

ThrValGlyHisArgGlnSerLeuTyrTyrIleMetThrGlyLysThrPheGlyGlyGln

LysAlaAlaGluMetGlyLeuValAsnGluSerValProLeuAlaGlnLeuArgGluVal

ThrIleGluLeuAlaArgAsnLeuLeuGluLysAsnProValValLeuArgAlaAlaLys

HisGlyPheLysArgCysArgGluLeuThrTrpGluGlnAsnGluAspTyrLeuTyrAla

LysLeuAspGlnSerArgLeuLeuAspThrGluGlyGlyArgGluGlnGlyMetLysGln

PheLeuAspAspLysSerIleLysProGlyLeuGlnAlaTyrLysArg, or a fragment or variant thereof.

The amino acid sequence is that given in FIG. 12 as that encoded by nucleotides 2872 to 3699.

A sixth aspect of the invention provides a polypeptide comprising the amino acid sequence MetLeuAspValProLeuLeuIleGlyGlyGlnSerCysProAlaArgAspGlyArgThr    (SEQ ID No 4)

PheGluArgArgAsnProValThrGlyGluLeuValSerArgValAlaAlaAlaThrLeu

GluAspAlaAspAlaAlaValAlaAlaAlaGlnGlnAlaPheProAlaTrpAlaAlaLeu

AlaProAsnGluArgArgSerArgLeuLeuLysAlaAlaGluGlnLeuGlnAlaArgSer

GlyGluPheIleGluAlaAlaGlyGluThrGlyAlaMetAlaAsnTrpTyrGlyPheAsn

ValArgLeuAlaAlaAsnMetLeuArgGluAlaAlaSerMetThrThrGlnValAsnGly

GluValIleProSerAspValProGlySerPheAlaMetAlaLeuArgGlnProCysGly

ValValLeuGlyIleAlaProTrpAsnAlaProValIleLeuAlaThrArgAlaIleAla

MetProLeuAlaCysGlyAsnThrValValLeuLysAlaSerGluLeuSerProAlaVal

HisArgLeuIleGlyGlnValLeuGlnAspAlaGlyLeuGlyAspGlyValValAsnVal

IleSerAsnAlaProAlaAspAlaAlaGlnIleValGluArgLeuIleAlaAsnProAla

ValArgArgValAsnPheThrGlySerThrHisValGlyArgIleValGlyGluLeuSer

AlaArgHisLeuLysProAlaLeuLeuGluLeuGlyGlyLysAlaProLeuLeuValLeu

AspAspAlaAspLeuGluAlaAlaValGlnAlaAlaAlaPheGlyAlaTyrPheAsnGln

GlyGlnIleCysMetSerThrGluArgLeuIleValAspAlaLysValAlaAspAlaPhe

ValAlaGlnLeuAlaAlaLysValGluThrLeuArgAlaGlyAspProAlaAspProGlu

SerValLeuGlySerLeuValAspAlaSerAlaGlyThrArgIleLysAlaLeuIleAsp

AspAlaValAlaLysGlyAlaArgLeuValIleGlyGlyGlnLeuGluGlySerIleLeu

GlnProThrLeuLeuAspGlyValAspAlaSerMetArgLeuTyrArgGluGluSerPhe

GlyProValAlaValValLeuArgGlyGluGlyGluGluAlaLeuLeuGlnLeuAlaAsn

AspSerGluPheGlyLeuSerAlaAlaIlePheSerArgAspThrGlyArgAlaLeuAla

-continued
```
LeuAlaGlnArgValGluSerGlyIleCysHisIleAsnGlyProThrValHisAspGlu

AlaGlnMetProPheGlyGlyValLysSerSerGlyTyrGlySerPheGlyGlyLysAla

SerIleGluHisPheThrGlnLeuArgTrpValThrLeuGlnAsnGlyProArgHisTyr

ProIle
``` or a fragment or variant thereof.

The amino acid sequence is that given in FIG. 12 as that encoded by nucleotides 3804 to 5249.

As described in detail in the examples, this polypeptide sequence encodes an enzyme with vanillin:$NAD^+$ oxidoreductase activity from Ps. fluorescens biovar V., strain AN103.

By "variants" we include deletions, insertions and substitutions either conservative or non-conservative, where such changes may reduce or enhance the activity, or may not substantially alter the activity. In particular, the seventh aspect of the invention includes the complete polypeptide sequence of Ps. fluorescens biovar V, strain AN103 vanillin:$NAD^+$ oxidoreductase and this polypeptide itself.

By "conservative substitutions" is intended combinations such as Gly, Ala; Val, Ile, Leu; Asp, Glu; Asn, Gln; Ser, Thr; Lys, Arg; and Phe, Tyr. Such variants may be made using the methods of protein engineering and site-directed mutagenesis as described below and as is well known in the art.

A preferred embodiment of the invention is a polypeptide as defined in the fourth, fifth or sixth of the invention which is substantially pure.

By "substantially pure" we mean that the polypeptide is substantially free of other polypeptides, or other macromolecules, with which it is usually found in nature. Suitably, the polypeptide is substantially free of any other polypeptides or macromolecules. It is preferred if the polypeptide has less than 50% by weight of any other polypeptide, preferably less than 10%, more preferably less than 1%, still more preferably less than 0.1% and most preferably less than 0.01%.

Polypeptides can be purified using methods known in the art. It is preferred if the polypeptide is the product of a recombinant DNA.

A single polypeptide chain may comprise more than one of the enzyme activities (II) trans-feruloyl SCoA hydratase activity or (III) HMPHP SCoA cleavage activity.

Our data in the Examples shows that, in the case of Ps. fluorescens biovar. V, strain AN103, enzyme activities II and III are found in the same polypeptide chain, the sequence of which is given as the preferred polypeptides of the fifth and sixth aspects of the invention. Thus, when enzyme activities II and III are provided in any aspect of the invention it is most convenient if they are provided in the same polypeptide chain.

It will be appreciated that, using protein engineering methods or chemical cross-linking it may be possible to produce a single molecule which has enzyme activities II and III. Such a molecule, therefore, forms a further aspect of the invention.

An seventh aspect of the invention provides a polynucleotide encoding a polypeptide as defined in any one of the fourth, fifth or sixth aspects of the invention.

By "polynucleotide" we include RNA and DNA. DNA is preferred.

Thus, this aspect of the invention provides a polynucleotide which encodes any one of a polypeptide which has (II) trans-feruloyl SCoA hydratase activity; (III) HMPHP SCoA cleavage activity; (IV) vanillin:$NAD^+$ oxidoreductase activity; or a polypeptide which has more than one of these activities. Preferably the polynucleotide is derived from Ps. fluorescens biovar. V, strain AN103. A preferred polynucleotide comprises all or at least a part of the Ps. fluorescens DNA contained within the cosmid clone pFI793 as deposited under the Budapest Treaty at the National Collections of Industrial and Marine Bacteria Limited, AURIS Business Centre, 23 St Machar Drive, Aberdeen AB2 1RY, Scotland under Accession No NCIMB 40777, or a fragment or variant thereof.

The isolation of the cosmid clone pFI 793 is described in Example 5; pFI 793 includes DNA which encodes polypeptides which have enzyme activities II, III and IV. The cosmid clone pFI 793 itself, the genes contained in the Ps. fluorescens DNA thereof, and variants thereof form separate aspects of the invention.

A variant of a polynucleotide includes any insertion, deletion or substitution of the sequence which encodes a fragment or variant of a polypeptide as defined above.

For example, site-directed mutagenesis or other techniques can be employed to create single or multiple mutations, such as replacements, insertions, deletions, and transpositions, as described in Botstein and Shortle, Strategies and Applications of In Vitro Mutagenesis, *Science*, 229: 193–210 (1985), which is incorporated herein by reference. Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) of the invention can be used to obtain other DNA sequences that hybridise with it under conditions of high stringency. Such DNA includes any genomic DNA.

Accordingly, the polynucleotide of the invention includes DNA that shows at least 55 percent, preferably 60 percent, and most preferably 70 percent homology with the polynucleotide sequences identified in the invention, provided that such homologous DNA encodes a protein which is usable in the methods described herein.

DNA—DNA, DNA-RNA and RNA—RNA hybridisation may be, performed in aqueous solution containing between 0.1×SSC and 6×SSC and at temperatures of between 55° C. and 70° C. It is well known in the art that the higher the temperature or the lower the SSC concentration the more stringent the hybridisation conditions. By high stringency we mean 2×SSC and 65° C. 1×SSC is 0.15M NaCl/0.015M sodium citrate.

"Variants" of the polynucleotide include polynucleotides in which relatively short stretches (for example 20 to 50 nucleotides) have a high degree of homology (at least 50% and preferably at least 90 or 95%) with equivalent stretches of the polynucleotide of the invention even though the overall homology between the two polynucleotides may be much less. This is because important active or binding sites may be shared even when the general architecture of the protein is different.

A particularly preferred polynucleotide comprises the nucleotide sequence

```
ATGAGCACATACGAAGGTCGCTGGAAAACGGTCAAGGTCGAAATCGAAGACGGCATCGCG      (SEQ ID No 1)
TTTGTCATCCTCAATCGCCCGGAAAAACGCAACGCGATGAGCCCGACCCTGAACCGCGAG
ATGATCGATGTTCTGGAAACCCTCGAGCAGGACCCTGCCGCCGGTGTGCTGGTGCTGACC
GGTGCGGGCGAAGCCTGGACCGCAGGCATGGACCTCAAGGAATACTTCCGCGAAGTGGAC
GCCGGCCCGGAAATCCTCCAGGAAAAAATCCGCCGCGAAGCCTCGCAATGGCAATGGAAA
CTGCTGCGCATGTACGCCAAGCCGACCATCGCCATGGTCAATGGCTGGTGCTTCGGCGGC
GCTTTCAGCCCGCTGGTGGCCTGCGACCTGGCGATCTGCGCCGACGAAGCAACCTTCGGT
CTCTCGGAAATCAACTGGGGTATCCCCCCGGGCAACCTGGTGAGCAAGGCCATGGCCGAC
ACCGTGGGCCACCGCCAGTCGCTCTACTACATCATGACCGGCAAGACCTTCGGTGGGCAG
AAAGCCGCCGAGATGGGCCTGGTCAACGAAAGCGTGCCCCTGGCGCAACTGCGCGAAGTC
ACCATCGAGCTGGCGCGTAACCTGCTCGAAAAAAACCCGGTGGTGCTGCGTGCCGCCAAA
CACGGTTTCAAACGCTGCCGCGAACTGACCTGGGAGCAGAACGAGGATTACCTGTACGCC
AAGCTCGATCAGTCGCGTTTGCTGGACACCGAAGGCGGTCGCGAGCAGGGCATGAAGCAA
TTCCTCGACGACAAGAGCATCAAGCCTGGCCTGCAAGCGTAAACGC
```

(as given in FIG. 12, nucleotides 2872 to 5249) or a fragment or variant thereof.

This polynucleotide encodes HMPHP SCoA cleavage enzyme activity and a trans-feruloyl SCoA hydratase activity from Ps. fluorescens biovar. V, strain AN103 and encodes the preferred polypeptide of the fifth and sixth aspects of the invention.

A further particularly preferred polynucleotide comprises the nucleotide sequence

```
ATGCTGGACGTGCCCCTGCTGATTGGCGGCCAGTCGTGCCCCGCGGCGCGACGGTCGAAC    (SEQ ID No 3)
CTTCGAGCGCCGCAACCCGGTGACTGGCGAGTTGGTGTCGCGGGTTGCCGCCGCCACCCT
GGAAGATGCCGACGCCGCCGTGGCCGCTGCCCAGCAAGCGTTTCCCGCGTGGGCCGCGCT
GGCGCCCAATGAACGGCGCAGCCGTTTGCTCAAGGCCGCCGAACAATTGCAGGCGCGCAG
CGGCGAGTTCATCGAGGCGGCGGGCGAGACCGGCGCCATGGCCAACTGGTACGGCTTCAA
CGTACGGCTGGCGGCCAACATGCTGCGTGAAGCGGCATCGATGACCACCCAGGTCAATGG
TGAAGTGATTCCCTCGGACGTTCCCGGCAGTTTCGCCATGGCCCTGCGCCAGCCCTGTGG
CGTGGTGCTGGGCATCGCCCCCTGGAACGCCCCGGTGATTCTCGCCACCCGGGCGATTGC
CATGCCGCTGGCCTGTGGCAACACCGTGGTGCTGAAGGCTCCGAGCTGAGTCCGGCGGTG
CATCGCTTGATCGGCCAGGTGCTGCAGGACGCCGGCCTGGGCGATGGCGTGGTCAACGTC
ATCAGTAATGCGCCGGCGGATGCGGCACAGATTGTCGAGCGCCTGATTGCCAACCCGGCC
GTACGCCGGGTCAATTTCACCGGTTCGACCCACGTCGGGCGCATTGTCGGCGAGCTCTCG
GCGCGCCACCTCAAACCGGCGTTGCTCGAGCTGGGCGGCAAGGCACCGTTGCTGGTGCTC
GATGATGCCGACCTGGAGGCTGCCGTGCAGGCGGCGGCGTTTGGCGCCTACTTCAACCAG
GGACAGATCTGTATGTCCACCGAGCGCCTGATTGTCGATGCCAAGGTGGCCGACGCCTTT
GTCGCCCAGTTGGCGGCCAAGGTCGAGACCCTGCGCGCCGGTGATCCTGCCGACCCGGAG
TCGGTGCTCGGTTCGCTGGTGGACGCCAGCGCTGGCACGCGGATCAAAGCGTTGATCGAT
GATGCCGTGGCCAAGGGCGCGCGCCTGGTAATCGGCGGGCAACTGGAGGGCAGCATCTTG
CAGCCGACCCTGCTCGACGGTGTCGACGCGAGCATGCGTTTGTACCGCGAAGAGTCCTTC
```

```
                         -continued
GGCCCGGTGGCGGTGGTGCTGCGCGGCGAGGGCGAAGAAGCGCTGTTGCAACTGGCCAAC

GACTCCGAGTTCGGTTTGTCGGCGGCGATTTTCAGTCGTGACACCGGCCGTGCCCTGGCC

CTGGCCCAGCGGGTCGAATCGGGCATCTGCCACATCAACGGCCCGACCGTGCACGACGAA

GCGCAAATGCCTTTTGGCGGGGTCAAGTCCAGCGGCTACGGCAGTTTTGGCGGCAAGGCA

TCGATTGAGCATTTCACTCAGTTGCGCTGGGTCACCCTCCAGAATGGTCCACGGCACTAT

CCGATC
```

(as given in FIG. 12, nucleotides 3804 to 5249) or a fragment or variant thereof. This polynucleotide encodes the polypeptide sequence of the sixth aspect of the invention. It is particularly convenient to isolate the whole gene from cosmid clone pFI 793 as deposited under the Budapest Treaty at NCIMB under Accession No NCIMB 40777.

The polynucleotides of the invention are all readily isolated from pFI 793 by probing with the given sequences or parts thereof, or by other methods known in the art, and the nucleotide sequences can be confirmed by reference to the deposited cosmid (pFI 793).

It will be appreciated that fragments and variants of the polynucleotides of the invention can readily be made by the person skilled in the art using standard molecular biological methods such as those described in Sambrook et al "Molecular Cloning, a laboratory manual", (1989), (2nd Edition), Cold Spring Harbor Laboratory Press, Cold Spring Harbor, N.Y. The whole gene and variants and fragments thereof are specifically included in this aspect of the invention.

It is preferred if the polynucleotide, conveniently DNA, is joined to a nucleic acid vector.

DNA constructs of the invention may be purified from the host cell using well known methods.

For example, plasmid vector DNA can be prepared on a large scale from cleaved lysates by banding in a CsCl gradient according to the methods of Clewell & Helinski (1970) *Biochemistry* 9, 4428–4440 and Clewell (1972) *J. Bacteriol.* 110, 667–676. Plasmid DNA extracted in this way can be freed from CsCl by dialysis against sterile, pyrogen-free buffer through Visking tubing or by size-exclusion chromatography.

Alternatively, plasmid DNA may be purified from cleared lysates using ion-exchange chromatography, for example those supplied by Qiagen (Chatsworth, Calif., USA). Hydroxyapatite column chromatography may also be used.

The DNA is then expressed in a suitable host to produce a polypeptide of the invention. Thus, a DNA encoding a polypeptide of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued Apr. 3, 1984 to Rutter et al, 4,530,901 issued Jul. 23, 1985 to Weissman, 4,582,800 issued Apr. 15, 1986 to Crowl, 4,677,063 issued Jun. 30, 1987 to Mark et al, 4,678,751 issued Jul. 7, 1987 to Goeddel, 4,704,362 issued Nov. 3, 1987 to Itakura et al, 4,710,463 issued Dec. 1, 1987 to Murray, 4,757,006 issued Jul. 12, 1988 to Toole, Jr. et al, 4,766,075 issued Aug. 23, 1988 to Goeddel et al, and 4,810,648 issued Mar. 7, 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention may then be cultured for a sufficient time and under appropriate conditions known to those skilled in the art in view of the teachings disclosed herein to permit the expression of the polypeptide, which, if desirable, can then be recovered.

Many expression systems are known, including bacteria (for example *Escherichia coli* and *Bacillus subtilis*), yeasts (for example *Saccharomyces cerevisiae*), filamentous fungi (for example Aspergillus), plant cells and whole plants, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli* transformed therewith.

Several promoters are available to direct transcription of bacterial and other heterologous genes in plants. In particular, these include the 35S promoter of cauliflower mosaic virus (CaMV 35S), the ribulose bisphosphate carboxylase small subunit promoter and the Agrobacterium T-DNA octopine synthase and manopine synthase promoters. These promoters have been widely used, for example, in conjunction with bacterial genes conferring herbicide resistance (see D. M. Stalker, ibid., pp 82–104). These promoters do not confer any specificity of gene expression at the organ, tissue or organellar levels, or responsiveness of gene expression to environmental influences such as light.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps)

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'–5'-exonucleolytic activities, and fill in recessed 3'-ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a polynucleotide vector construct of the present invention. The host cell can be either prokaryotic or eukaryotic and it may be comprised in a multicellular organism such as a plant. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and plant cells. Yeast host cells include YPH499, YPH500 and YPH501 which are generally available from Stratagene Cloning Systems, La Jolla, Calif. 92037, USA. Preferred plant host cells and plants include those from *Nicotiana* spp., *Solanum tuberosum* (potato), *Brassica* spp. (eg oil seed rape), *Beta* spp. (eg sugar beet, leaf beet and beetroot), *Capsicum* spp. and *Vanilla* spp.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual,* Cold Spring Harbor Laboratory, Cold Spring Harbor, N.Y. Transformation of yeast cells is described in Sherman et al (1986) *Methods In Yeast Genetics, A Laboratory Manual,* Cold Spring Harbor, N.Y. The method of Beggs (1978) *Nature* 275, 104–109 is also useful. With regard to plant cells and whole plants three plant transformation approaches are typically used (J. Draper and R. Scott in D. Grierson (ed.), "Plant Genetic Engineering", Blackie, Glasgow and London, 1991, vol. 1, pp 38–81):

i) Agrobacterium-mediated transformation, using the Ti plasmid of *A. tumefaciens* and the Ri plasmid of *A. rhizogenes* (P. Armitage, R. Walden and J. Draper in J. Draper, R. Scott, P. Armitage and R. Walden (eds.), "Plant Genetic Transformation and Expression—A Laboratory Manual", Blackwell Scientific Publications, Oxford, 1988, pp 1–67; R. J. Draper, R. Scott and J. Hamill ibid., pp 69–160);

ii) DNA-mediated gene transfer, by polyethylene glycol-stimulated DNA uptake into protoplasts, by electroporation, or by microinjection of protoplasts or plant cells (J. Draper, R. Scott, A. Kumar and G. Dury, ibid., pp 161–198);

iii) transformation using particle bombardment (D. McCabe and P. Christou, *Plant Cell Tiss. Org. Cult.,* 3, 227–236 (1993); P. Christou, *Plant J.,* 3, 275–281 (1992)).

Agrobacterium-mediated transformation is generally ineffective for monocotyledonous plants (eg Vanilla), for which approaches ii) and iii) are therefore preferred. In all approaches a suitable selection marker, such as kanamycin- or herbicide-resistance, is preferred or alternatively a screenable marker ("reporter") gene, such as β-glucuronidase or luciferase (see J. Draper and R. Scott in D. Grierson (ed.), "Plant Genetic Engineering", Blackie, Glasgow and London, 1991, vol. 1 pp 38–81).

Electroporation is also useful for transforming cells and is well known in the art for transforming yeast cell, bacterial cells and plant cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5×PEB using 6250 V per cm at 25 μFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium; and also, in the case of plant cells, a plant derived from, and containing, such cells.

It is particularly preferred if the host cell comprises a nucleic acid which encodes any one of, or combination of, a polypeptide which, in the presence of appropriate cofactors if any is capable of catalysing the interconversion of trans-feruloyl SCoA and 4-hydroxy-3-methoxyphenyl-β-hydroxypropionyl SCoA (HMPHP SCoA) or a polypeptide which, in the presence of appropriate cofactors if any, is capable of catalysing the interconversion of 4-hydroxy-3-methoxyphenyl-β-hydroxypropionyl SCoA (HMPHP SCoA) and vanillin.

It will be appreciated that the host cells of the invention or an extract thereof are particularly suited for use in the methods of the invention. It is particularly preferred if the host cell does not contain means for converting vanillin to a non-vanillin product.

It is most preferred if the host cell is a plant cell or is comprised in a whole plant or a bacterial cell or a yeast cell. Preferred bacterial hosts include lactic acid bacteria such as Lactococcus spp. and Lactobacillus nspp. Preferred yeast hosts include *Saccharontyces cerevisiae* and its biovars. It is particularly preferred if the host cell is a food-grade host cell (for example a microorganism which is used or can be used in the food or beverage industry). It is also preferred if the plant is an edible plant.

It will be appreciated that some host cells or host organisms may already contain enzyme activities I, II, III or IV and, in that case, it may be sufficient, in order to use the host cells in the methods of the invention, to introduce into said host cell or host organism one or more polynucleotides which encode enzyme activities II, III or IV which encode those enzyme activities which are deficient in the host cell or host organisms.

In the case of plants for use in the methods of the invention, it is preferred that the relevant gene expression is directed to target organs, tissues and subcellular organelles where trans-feruloyl SCoA, or other appropriate substrates (eg 4-trans-coumaroyl SCoA or trans-caffeoyl ScoA) for the enzymes encoded by the transferred genes, are most readily available. The stage at which thioesterification with CoASH occurs in plants, in relation to the progressive substitution of the phenyl ring which takes place during the conversion from trans-cinnamate to trans-ferulate, is unclear and may be variable (see R. Whetten and R. Sederoff, *The Plant Cell,* 7, 1001–1013 (1995)). The subcellular localisation or distribution of these intermediates during plant phenylpropanoid metabolism also remains uncertain; it is likely that they are cytosolic, or that some functional organisation of the enzymes which metabolise them occurs. The concept of the metabolic cluster or "metabolon", in which there is a degree of metabolic channelling and free diffusion is restricted, has been proposed and discussed (see R. A. Dixon and N. L. Paiva, *The Plant Cell,* 7, 1085–1097 (1995) and Ioc cit.).

Trans-ferulate, 4-trans-coumarate and trans-caffeate are normal metabolic intermediates. Thus, there may be no requirement to manipulate host plants in order to provide trans-feruloyl SCoA. Their concentrations are expected to be influenced in varying degrees by physiological requirements for a wide range of end-products of the phenylpropanoid pathway, including for example lignin, coumarins and flavonoids. There is some evidence that the activity of the first enzyme of the phenylpropanoid pathway, phenylalanine ammonia lyase (PAL: EC 4.3.1.5), can influence the accumulation of end-products of the pathway (N. Bate, J. Orr, W. Ni, A. Meromi, T. Nadler-Hassar, P. W. Doerner, R. A. Dixon, C. J. Lamb and Y. Elkind, *Proc. Natl. Acad. Sci. USA,* 91, 7608–7612 (1994)) so under certain circumstances it is possible to enhance the metabolic effects of the expression of the genes for enzyme activities II, and III by increasing the expression of PAL.

It is well known that gene expression in the phenylpropanoid pathway is responsive to a range of environmental and stress factors, including wounding, chemical elicitors of pathogenic origin, and u/v light. The mechanisms regulating these responses are not very well understood, though several transcription factors have been identified (see R. A. Dixon and N. L. Paiva, The Plant Cell, 7, 1085–1097 (1995)). However, particularly when these are more fully characterised, they do or will offer opportunities for predictable and inducible control of gene expression, particular to enhance the provision of substrate.

Thus, a further aspect of the invention provides a transgenic plant comprising a polynucleotide according to any of the fourth or fifth aspects of the invention. In other words, the transgenic plant is genetically engineered to encode and, preferably, express any one or more of enzyme activities II or III. It is particularly preferred that, following said genetic engineering the plant is able to produce vanillin from trans-feruloyl SCoA. It will be appreciated that, depending on the enzymes present in the host plant, it may be necessary only to provide a gene encoding only a single of said enzyme activities or it may be necessary to provide a gene or genes of any two of said enzyme activities.

Conveniently, the transgenic plant is genetically engineered to encode and, preferably, express enzyme activities II and III. It can be readily seen that the transgenic plants of this aspect of the invention may be used in the methods of producing vanillin of the invention, especially when the plant provides the enzyme activity that interconverts trans-ferulic acid or a salt thereof and trans-feruloyl SCoA.

Preferably the plant is a plant which is readily transformed. Preferably the plant is a plant which is commonly used in agriculture or horticulture and more preferably the plant is an edible plant. Advantageously the plant is a plant in which it is desirable to introduce a vanilla flavour or aroma.

Preferred plants include those selected from Nicotiana spp., *Solanum tuberosum,* Brassica spp., Capsicum spp., Beta spp. and Vanilla spp.

As is described in more detail below the plant may be eaten or may be processed into a foodstuff or beverage.

Thus, conveniently the transgenic plant is processed or prepared so that it is not capable of reproduction or cultivation, for example the transgenic plant is harvested from the environment in which it was grown.

When vanillin (or the desirable products such as p-hydroxybenzaldehyde) is produced in a host cell or organism of the invention, especially if it is produced in a transgenic plant of the invention, the vanillin or desirable product may initially be present in the form of a glycoside, more particularly, a β-D-glycoside, or, in the case of a carboxylic acid, as esters of β-D-glucose (as occurs in Vanilla pod). In this case, it is desirable to release the vanillin (and desirable product) into its uncombined form, for example by acid- or base-catalysed hydrolysis or by the use of glycosides such as the β-D-glucosidase (emulsin; S. Hestrin, D. S. Femgold and M. Schramm, *Meth. Enzymol. I,* 231–257 (1955); see also D. Chassagne, C. Bayonore, J. Crouzet and K. Baumes in "Bioflavour 95", eds. P. Étiévant and P. Schreier, INRA, Paris, pages 217–222 (1995).).

In relation to the use of a microorganism such as *Ps. fluorescens* biovar V, strain AN103 or of a microorganism which has been genetically modified to contain enzyme activities II and III (or at least those of these activities that it does not normally have), it is preferred that said microorganism is provided with trans-feruloyl SCoA or a means to provide said CoA thioester from trans-fernlic acid or a salt thereof at least in its culture medium.

Thus, it can be seen from all of the foregoing description that the invention includes biochemical and fermentative processes for producing vanillin and vanillic acid, recombinant or transgenic plants and the use of the said plants in a method of making vanillin or vanillic acid.

Typically, in a biochemical process the strain of Pseudomonas (eg *Ps. fluorescens* biovar. V, strain AN 103) provides an enzyme system for the biotransformation of plant derived trans-ferulic acid to vanillin and/or related compounds. Enzyme preparations, whole cells of Pseudomonas or a heterologous host organism expressing appropriate Pseudomonas genes may be used for this. A variety of mutants of Pseudomonas and various additional enzyme preparations, co-factors or co-factor regenerating systems may be used. The Pseudomonas enzymes might be overexpressed in a heterologous host before being extracted and used in a biotransformation.

Alternatively, but suitably, some form of fermentation process may be used which involves the Pseudomonas strain or an appropriate derived mutant or a heterologous host organism in which the genes for biotransformation are expressed. The chosen microorganism is typically grown on a ferulate-rich substrate or a substrate comprising trans-feruloyl SCoA. This could generate a vanillin production process.

In addition the invention includes recombinant microorganisms (eg lactic acid bacteria) which are modified to contain genes encoding enzyme activities II and III. For example, lactic acid bacteria modified according to the invention may be used to produce vanilla-flavoured yoghurt provided that they are supplied with trans-feruloyl SCoA.

Advantageously, genes for vanillin production (such as those encoding enzyme activities II and III) are expressed in a variety of plant species such that vanillin accumulates in an appropriate tissue. In this case a new crop plant may be cultivated and vanillin would be extracted. Thus, a sugar beet plant may be made according to the invention in which the beet was rich in vanillin. In addition the development of a novel plant cultivars for direct consumption (eg vanilla-flavoured capsicum), or even for their desirable aroma properties, included in the invention.

The polypeptides of the invention, or the genes which encode them, may be used either individually or in combination (whether as substantially isolated polypeptides, or in cell-free extracts or as host cells or organisms which encode and, preferably, express said polypeptides) to convert a compound into a desirable product. Certain compounds and desirable products have been described above. However, the invention also includes the production of any other desirable product, such as a flavour or aroma, from substrates related to trans-ferulate and other known substrates of the polypeptides (enzymes) of the invention. Thus, the polypeptides or genes of the invention, either individually or in combination, may be used in processes for converting, for example, synthetic substrates of the said polypeptides (enzymes) into novel flavours and aromas or they may be used to modify the chemical profile of known flavours or aromas.

Similarly, it will be appreciated that certain desirable products can be made by the further action of enzyme activity IV upon certain compounds, particularly those produced by enzyme activities I, II and III. For example, enzymes activities I, II and III may be used to convert trans-4-coumaric acid or trans4-coumaroyl SCoA to p-hydroxybenzaldehyde and enzyme activity IV may then be used to convert p-hydroxybenzaldehyde to p-hydroxybenzoic acid. Thus, the invention includes a method of producing p-hydroxy-benzoic acid using at least one of enzyme activities I, II, III and IV and advantageously using all of them.

A further aspect of the invention provides a food or beverage comprising a host cell comprising a polynucleotide of the invention, or an extract of said host cell. The host cells comprising one or more polynucleotides of the invention, especially those such host cells which produce vanillin by virtue of the presence of said polynucleotide or polynucleotides, may be used in the production of food or beverages. In particular, as discussed above, lactic acid bacteria which produce vanillin by the methods of the invention may be used in the production of cheese, yogurt and related products including milk drinks. Similarly, yeasts which produce vanillin by the methods of the invention may be used in the production of food and beverages such as bread and beer. Extracts of said host cells may also be used in the food or beverage industry.

A still further aspect of the invention provides a food or beverage comprising a transgenic plant comprising a polynucleotide of the invention, or a part or extract or said transgenic plant. The transgenic plant comprising one or more polynucleotides of the invention, especially those such transgenic plants which produce vanillin by virtue of the presence of said polynucleotide or polynucleotides, may constitute the food itself or they may be processed to form the food or beverage. For example, a tuber of a transgenic potato of the invention constitutes a food of this aspect of the invention. Alternatively, said transgenic potato may be processed into another foodstuff which is, nevertheless, a food of this aspect of the invention.

Still further aspects of the invention provide use of *Pseudomonas fluorescens* biovar. V, strain AN103 or a mutant or derivative thereof in a method for producing vanillin, or vanillic acid or salt thereof; use of a polypeptide of the invention in a method for producmg vanillin, or vanillic acid or salt thereof; use of a polynucleotide of the invention in a method for producing vanillin, or vanillic acid or salt thereof; and use of a host cell of the invention in a method for producing vanillin or vanillic acid or a salt thereof.

As is clear from the foregoing the invention also includes a method of producing vanillin or vanillic acid, or other related products, the method comprising providing trans-feruloyl SCoA (or any other suitable CoASH thioester which can be acted upon by enzyme activity II) and providing enzyme activity II, enzyme activity III and, in the case of vanillic acid production or another related product, enzyme activity IV. Trans-feruloyl SCoA is obtainable by the method described in Example 2 or it may be obtained using the methods of Zenk et al (1980) *Anal. Biochem.* 101, 182–187, incorporated herein by reference. Other CoASH thioesters which may be substrates for enzyme II are also described in Zenk et al.

The preferred method steps and organisms for use in the methods, and the foods and beverages of the earlier aspects of the invention are also preferred in this method of the invention to the extent that they are compatible with this method, and the organisms used in this method.

As is discussed above, trans-feruloyl SCoA (and related CoASH thioesters such as 4-trans-coumaroyl SCoA and trans-caffeoyl SCoA) are normal metabolic intermediates in plants. Thus, a transgenic plant which comprises a polynucleotide or polynucleotides which encode, and preferably express, enzyme activities II and III in a location in the plant which contains trans-feruloyl SCoA or other suitable CoASH thioester is particularly suited for the purposes of this aspect of the invention. As is described above, such transgenic plants and products derived therefrom form part of the invention.

The invention will now be described in more detail with reference to the following Examples and Figures wherein:

FIG. 1 describes the vanillin pathway in *Pseudomonas fluorescens* biovar. V, strain AN103. HMPHP SCoA is 4-hydroxy-3-methoxy-phenyl-β-hydroxypropionyl SCoA. I is an enzyme that catalyses the interconversion of trans-ferulic acid and trans-feruloyl SCoA; II is an enzyme that catalyses the interconversion of trans-feruloyl SCoA and HMPHP SCoA; III is an enzyme that catalyses the interconversion of HMPHP SCoA and vanillin; and IV is an enzyme that catalyses the interconversion of vanillin and vanillic acid.

FIG. 2 illustrates the growth of strain AN103 following transfer to MM medium containing 10 mM vanillate (V), 10 mM trans-ferulate (F) or 10 mM trans-ferulate plus 10 mM vanillate (FV). Cultures were previously grown in MM medium containing 10 mM vanillate.

FIG. 3 indicates the changes in trans-ferulate and vanillate concentrations during growth of strain AN 103 on MM medium containing 10 mM trans-ferulate.

FIG. 4 shows the production of vanillin (van) and vanillate (VA) by an extract of cells of strain AN103 (165 μg protein) incubated with trans-ferulate, ATP, CoASH and $Mg^{2+}$ ions, both in the absence of $NAD^+$ and in its presence (0.5 mM). Cells were grown in the presence of 10 mM trans-ferulate, plus 10 mM vanillate.

FIG. 5 demonstrates the formation of feruloyl SCoA, vanillin and acetyl SCoA from trans-ferulate supplied to a PD10-treated extract of trans-ferulate-grown cells of strain AN 103 (7 kg protein) in the presence of ATP, CoASH and $Mg^{2+}$ ions.

FIG. 6 demonstrates the production of vanillin, acetyl SCoA and feruloyl SCoA from HMPHP SCoA supplied to a PD10-treated cell-free extract (7 μg protein) of trans-ferulate-grown cells of strain AN103.

FIG. 7 shows the induction over time of trans-ferulate:CoASH ligase activity in response to 10 mM trams-ferulate (F), 10 mM vanillate (V) and 10 mM trans-ferulate plus 10 mM vanillate (FV) present in MM medium. The inocula were grown in MM medium plus 10 mM vanillate;

growth conditions, enzyme extraction and assay were as described in Examples 1 and 2.

FIG. 8 shows SDS-PAGE of A), an extract of cells grown in MM medium with 10 mM trans-ferulate, electrophoresed at successive stages of purification of the HMPHP SCoA cleavage enzyme; successive stages are Crude Extract, Mono Q-purified, Mono-P-purified and Phenyl Superose-purified, and B), extracts of cells grown in MM medium with either 10 mM vanillate or 10 mM trans-ferulate and electrophoresed alongside Mono-P-purified cleavage enzyme; A) silver-stained; B) Coomassie-stained.

FIG. 9 shows EcoRI/PstI digests of cosmid clones pFI793, pFI794, pFI795 and pFI796 separated on an agarose gel.

FIG. 10 shows the sequence of the redundant primers designed from 20 N-terminal amino residues of the 31-kDal protein (SEQ ID Nos. 5 and 6).

FIG. 11 shows a Southern blot of EcoRI/PstI digests of various cosmid clones probed with the PCR product amplified using the N-terminal degenerate oligonucleotide primers as shown in FIG. 10.

FIG. 12 shows the nucleotide sequence of pFI989 (ie the 4370 bp EcoRI/PstI fragment from pFI794), together with the succeeding 882 bp determined from a further subclone, pFI1056 and from pFI794 itself (SEQ ID No 7). The amino acid sequence of the 31 kD protein and that corresponding to the succeeding open reading frame encoding vanillin:$NAD^+$ oxidoreductase (vanillin dehydrogenase) (SEQ ID Nos. 2 and 4) are also shown.

FIG. 13 shows the nucleotide sequence of pFI901 (ie the 1.8 kb EcoRI/PstI fragment from pFI793) (SEQ ID No 8).

FIG. 14 shows the nucleotide sequence of pFI911 (ie the 850 bp EcoRI/PstI fragment from pFI793) (SEQ ID No 9).

FIG. 15 shows the nucleotide sequence of pFI912 (ie the 958 bp EcoRI/PstI fragment from pFI793) (SEQ ID No 10).

FIG. 16 shows the nucleotide sequence of pFI913 (ie the 959 bp EcoRI/Psd fragment from pFI793) (SEQ ID No 11).

FIG. 19 shows the nucleotide sequence of the merged contigs pFI913/PCR product/pFI901 (4259 bp) (SEQ ID No 12).

EXAMPLE 1

Figure 1:
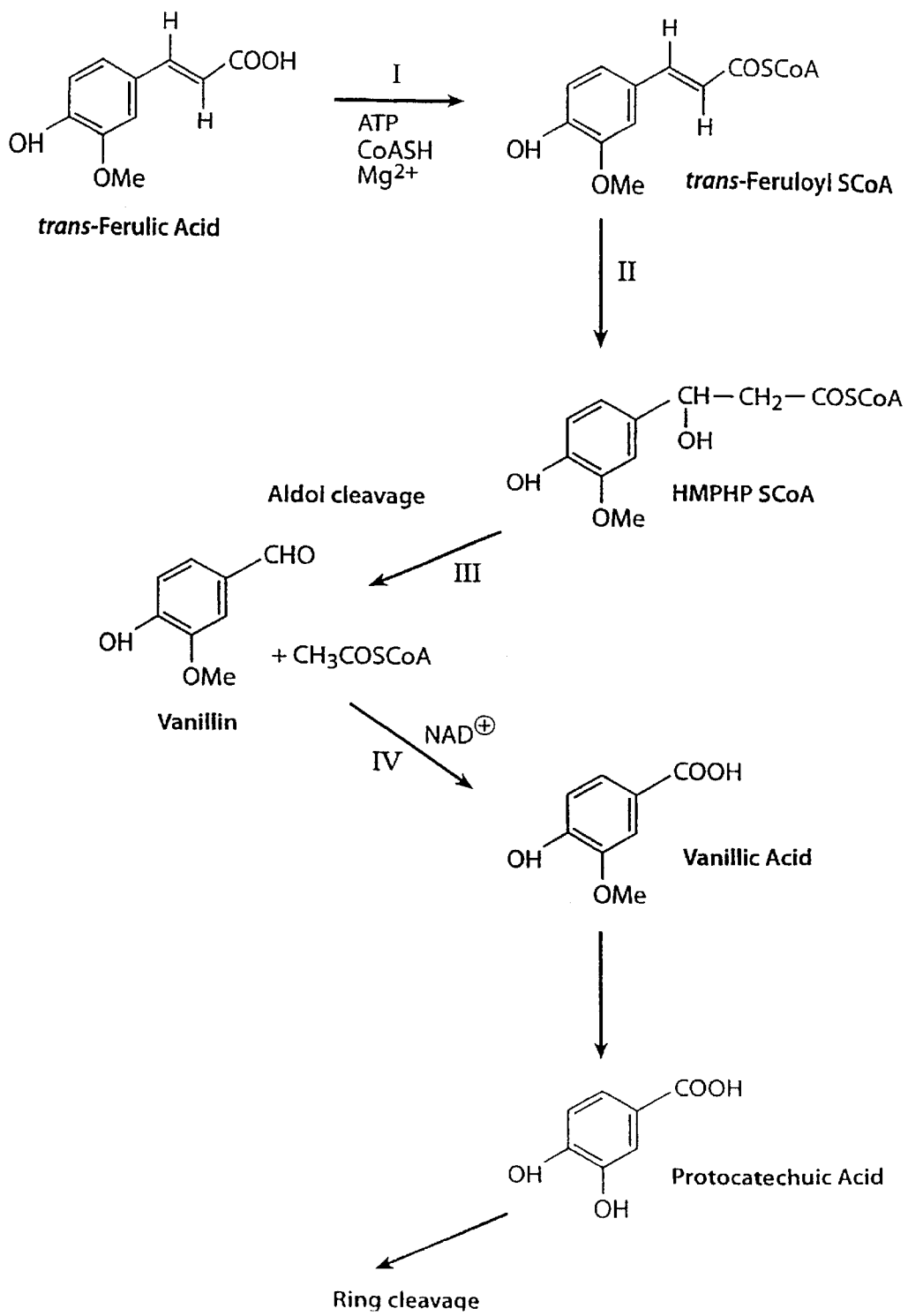

Isolation and growth of *Pseudomonas fluorescens* biovar. V. strain AN103

Experimental

Growth media

Organisms were grown on the following media:

Minimal Medium (MM) contained, per 1: $KH_2PO_4$, 5 g; $(NH_4)_2SO_4$, 1 g; $FeSO_4$, 0.5 mg; $CaCl_2$, 0.5 mg; $MnCl_2.5H_2O$, 5 mg; $(NH_4)_6Mo_2O_7.4H_2O$, 1.1 mg; $MgSO_4$, 5 mg; EDTA, 50 mg; $ZnSO_4.7H_2O$, 28 mg; $CuSO_4.5H_2O$, 1.6 mg; $CoCl_2.6H_2O$, 1.6 mg. The pH was 7.0. Carbon sources were included as indicated.

Tryptone- and yeast-based medium (LBMod) contained, per l: tryptone (Bacto; Difco, Detroit, USA), 10 g; yeast extract (Bacto), 5 g; NaCl, 10 g. The pH was adjusted to 7.5. LB Medium was identical with LB Mod, with the addition of glucose (1 g/l).

Solid media were prepared with the addition of agar (Difco), 15 g/l.

Isolation of *Pseudomonas fluorescens* biovar. V, strain AN,103

The organism was isolated from surface soil, on the basis of ability to grow on trans-ferulate as sole carbon source. Initially, a Ig soil sample was added to 100 ml sterile Minimal Medium (MM), containing trans-ferulic acid (10 mM). After 2 weeks at 25° C., with shaking at 200 rpm, a sample (100 µl) was removed and added to 200 ml of fresh medium containing 10 mM trans-ferulic acid; this was repeated twice. Serial dilution onto solid medium (MM) containing 10 mM trans-ferulate as sole carbon source enabled isolated colonies to be obtained which were replica-plated onto MM plates containing individual substrates as carbon sources. Several strains able to use trans-ferulate as sole carbon source were isolated—one (AN103), which was capable of growing also on vanillin, was selected for further work.

Growth of strain AN103

The organism was grown routinely at 25° C. on MM, with shaking, using vanillic acid (10 mM) or trans-ferulic acid (10 mM) as sole carbon source; 50 ml of medium was used in a 250 ml Erlenmeyer flask. Growth was monitored by measuring absorbance at 550 or 600 nm.

For long-term storage, bacteria from logarithmic-phase cultures were centrifuged and then resuspended in Minimal Medium (MM) containing 50% glycerol. They were then stored at −70° C. Cultures from these frozen stocks were reinitiated by transfer onto LB or LB-MOD solid medium, followed by inoculation into liquid medium containing 10 mM trans-ferulic acid.

Results

Figure 2:
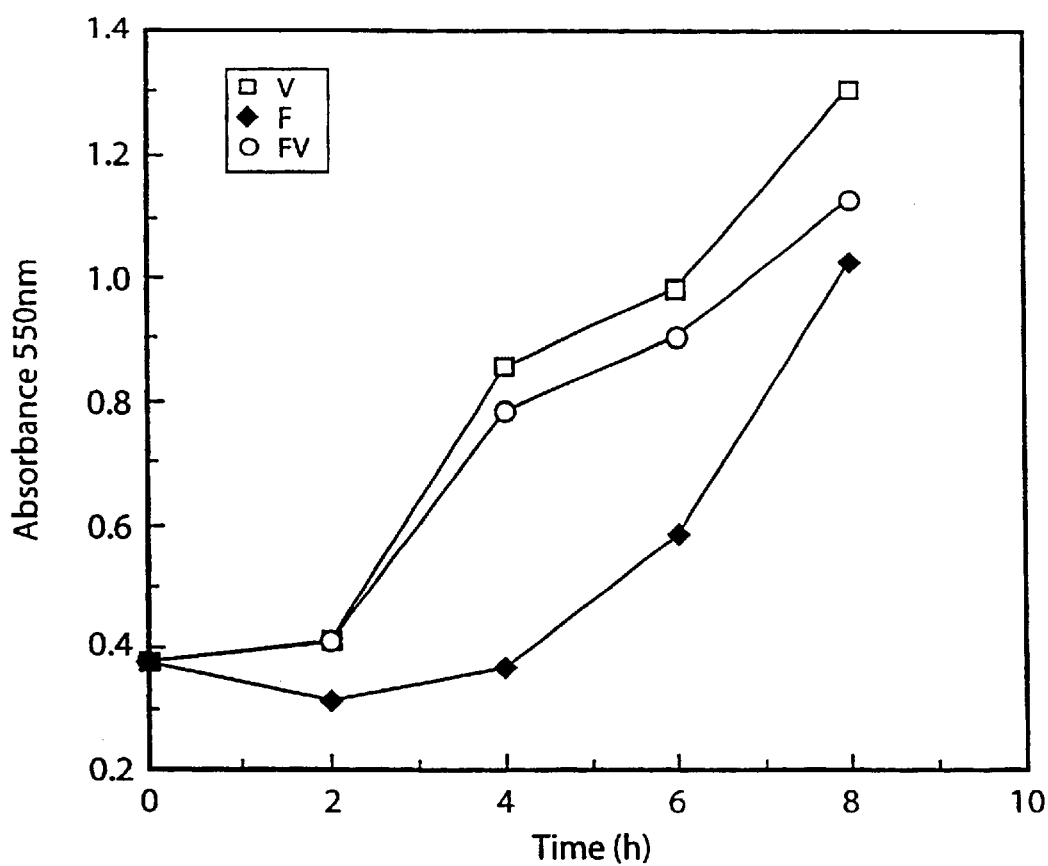
Figure 3:
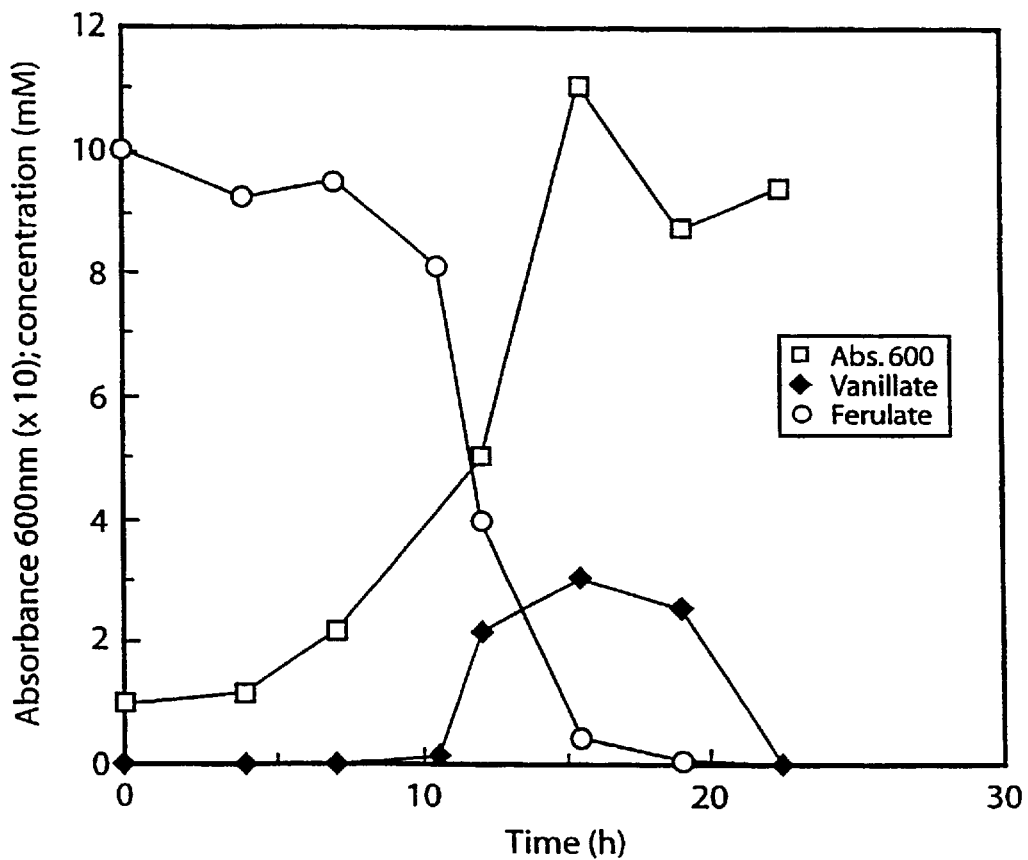

The organism was isolated from soil samples rich in decayed vegetation and was shown to be a strain of *Pseudomonas fluorescens* using standard identification techniques. As shown in Table I, the bacterium would grow not only on trans-ferulate as sole carbon source, but also on several closely-related compounds, including vanillate, protocatechuate and caffeate. Growth on vanillin was observed at low concentrations (<1 mM) but was variable; higher concentrations were growth-inhibitory. If the organism was grown on vanillate, transfer to medium containing trans-ferulate as sole carbon source was followed by a lag in the growth curve; this was not observed if the transfer was to medium containing both vanillate and trans-ferulate (FIG. 2). During a growth cycle on trans-ferulate, a transient increase in vanillate was observed at around the time when trans-ferulate disappearance was maximal (FIG. 3), suggesting that vanillate was a catabolite of trans-ferulate. A small amount of protocatechuate was also observed when the culture medium was examined by TLC (not shown).

TABLE I

Relative growth of *Ps. fluorescens* biovar. V, strain AN103 on a range of carbon substrates
Subtrates were provided on MM Medium at 10 mM concentration (vanillin, 1 mM) and relative growth after 48 h at 25° C. was monitored by measuring absorbance at 600 nm.

| Substrates | Relative Growth (%) |
| --- | --- |
| Ferulic acid | 100 |
| Caffeic acid | 79 |
| Sinapic acid | 0 |
| Cinnamic acid | 0 |
| Vanillin | <100 |
| Vanillic acid | 140 |
| Protocatechuic acid | 77 |
| Protocatechuic aldehyde | 0 |
| Glucose | 221 |
| Acetate | 47 |
| Methanol | 0 |

EXAMPLE 2

Trans-ferulate metabolism in cell-free extracts and mechanism of cleavage

Experimental

Chemicals

Chemicals and biochemicals were routinely obtained from Sigma Chemical Co. Ltd, Poole, Dorset, UK, Aldrich Chemical Co. Gillingham, Dorset, UK or BDH-Merck, Poole, Dorset, UK. The synthesis, of CoASH thioesters is described below.

Preparation of 4-hydroxy-3-methoxyphenyl-β-hydroxypropionyl SCoA (HMPHP SCoA)

This compound was prepared starting from a Reformatsky condensation of vanillin with ethyl bromoacetate (see R. L. Shriner, The Reornatsky Reaction in "Organic Reactions", R. Adams, W. E. Bachmann, L. F. Fieser, J. R. Johnson and H. R. Snyder, eds., vol. 1, pp 1–37, John Wiley, New York [1942]), followed by purification of the resulting ethyl 4-hydroxy-3-methoxyphenyl-β-hydroxypropionate (ethyl HMPHP) by HPLC, hydrolysis to the free acid, N-succinimidylation and, finally, exchange of the N-succinimidyl group with CoASH and isolation of the CoASH thioester by preparative TLC (see V. Semler, G. Schmidtberg and G. G. Gross, Z. *Naturforsch.* 42 c, 1070–1074 [1987]).

Vanillin (3 g) was mixed with 1.9 ml of ethylbromoacetate and 2 g of dry Zn dust in 60 ml of dry 1,4-dioxane in a round-bottomed flask fitted with drying tubes and a reflux condenser. The reaction mixture was heated gently to boiling using a heating mantle and refluxed gently for ca. 1 h. After being allowed to cool, the mixture was acidified with 60 ml of 10% $H_2SO_4$ and extracted with 4×120 ml of diethyl ether. The combined ether phases were dried with anhydrous $Na_2SO_4$ and unreacted vanillin was removed by washing with 3×100 ml of sat. $K_2S_2O_5$. The ether phase was then rotary evaporated under vacuum at ca. 30° C. to remove the ether, leaving a liquid residue (ca. 10 ml). This was then applied to a preparative C-18 reverse-phase HPLC column (Dynamax 60A, 8 µm, 250 mm×41 mm; Rainin, Woburn, Mass., USA) and eluted at 12 ml min$^{-1}$ with a gradient of MeOH/$H_2O$, containing 1 mM trifluoroacetic acid. [Solvent A comprised 40% MeOH/1 mM trifluoroacetic acid; solvent B comprised 100% MeOH/1 mM trifluoroacetic acid; at time=0 min, solvent was 20% B, rising linearly to 40% B at 28 min and 100% B at 35 min]. Fractions were monitored by absorbance at 280 nm and material eluting between 37 and 45 min was collected. The solvent was removed under vacuum at ca. 35° C. and the remaining material brought to −20° C. overnight. The precipitate which formed was then filtered off rapidly and freeze-dried to give 300 mg of white substance. This was identified as 4-hydroxy-3-methoxyphenyl-β-hydroxypropionic acid ethyl ester (ethyl HMPHP) by MS [M$^-$]=240 and, on alkaline hydrolysis (1 M KOH; 30 min), gave rise to the free acid.

To generate the N-succinimidyl ester, 30 mg of ethyl HMPHP was hydrolysed for 40 min at room temperature in 0.5 ml of 1M KOH. Oxalic acid (0.6 ml of 0.5 M) was then added to bring the pH to ca. 3-4. The solution was extracted successively with $Et_2O$ (5×ca. 10 ml); the organic phases were then pooled and evaporated to dryess. N-Hydroxysuccinimide (0.1 mmol; 11.5 mg) was then added in 1.2 ml of dry 1,4-dioxane. This was then followed, gradually, by 0.1 mmol (20.7 mg) of dicyclohexylcarbodiimide in 0.6 ml of dry 1,4-dioxane. The reaction mixture was allowed to stand at room temperature for ca. 4 h and then filtered to remove precipitated DCU, a further 1.8 ml of dry dioxane being added to wash the filter.

The N-succinimidyl ester was not isolated from the reaction mixture but was converted in situ into the CoASH thioester. Lithium CoASH (40 mg; ca. 0.05 mmol) was dissolved in 2.4 ml of 0.1 M $NaHCO_3$ and the reaction mixture was added; the exchange reaction was performed under $N_2$, with stirring, for ca. 2 h at room temperature. The pH of the mixture was then adjusted to ca. 3-4 by the addition of 70 μl of 2.8 M HCl and the mixture was stored at −70° C. The CoASH thioester of HMPHP was finally isolated by preparative TLC. Cellulose TLC plates (Avicel; 1000 μm; Analtech, Newark, Del., USA), to each of which was applied 200 μl of reaction mixture, were developed in $nBuOH/HOAc/H_2O$ (5/2/3, v/v/v). The CoASH thioester was localised at $R_F$ 0.4–0.5 using a short-wave u/v lamp and recovered from the plate by scraping and elution with 50% MeOH. Identification was confirmed by MS [M=960] and by hydrolysis to the free acid (cf. ethyl HMPHP) which was measured by HPLC and used routinely as the basis for assay. The CoASH thioester showed an absorption maximum at 258 nm, and lacked the absorption maximum at 345 nm characteristic of trans-feruloyl SCoA. This molecule—and the corresponding ethyl ester and free acid—carry an asymmetric centre at the β-carbon; however, no attempt was made here to resolve the optical isomers during or after synthesis.

Preparation of vanilloyl SCoA

Vanilloyl SCoA was produced from vanillic acid via the N-succinimidyl ester, essentially according to the method described by V. Semler, G. Schmidtberg and G. G. Gross (Z. Natursforsch. 42c, 1070–1074 [1987]) for the synthesis of piperoyl SCoA.

To a stirred solution of vanillic acid (5 mmol) and N-hydroxysuccinimide (5 mmol) in 30 ml of dry 1,4-dioxane was added, in small portions, 7.5 mmol of solid dicyclohexylcarbodiimide. The solution was stirred overnight at room temperature, and precipitated DCU was removed by filtration. The filtrate was evaporated under reduced pressure at 40° C. and the oily residue dissolved in boiling $CHCl_3$. The N-succinimidyl vanillate was crystallised from solution by the dropwise addition of petroleum ether (b.p.: 30° C.–40° C). Approx 750 mg was recovered.

To generate vanilloyl SCoA from N-succinimidyl vanillate, CoASH (sodium salt; 200 mg) was dissolved in 4 ml of 0.1 M $NaHCO_3$. N-Succiniinidyl vanillate (120 mg in 4 ml of dioxane) was then added gradually over a ca.40 min period at room temperature, sparging with $N_2$. A further 4 ml of 0.1 M $NaHCO_3$ was then added, together with a further 8 ml of dioxane. Incubation under $N_2$ at room temperature, with stirring, was continued for a further 1 h. The pH was then adjusted to ca. 2.8 with 1M HCl and the solution was frozen and stored at −70° C. Isolation of vanilloyl SCoA was by preparative TLC, as described above with n BuOH/$HOAc/H_2O$(5/2/3, v/v/v) as solvent. Vanilloyl SCoA ($R_F$. 0.5–0.6) was identified using a short-wave u/v lamp and recovered by scraping, elution with 40% MeOH and freezedrying. Identification was confirmed by MS ([M⁻]=916) and the thioester liberated vanillic acid on alkaline hydrolysis.

Preparation of trans-feruloyl SCoA and other cinnamoyl SCoA thioesters

Trans-feruloyl SCoA was prepared from trans-ferulic acid via the N-succinimidyl ester, as described above for vanilloyl SCoA. Final isolation was achieved similarly by preparative TLC and elution, identification being confined by MS and by alkaline hydrolysis to free trans-ferulic acid. Caffeoyl and p-coumaroyl-SCoA thioesters were prepared similarly.

Preparation of Cell-free Extracts

Cell-free extracts of logarithmic-phase cultures (6–10 h after inoculation) were prepared by sonication. Cells from ca. 200 ml of medium were pelleted by centrifugation, and resuspended in 5–10 ml of Extraction Buffer (routinely 40 mM KPi; pH 7.2, containing 10 mM dithiothreitol). They were then sonicated (MSE Soniprep 150; Fisons Instruments, Crawley, Sussex, UK) at 4° C. (5×20 s; 22 Amplitude microns on full power), and centrifuged (20 000 x g; 20 min; 4° C.). Extracts were routinely stored frozen at −70° C. and in some instances buffer-changed using a PD10 column (Pharmacia) before use. The protein contents of extracts were variable—between 0.25 and 1.8 mg/ml.

Incubation of Cell-free Extracts

Cell-free extracts were routinely incubated at 30° C. and pH 7.5 in a reaction mixture (1 ml) containing 90 mM Tris HCl buffer and 2.5 mM $MgCl_2$, together with (as appropriate) 0.5 mM trans-ferulic acid, 0.2 mM CoASH (Li salt) and 2.5 mM ATP. This complete reaction mixture constituted an assay for trans-ferulate: CoASH ligase, where the initial increase in absorbance at 345 nm was monitored against a blank reaction mixture from which CoASH was omitted. Incubations with HMPHP SCoA (generally 0.4 mM) were performed similarly, but with the omission of trans-ferulic acid, CoASH and ATP.

Vanillin: $NAD^+$ oxidoreductase was assayed at 30° C. and pH 7.0 by monitoring the initial decrease in absorbance at 340 nm against a blank cuvette from which $NAD^+$ was omitted. Because of the similarity in extinction coefficient at 340 nm for vanillin and for NADH, the sensitivity of the assay was increased by catalysing the regeneration of NADH to $NAD^+$ by providing lactate dehydrogenase and pyruvate. Reaction mixtures contained, in 1 ml volume, 75 mM KPi buffer, pH 7.0, 0.125 mM vanillin, 1.2 mM Na pyruvate, lactate dehydrogenase (rabbit muscle), 1.1 U and $NAD^+$, 0.5 mM.

HPLC Analysis

Metabolites of trans-ferulic acid, including the CoASH thioesters, were analysed and quantitated by HPLC using a Lichrosorb RP-18 column (20 cm×4.6 mm; Capital HPLC, Broxburn, West Lothian, UK) with a multiphasic gradient; solvent "A" was 20 mM NaOAc, adjusted to pH 6.0 and solvent"B" was MeOH; the flow rate was 1.2 ml/min; the proportion of solvent "B" rose linearly from 0% at 0 min to 10% at 15 min and thence to 50% at 40 min and 70% at 45 min, finally decreasing to 0% at 50 min. Detection was with a Spectra Focus detector (Thermo Separation Products, Stone, Staffs. UK), which permitted u/v spectral analysis of each eluting component.

Typical approximate retention times were: CoASH, 3 min; vanillic acid, 7 min; trans-ferulic acid, 19 min; acetyl SCoA, 22 min; HMPHP SCoA, 29 min; vanilloyl SCoA, 31 min; vanillin, 31.5 min; trans-feruloyl SCoA, 34 min.

Mass Spectrometry

Mass spectra (+−ve and −−ve ion) were recorded on a MS 9/50 mass spectrometer (Kratos Instruments, Manchester UK), using xenon fast atom bombardment (FAB) at a potential of 5–7 kV using glycerol as matrix (see G. R.

Fenwick, J. Eagles and R. Self, *Biomedical Mass Spectrometry* 10, 382–386 (1983)).

Protein Assay

Protein was assayed by the method of M. M. Bradford (*Anal. Biochem.* 72, 248–254 (1976)), using Bio-Rad dye reagent (Bio-Rad Laboratories, Richmond, Calif., USA) and bovine serum albumin as standard.

Results

Figure 4:
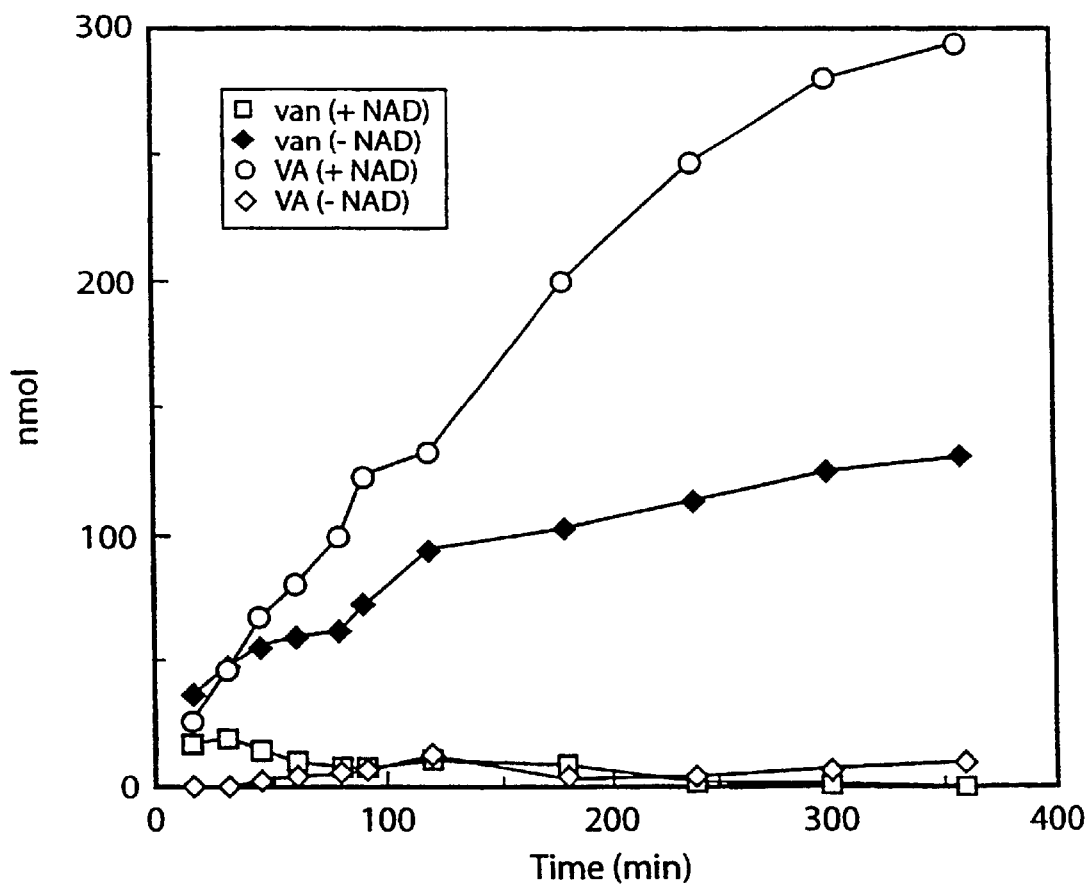

Crude extracts of *Ps. fluorescens* biovar. V, strain AN103, from cells grown on vanillate together with trans-ferulate, were able to produce vanillate when supplied with trans-ferulate, CoASH, ATP, $Mg^{2+}$ ions and $NAD^+$. In the absence of $NAD^+$, vanillate was not formed and vanillin accumulated in its place (FIG. 4). The quantity of vanillin formed in the absence of $NAD^+$ was smaller than the amount of vanillate formed in its presence. Essentially no vanillin accumulated in the presence of $NAD^+$.

This utilisation of trans-ferulate by crude extracts was dependent upon CoASH and ATP and partially upon $Mg^{2+}$ ions (Table II). These properties indicate an initial activation of trans-ferulate to trans-feruloyl SCoA by trans-ferulate: CoASH ligase. This was further shown by the rapid development of a CoASH-dependent absorbance maximum at 345 nm and particularly by a transient bathochromic shift, causing the appearance of a yellow colour, if the reaction mixture was made alkaline with NaOH (data not shown). In the initial stages of the overall reaction, the linear increase in absorbance at 345 nm enabled the activity of trans-ferulate: CoASH ligase to be assayed directly. During the later stages, however, absorbance at 345 nm would be contributed by both trans-feruloyl SCoA and vanillin or, in the presence of $NAD^+$, NADH, each of which has substantial absorbance at this wavelength.

TABLE II

Cofactor requirements for trans-ferulate utilisation by
*P. fluorescens* biovar. V, strain AN103 cell-free extracts
Reaction mixtures (165 μg protein) were incubated for 4 h at
30° C. as described in Experimental, with omissions from the
complete reaction mixture as indicated.

| | Reaction products (nmol) | | |
|---|---|---|---|
| Reaction Mixture | Trans-ferulate (remaining) | Vanillin | Vanillate |
| Complete | 267 | n.d. | 311 |
| —CoASH | 550 | n.d. | 40 |
| -$NAD^+$ | 258 | 228 | 23 |
| -ATP | 513 | n.d. | 33 |
| —$Mg^{2+}$ | 425 | n.d. | 153 | n.d. = not detectable

Figure 5:
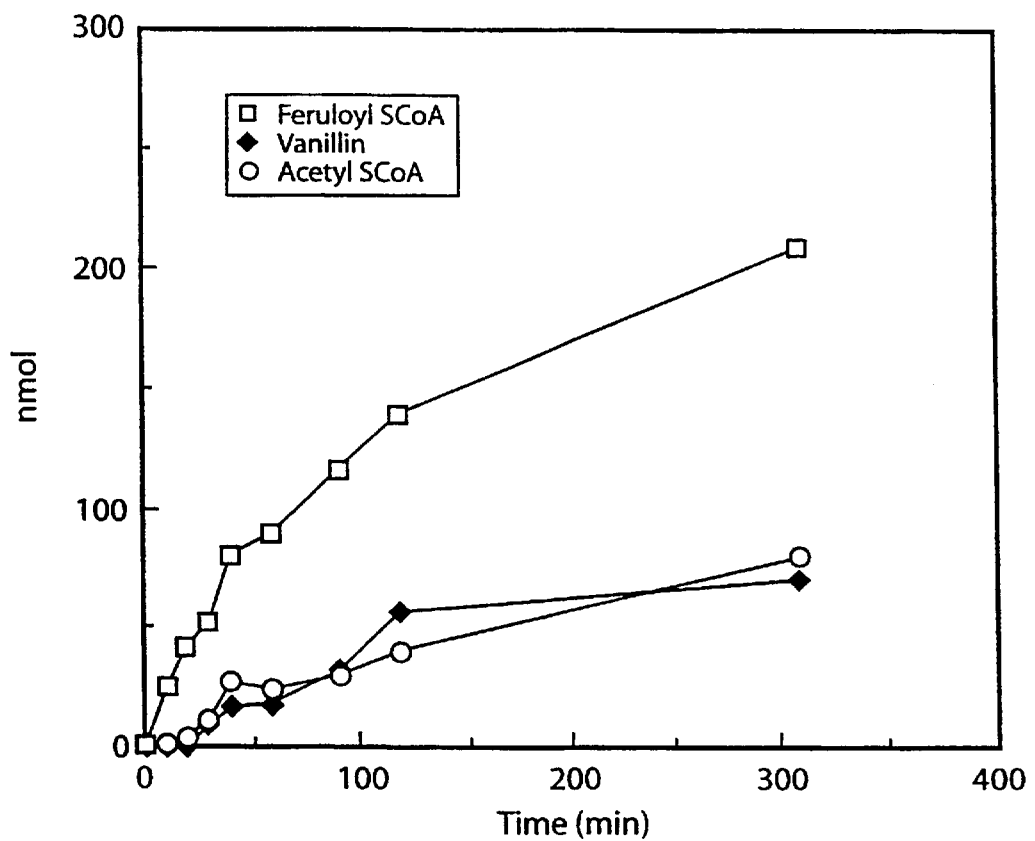
Figure 6:
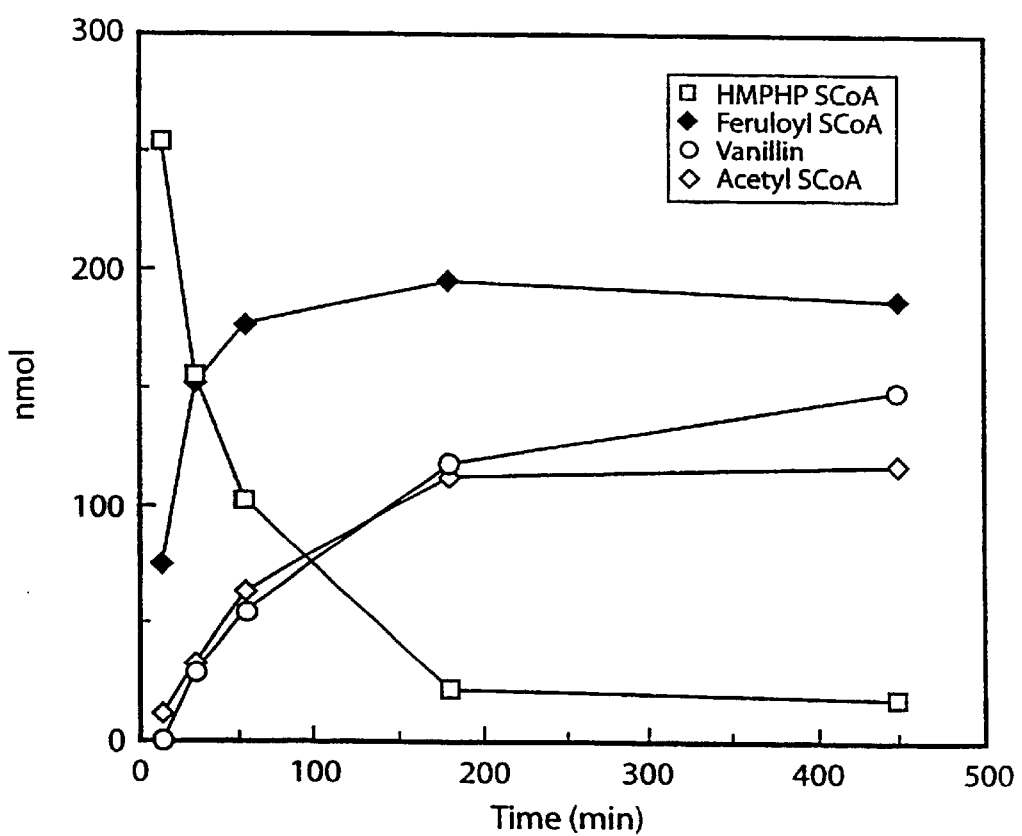

An overall non-oxidative cleavage of trans-feruloyl SCoA is implied in FIG. 5 which shows, in the absence of $NAD^+$, an equivalence between the formation of vanillin and that of acetyl SCoA. (The formation of [2-$^{13}$C] acetyl SCoA from trans-ferulate $^{13}$C-labelled in the β-carbon atom was also confirmed by NMR spectroscopy (not shown).) The cleavage mechanism was investigated further by synthesising chemically the hydrated derivative of trans-feruloyl SCoA, 4-hydroxy-3-methoxy-phenyl-β-hydroxypropionyl SCoA (HMPHP ScoA). This was incubated with cell-free extract and shown to be converted rapidly to acetyl SCoA and vanillin, in equimolar proportions (FIG. 6). A smell of vanillin was obtained when HMPHP SCoA was used as a substrate. This hydrated intermediate was not only metabolised in the forward direction, however, since an almost equivalent back reaction to fernloyl SCoA (putatively trans) was also observed. The rapidity of utilisation of HMPHP SCoA was consistent with the failure to observed its accumulation, using HPLC, during cell-free incubations with trans-ferulate, CoASH, ATP and $Mg^{2+}$ ions. This cleavage of HMPHP SCoA in the absence of $NAD^+$ indicated no intervening β-oxidation to the β-keto thioester (4-hydroxy-3-methoxybenzoyl) acetyl SCoA (cf. M. H. Zenk, *Anal. Z Pflanzenphysiol* 53, 404–414 (1965)). Attempts to prepare this compound for cell-free studies were unsuccessful, but its expected cleavage product, vanilloyl SCoA, was prepared and shown not to be metabolised to vanillin by cell-free extracts in the presence of NADH, even when simultaneous incubations with trans-ferulate in the absence of $NAD^+$ actively produced vanillin.

Besides trans-ferulic acid, caffeic acid and p-coumaric acids were converted to thioesters of CoASH by crude extracts of *Ps. fluorescens* biovar. V, strain AN103 (Table III).

TABLE III

Formulation of CoASH thioesters of trans-p-hydroxycinnamic
acids by crude extracts of *Ps. fluorescens* AN103. The activity
was assayed spectrophotometrically as described for trans-ferulate:
CoASH ligase, measuring the initial rate of increase in absorbance
at 345 nm in the case of trans-feruloyl SCoA formation, and at the
corresponding absorbance maxima for the SCoA thioesters.

| Substrate | Activity (nkat/mg protein) |
|---|---|
| Ferulate | 0.50 |
| Caffeate | 0.39 |
| p-Coumarate | 0.37 |

EXAMPLE 3

Mutants in Trans-ferulate Metabolism

Experimental

Mutagenesis of *Pseudomonas fluorescens* biovar. V, strain AN103

Ethyl methanesulphonate (EMS) was used for mutagenesis. Bacteria were grown for 2 d at 25° C. in minimal medium (MM) with vanillic acid as carbon source; 1 ml of culture was then inoculated into 50 ml of LB-MOD and grown for 16 h at 25° C. The cells were centrifuged and resuspended in 0.1 M $KH_2PO_4$ (1.25 ml) to give a cell density of $4 \times 10^9$ cells/ml ($OD_{580}$ of 1.0=$6 \times 10^7$ cells/ml). An aliquot of this cell suspension was serially diluted ($10^{-2}$–$10^{-8}$) and plated onto LB-MOD plates (0.1 ml per plate) to provide control cell counts for assessment of the efficiency of mutagenesis.

A cell suspension (1 ml) was incubated with 0.08 ml of EMS in a total of 3 ml of 0.1 M $KH_2PO_4$ at 37° C. for 45 min. The cells were then precipitated by centrifugation at 4° C. and the cell pellet was washed twice with 10 ml of LB-MOD medium, prior to resuspension in 1 ml of this medium. An aliquot was serially diluted ($10^{-2}$–$10^{-8}$) and plated onto LB-MOD plates; these were incubated at 25° C. overnight, together with the plates of the unmutagenised cells, to obtain an estimate of kill (70% kill indicates efficient mutagenesis). The remaining mutagenised cells (0.9 ml) were inoculated into LB-MOD medium (50 ml) and incubated overnight at 25° C. The mutagenised cells were then enriched for mutants in trans-ferulate utilisation by treatment with carbenicillin in minimal medium (MM) in the presence of trans-ferulic acid. The cells were harvested by centrifugation at 4° C., washed twice with MM (10 ml) and resuspended in 20 ml of MM. A sample (1 ml) was inoculated into MM (15 ml) and incubated at 25° C. for 1 h; then trans-ferulic acid (10 mM final concentration) and carbenicillin (2 mg/ml final concentration) were added. A control flask was prepared containing trans-ferulic acid, but not carbenicillin. Both flasks were incubated overnight at 25° C. for 16 h, monitoring $OD_{580}$ to estimate growth and confirm the effectiveness of the antibiotic. Penicillinase (10 units) was then added to destroy the carbenicillin, incubating overnight at 25° C. The cells were harvested by centrifugation at 4° C., washed twice in MM (10 ml) and resuspended in 5 ml of MM; 1 ml of these resuspended cells were then inoculated into 50 ml of MM containing 10 mM vanillic acid and incubated at 25° C. for ca. 24 h.

These enriched cells were screened by replica-plating for mutants unable to use trans-ferulic acid. The enriched stock was diluted to $10^{-6}$, plated onto LB-MOD (0.1 ml per plate), incubated at 25° C. for 2 d and then replica-plated onto MM containing 10 mM vanillic acid or 10 mM trans-ferulic acid. The plates were incubated at 25° C. for 2–3 d and screened for colonies able to grow on vanillate but unable to grow on trans-ferulate.

Results

By mutagenesis of strain AN103 with ethyl methane sulphonate, two classes of mutants unable to utilise trans-ferulate as sole carbon source were isolated; these were van 1, van 2 and van 3 and, secondly, van 10 and van 11. Following growth on vanillate plus trans-feralate, a representative of the first of these, van 1, showed no activity in cell-free incubations with either trans-ferulate or vanillin and lacked both trans-ferulate: CoASH ligase and the enzyme that converts vanillin to vanillate, vanillin: $NAD^+$ oxidoreductase. In contrast, the type representative of the second class, designated van 10, possessed levels of activity of both trans-ferulate: CoASH ligase and vanillin: $NAD^+$ oxidoreductase similar to those found in strain AN103, but in the presence of $NAD^+$ generated very little vanillate (Table IV). Cell-free extracts of van 10 were examined further for their ability to metabolise HMPHP SCoA. They metabolised this thioester actively, but appeared predominantly to dehydrate it to feruloyl SCoA; vanillin formation was substantially inhibited in comparison to the AN103 extract (Table V). These observations suggested that van 1 was a regulatory mutant, defective in its induction by trans-ferulate, whilst van 10 appeared to be defective in the HMPHP ScoA cleavage activity.

TABLE IV

Tans-ferulate metabolism in cell-free extracts of *P. fluorescens* biovar. V, strain AN103 and of mutant strains van 1 and van 10.
Cells were grown for 6 h in MM medium containing 10 mM vanillate together with 10 mM trans-ferulate. Extracts were then prepared as in Example 2 and assayed for trans-ferulate:CoASH ligase and vanillan:$NAD^+$ oxidoreductase. Extracts(ca. 0.3 mg of protein) were also incubated for 4 h in the presence if $NAD^+$ to determine relative amounts of vanillate formed.

| Strain | Enzyme activity (nkat mg$^{-1}$ protein) | | Vanillate formed (nmol mg$^{-1}$ protein) |
|---|---|---|---|
| | Ferulate: CoASH ligase | Vanillin: NAD oxidoreductase | |
| AN103 | 1.7 | 1.2 | 807 |
| van 1 | 0 | ~0.05 | 0 |
| van 10 | 2.0 | 1.4 | 59 |

TABLE V

Utilisation of HMPHP SCoA by extracts of *Ps. fluorescens* biovar. V, strains AN103 and van 10
Extracts (AN103, 14 µg protein; van 10, 68 µg protein) were incubated at 30° C. for 7 min in 1 ml vol containing 0.3 mM HMPHP SCoA. The increase in absorbance at 345 nm was measured against a blank reaction mixture containing no extract. Vanillin formation was measured by HPLC; the production of feruloyl SCoA was in this instance calculated from the increase in absorbance 345 nm, after subtraction of the contribution from vanillin.

| Strain | $\Delta A_{345}$ | Feruloyl SCoA (nmol) | Vanillin (nmol) |
|---|---|---|---|
| AN103 | 0.75 | 18.4 | 23.8 |
| van 10 | 0.63 | 29.2 | 4.5 |

EXAMPLE 4

Induction of Trans-ferulate Metabolism in Strain AN103 and Purification of HMPHP SCoA Cleavage Enzyme Experimental Purification of Trans-feruloyl SCoA Hydrataselaldol Cleavage Enzyme Cells (from 2 l of culture grown for 72 h on MM with 10 mM trans-ferulic acid as substrate; $OD_{565}$ca.=0.5) were extracted essentially as described in Example 2 to give 50 ml of crude extract, containing 1.28 mg of protein/ml.

Extract (16 ml, diluted to 40 ml), was applied at room temperature and 2 ml/min to a Mono Q HR10/10 anion-exchange column (Pharmacia, Piscataway, N.J., USA), pre-equilibrated with 20 mM Tris buffer (pH 7.5) containing 10 mM dithiothreitol. After elution of unadsorbed protein, protein bound to the column was eluted with a linear gradient of increasing NaCl concentration: from 0 to 0.5M NaCl in 100 ml of buffer.

Fractions eluting between 0.18 and 0.3 M NaCl and containing activity with HMPHP SCoA, as determined using the microtitre plate assay (see below), were pooled and buffer-changed by dialysis into 25 mM bis-Tris buffer, containing 10 mM dithiothreitol and adjusted to pH 7.1 with iminodiacetic acid. They were then applied at 0.75 ml/min to a Mono P HR 5/20 chromatofocusing column (Pharmacia), preequilibrated with the same buffer. After eluting unadsorbed protein from the column, adsorbed protein was eluted with a gradient of decreasing pH, generated by applying 46 ml of 10% (v/v) Polybuffer 74 (Pharmacia), containing 10 mM dithiothreitol and adjusted to pH 4.0 with iminodiacetic acid. Activity with HMPHP SCoA was eluted between pH 5.5 and 5.1.

The active fractions were again pooled together, and buffer-changed into 20 mM Tris buffer (pH 7.5), containing 1.7 M $(NH_4)_2SO_4$ and 10 mM dithiothreitol, using PD10 columns (Pharmacia), before application at 0.5 ml/min to a PhenylSuperose HR 5/5 hydrophobic interaction chromatography column (Pharmacia) preequilibrated with this buffer. Elution of bound protein was achieved with a decreasing gradient of $(NH_4)_2SO_4$ in buffer, from 1.7 M to zero over 30 ml and then continuing with buffer alone for a further 5 ml. Activity with HMPHP SCoA was eluted in this final 5 ml of buffer.

At each stage of purification, active fractions were detected by a micro-adaptation of the assay with HMPHP SCoA described above (Example 2); reactions were performed in 100 µl of reaction mixture for ca. 4 min at room temperature in microtitre wells and absorbance was then measured in an MR 5000 microtitre plate reader (Dynatech, Guernsey, Channel Islands), equipped with a 340 nm filter.

The activity of the pooled fractions was measured using HPLC to determine the reaction products of both HMPHP SCoA, (0.4 mM) and trans-feruloyl SCoA (0.28 mM) as substrates. Reaction mixtures containing 10 µl of enzyme were incubated in 100 µl volume as described above; the reaction was terminated with 100 µl of acidified MeOH (pH 3) after 2 min (HMPHP SCoA) or 5 min (trans-feruloyl SCoA) of incubation at 24° C. The proportionality of the reactions with time and with quantity of enzyme was established in preliminary determinations.

Samples (10 µl) of enzyme at each stage of purification were analysed by SDS-PAGE, with Coomassie or silver staining, essentially as described by H. Schägger and G. von Jagow, *Anal. Biochem.* 166, 368–379 (1987). An Atto AE6450 gel apparatus was used (supplied by Genetic Research Instrumentation, Dunmow, Essex, UK).

Electroelution of protein bands from fixed, stained gels was performed using a Bio-Rad Model 422 electroeluter according to the manufacturer's directions. Eluted protein was then deposited by centrifugation onto a Pro-Spin membrane (Applied Biosystems, Foster City, Calif., USA) used in accordance with the manufacturer's recommendations). N-Terminal sequencmg was performed by Alta Bioscience, University of Birmingham, Birmingham, UK.

Results

Figure 7:
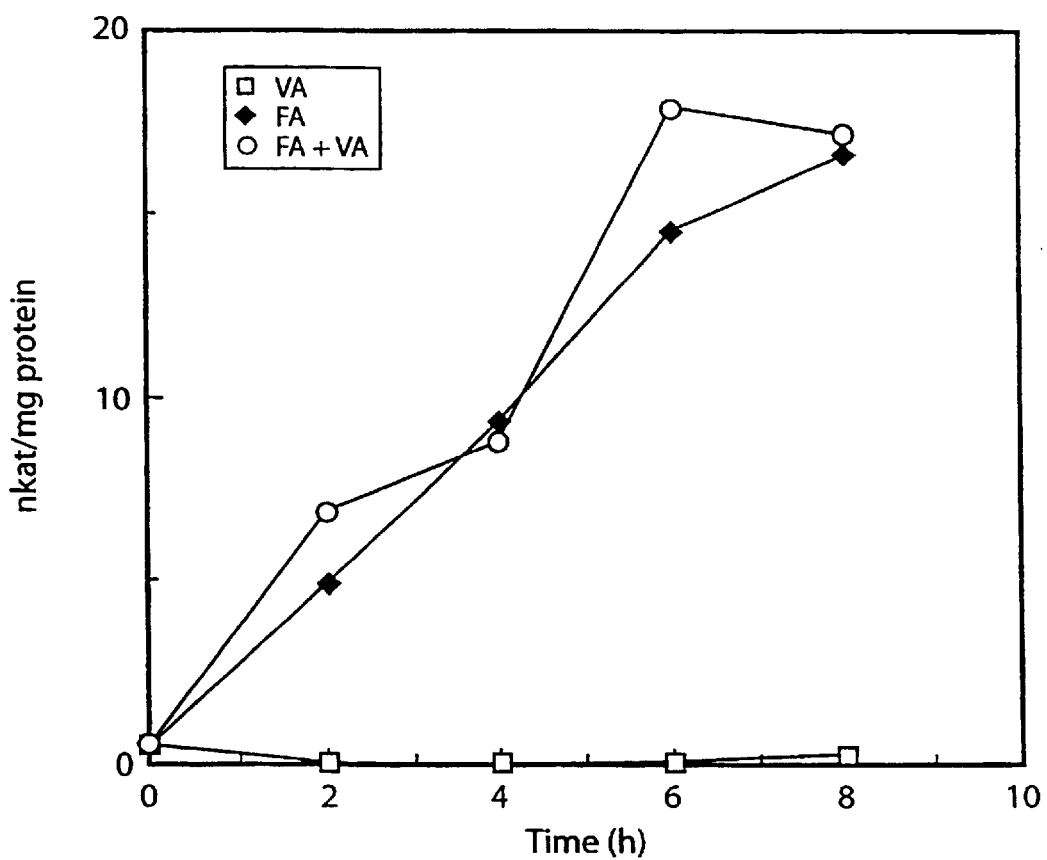

The time-course of induction of trans-ferulate:CoASH ligase in strain AN103 is shown in FIG. 7. Following transfer of vanillate-grown cells to medium containing trans-ferulate, the specific activity of the ligase in extracts increased approximately linearly over an 8-hour period. An essentially identical time-course was obtained if the cells were transferred instead to medium containing both trans-ferulate and vanillate. Vanillate, a catabolite of trans-ferulate, therefore did not inhibit the induction process.

Figure 8:
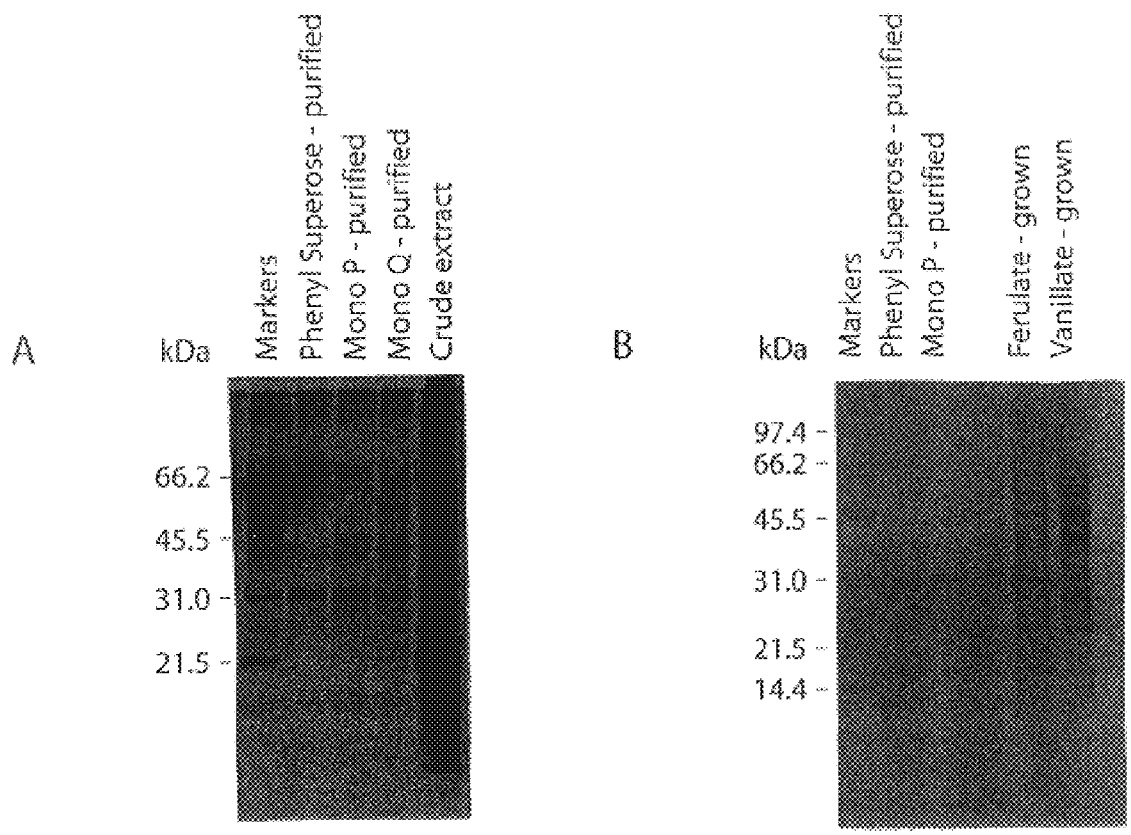

Induction of the capacity to grow on a different substrate represents a significant shift in primary metabolism, which in principle might be detectable by electrophoresis of a crude protein extract. Cell-free extracts analysed by SDS-PAGE, with Coomassie staining (see Experimental), did indeed show a distinct difference in protein banding between trans-ferulate-grown cells and vanillate-grown cells (FIG. 8). Extracts from trans-ferulate-grown cells exhibited a new, or very strongly enhanced, band corresponding to a polypeptide of molecular weight ca. 31 kD.

N-Terminal amino acid sequencing of this polypeptide, following its removal from the gel by electroblotting, gave the following sequence: Ser-Thr-Tyr-Glu-Gly-Arg-Trp-Lys-Thr-Val-Lys-Val-Glu-Ile-Gln-Asp-Gly-Ile-Ala-Phe (SEQ ID No 13).

Purification of HMPHP SCoA-utilising activity was achieved by Fast Protein Liquid Chromatography (FPLC—Pharmacia). As described above, fractions were screened for activity with HMPHP SCoA using a microtitre plate scanner; active fractions were then pooled together and activity was then measured both with HMPHP SCoA and with trans-feruloyl SCoA, determining the reaction products by HPLC.

The results of the purification are given in Tables VI and VII. Vanillin and acetyl SCoA were produced in approximately equimolar amounts, throughout the purification, with either HMPHP SCoA or trans-feruloyl SCoA as substrate. There was an approximate copurification of the activities with trans-feruloyl ScoA and HMPHP SCoA as substrate, including the formation of feruloyl SCoA from HMPHP SCoA (dehydratase reaction; reverse of reaction II): vanillin-forming activity from trans-feruloyl SCoA (reactions II+III) was purified 11.5-fold, vanillin-forning activity from HMPHP SCoA (reaction III) was purified 11.7-fold and the dehydratase reaction (reverse of reaction II) was purified 9.1-fold. Approximately 20–25% of each of these activities was fmally recovered.

TABLE VI

Purification from cells of *Ps. fluorescens* biovar V, strain AN103, was undertaken as described in Experimental, measuring activity - vanillin as product - with both trans-feruloyl SCoA and HMPHP SCoA as substrates. Values in parentheses show activity measuring acetyl SCoA as product.

Part 1

| Purification stage | Total activity (nkat) | | Total protein (mg) | Specific activity (nkat/mg) | |
|---|---|---|---|---|---|
| | trans-feruloyl SCoA | HMPHP SCoA | | trans-feruloyl SCoA | HMPHP SCoA |
| Crude Extract | 85.2 (68.2) | 59.2 (54.9) | 20.5 | 4.16 | 2.89 |
| Mono Q Fractions | 80.6 (66.2) | 45.1 (42.9) | 4.37 | 18.4 | 10.3 |
| Mono P Fractions | 56.9 (51.9) | 35.4 (33.4) | 1.61 | 34.1 | 21.2 |
| Phenyl Superose Fractions | 22.1 (19.8) | 15.5 (15.1) | 0.46 | 48.0 | 33.7 |

Part 2

| Purification stage | Ratio of activities | Purification (fold) | | Recovery (%) | |
|---|---|---|---|---|---|
| | | trans-feruloyl SCoA | HMPHP SCoA | trans-feruloyl SCoA | HMPHP SCoA |
| Crude Extract | 1.44 | 1.00 | 1.00 | 100 | 100 |
| Mono Q Fractions | 1.79 | 4.42 | 3.56 | 94.6 | 76.2 |
| Mono P Fractions | 1.61 | 8.20 | 7.34 | 66.8 | 59.8 |
| Phenyl Superose Fractions | 1.42 | 11.5 | 11.7 | 25.9 | 26.2 |

TABLE VII

HMPHP SCoA dehydratase activity during purification of trans-feruloyl SCoA hydratase/aldol cleavage enzyme
Conditions and other data as Table VI. Dehydratase reaction measured as feruloyl SCoA production.

| Purification stage | Total activity (nkat) | Specific activity (nkat/mg) | Purification (fold) | Ratio to HMPHP SCoA Cleavage Activity* |
|---|---|---|---|---|
| Crude Extract | 171 | 8.34 | 1.00 | 2.89 |
| Mono Q Fractions | 121 | 27.7 | 3.32 | 2.69 |
| Mono P Fractions | 101 | 60.5 | 7.25 | 2.85 |
| Phenyl Superose Fractions | 34.9 | 75.9 | 9.10 | 2.25 |

* see Table VI.

SDS-PAGE of the combined active fractions at each stage revealed the enhancement of a 31 kD protein band (FIG. 8), indicating purification to apparent homogeneity after chromatography on PhenylSuperose (Pharmacia). This band co-migrated with the band associated with growth of strain AN103 on trans-ferulate and gave the same N-terminal amino-acid sequence: Ser-Thr-Tyr-Glu-Gly-Arg-Trp (SEQ ID No 14).

Definitive proof of the catalysis of both reactions II and III by this protein was achieved as a result of expression of the gene in *Escherichia coli*. (see Example 5).

The Mono-P-purified enzyme was able to accept, as alternative substrates to trans-feruloyl SCoA, trans-caffeoyl SCoA and trans-4-coumaroyl SCoA (Table VIII).

TABLE VIII

Utilisation of trans-p-hydroxycinnamoyl SCoA thioesters by trans-feruloyl SCoA hydratase/aldol cleavage enzyme. Activity was determined at 30° C. and with 0.4 mM substrate using enzyme from *Ps. fluorescens* AN103 (2.8 μg of enzyme protein, partially purified by Mono-Q and Mono-P chromotography) as described in Experimental.

| Substrate | Activity (nkat/mg of protein) |
| --- | --- |
| Feruloyl SCoA | 0.60 |
| Caffeoyl SCoA | 0.36 |
| p-Coumaroyl SCoA | 0.72 |

EXAMPLE 5

Isolation of the Genes Required for the Conversion of Trans-feruloyl SCoA to Vanillic Acid (vanillate) in *Pseudomonas fluorescens* Strain AN103

A strain of *Pseudomonas fluorescens* (biovar. V, AN103) was isolated from soil at the Institute of Food Research, Norwich Laboratory, which was able to grow on trans-ferulic acid converting it to vanillic acid via vanillin. The proposed biochemical pathway for the conversion of trans-ferulic acid to vanillic acid shown in FIG. 1 was substantiated in the experiments described above in Experiments 2–4.

In order to clone the genes required for the conversion of trans-feruloyl SCoA to vanillic acid the strategy of complementing mutant derivatives of *Ps. fluorescens* AN103 that were unable to grow on trans-ferulate as sole carbon source was used. The isolation and characterization of mutants is described above in Example 3 and mutants van10 and van11 were used for clone isolation. As described in Example 3, these mutants appeared to be defective in a gene involved in the conversion of trans-feruloyl SCoA to vanillin.

A genomic library of *Ps. fluorescens* AN103 DNA was prepared in the mobilisable cosmid cloning vector pLAFR3 (B. Staskawicz, D. Dahlbeck, N. Keen, and C. Napoli, J. Bact. 169, 5789–5794 (1987)). Genomic DNA was isolated from *Ps. fluorescens* AN103 and partially digested with Sau 3A1 at 37° C. for 7–10 min. The DNA was then size-fractionated on a NaCl gradient (1.25–5M). The fraction containing DNA of 2040 kb was selected and 0.5 μg ligated into the dephosphorylated Bam H1 site of the broad-host-range cosmid cloning vector, pLAFR3. One half of the ligation mix was packaged into bacteriophage lambda particles using a Gigapack II XL kit (Stratagene, La Jolla, Calif., USA). The packaged cosmids were transfected into *Escherichia coli* strain 803 (W. B. Wood, *J. Mol. Biol.* 16, 118–133 (1966)). Approximately 10,000 primary transfectants were obtained. The lawn of cells obtained was washed from the selection plates and glycerol-containing stocks prepared for storage at −70° C.

The genomic library of *Ps. fluorescens* AN 103 DNA in cosmid pLAFR3 was introduced into the two mutant *Ps. fluorescens* derivative strains van10 and van11 using the helper plasmid, pRK2013 (D. Figurski and D. R. Helinski, *Proc Natl. Acad. Sci. USA* 76, 1648–1652 (1979)). The mutant strains were inoculated into minimal medium MM containing 10 mM vanillic acid and incubated at 25° C. for 2 days. The *Escherichia coli* strain carrying the helper plasmid (*E. coli* 803pRK2013) was inoculated into LB-Mod medium (10 ml) and incubated at 37° C. for 6 h. At the same time, 0.1 ml of the glycerol-containing stock of the AN103 genomic library was similarly inoculated and incubated. The growth of all three cultures was monitored by measuring $OD_{600}$ and appropriate volumes combined in a centrifuge tube to give equal populations of the three organisms. The mixture of cells was centrifuged, resuspended in a minimal volume of the supernatant solution and spread over a sterile gridded cellulose nitrate membrane filter (47 mm diam., Whatman, Maidstone, Kent, UK) on a moist LB-Mod agar plate. The suspension was allowed to air-dry onto the filter for a few minutes and then incubated overnight at 25° C. The bacteria were then washed from the filter using 2 ml of $H_2O$ and aliquots (0.1 ml) were applied to selection plates consisting of MM agar with 10 mM vanillic acid and 5 μg/ml tetracycline. These were incubated at 25° C. for 2 days and the colonies obtained (>1000 per plate) were replica-plated to similar plates containing trans-ferulic acid in place of vanillic acid; these were incubated similarly. Colonies (2–3 per plate) able to grow on the plates containing trans-ferulic acid were selected and inoculated into fresh MM medium containing 10 mM trans-ferulic acid and 5 μg/ml tetracycline. Four such isolates in which the mutation in the *Ps. fluorescens* strains van10 and van11 was complemented by the introduced cosmid were selected for further analysis. These strains were purified and the cosmid DNA was extracted by the mini-preparation method of F. G. Grosveld, H. H. M. Dahl, E. Deboer and R. A. Flavell (*Gene* 13, 227–231 (1981)). The cosmid DNA was transformed into *E. coli* strain 803 and was again isolated as described by D. S. Holmes and M. Quigley (*Anal. Biochem.* 114, 193–197 (1981)). Two of the cosmid clones, pFI 793 and pFI 794, were isolated as complementing *Ps. fluorescens* mutant strain van 10, whereas cosmid clones pFI 795 and pFI 796 complemented *Ps. fluorescens* mutant strain van 11.

To test whether the plasmid clones pFI 793, pFI 794, pFI 795 and pFI 796 would complement any of the other *Ps. fluorescens* mutants, each plasmid was introduced into *Ps. fluorescens* mutant strains van1, van2, van3, van10 and van11. As described above in Example 3 the mutant strains van1, van2 and van3 appear to be defective in a regulatory function that eliminates at least two different enzyme activities. The *Ps. fluorescens* van mutants were grown on MMO+ 10 mM vanillic acid agar medium for two days at 25° C. The strain carrying the helper plasmid (803pRK2013) was grown on LB-Mod agar+kanamycin (25 μg/ml) at 37° C. overnight. The *E. coli* 803 cosmid clones carrying pFI 793, pFI 794, pFI 795 and pFI 796 were grown on LB-Mod agar medium+ tetracycline (5 μg/ml) at 37° C. overnight. The bacteria were,patch mated (ie a loopful of donor, recipient and helper strain were mixed together on LB-Mod agar and incubated overnight at 25° C). The bacteria were replica plated onto selection medium (MMO+10 mM trans-ferulic acid+ tetracycline and MMO+10 mM vanillic acid+tetracycline) and incubated at 25° C. for two days. All four cosmid clones pFI 793, pFI 794, pFI 795 and pFI 796 complemented all of the van mutants (van1, van2, van3, van10 and van11) enabling them to grow on trans-ferulate as sole carbon source.

Figure 9:
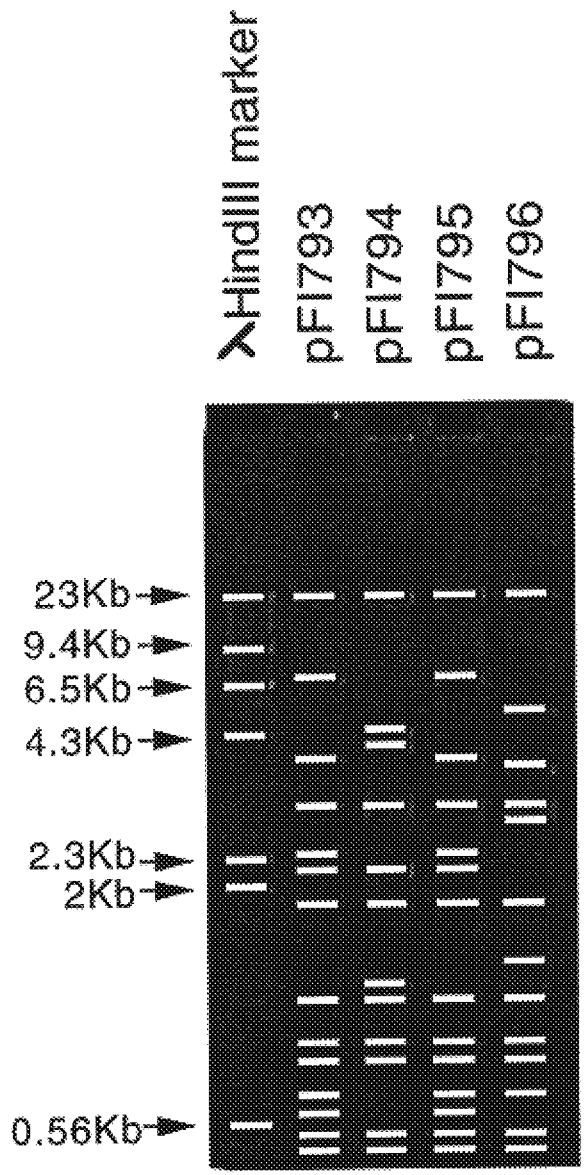

The cosmid clone DNAs were analyzed by digestion with restriction endonucleases Hind III and Eco RI to reveal insert DNA. Each of the four clones pFI 793, pFI 794, pFI 795 and pFI 796 carried inserts of between 20 and 30 kb. The four cosmid clones gave distinct restriction patterns, but appeared to share some restriction fragments of the same size. To identify restriction fragments that were common to the cosmid clones cosmid pFI 793 was used as a probe against DNA of all four cosmid DNA preparations that had been double-digested with restriction endonucleases EcoRI and PstI. Cosmid DNA was isolated using Qiagen midi columns according to the manufacturers instructions and was digested with restriction endonucleases EcoRi and PstI. The resulting fragments were separated by agarose gel electrophoresis and Southern blotted to a Hybond-N filter as described by Sambrook et al (Sambrook, J., Fitsch, E. F. and Maniatis, T. *Molecular Cloning: A Laboratory Manual,* 2nd edition, Cold Spring Harbor, N.Y., 1989). Cosmid pFI 793 DNA was linearised, denatured and labelled with digoxygenin prior to probing the Southern blotted DNA according to the instructions supplied by Boehringer (Lewes, Sussex, UK). The pFI 793 probe hybridised to all of the EcoRI/PstI restriction fragments of pFI 795 indicating that these two clones are identical. Excluding the vector band at least six EcoRI/PstI fragments appeared to be common to pFI 793, pFI 794, pFI 795 and pFI 796. These were fragments of 6.6 kb, 2.9 kb, 1.8 kb, 1.4 kb, 1.25 kb and 1.1 kb. The 1.25 kb fragment appeared to be a doublet or triplet. The DNA fragment patterns of the four cosmid clones after restriction digestion with EcoRI/PstI are shown in FIG. 9. For clarity the ethidium bromide stained DNA bands have been diagrammatically superimposed on the original agarose gel.

Figure 11:
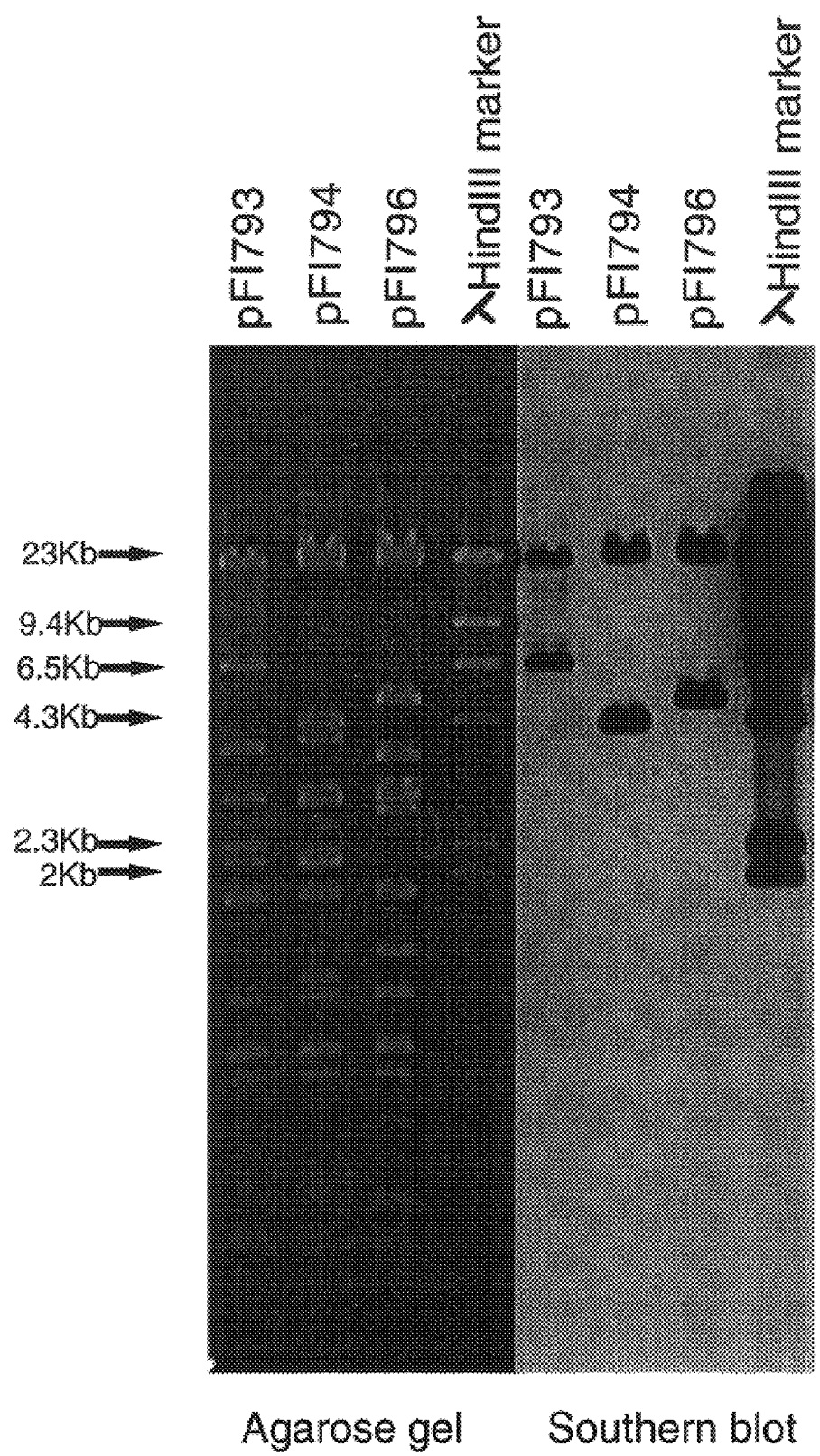

As described above in Example 4 protein analysis of *Ps. fluorescens* biovar. V, strain AN103 showed that cells grown on trans-ferulate contained much larger amounts of a protein of about 31 kD compared with cells grown on vanillic acid. The twenty N-terminal amino acids of this protein were sequenced. This amino acid sequence was then used to design degenerate oligonucleotide primers that enabled the 60 bp sequence of DNA coding for this N-terminus to be amplified from pFI 793 by PCR (FIG. 10). This sequence was used to probe EcoRI/PstI digests of the cosmid clones. By this technique the fragment containing the region of DNA encoding the 31 kD protein in each of the cosmid clones could be identified (FIG. 11). This proved to be a fragment of 6 kb in cosmids pFI 793 and pFI 795, a fragment of 4.3 kb in cosmid pFI 794 and a fragment of 5.5 kb in cosmid pFI 796.

The 4.3 Kb EcoRI/PstI fragment of pFI 794 was sub-cloned into the *E. coli* vector pUC19 using strain XLI (Blue) and its nucleotide sequence was determined using an Applied Biosystems DNA Sequencer (Model 373; Perkin Elmer, Warrington, UK); together with the manufacturer's Taq DyeDeoxy Terminator Cycle sequencing kit. A primer walking strategy was used with oligonucleotide primers being synthesized on an ABI 392 Synthesizer (Perkin Elmer, Warrington, UK). The DNA sequence of the 4.3 kb fragment is presented in FIG. 12. The open reading frame encoding the same amino-terminus as determined previously starts at position 2872 and is terminated by a stop codon at position 3700. This ORF of 828 bp encodes a protein 276 amino acids long with a molecular size of 31.010 kD in good agreement with the protein gel analysis. The translated amino-acid sequence of this gene is also presented in FIG. 12. In order to confirm the function of this gene it was sub-cloned and expressed in *E. coli*. From the DNA sequence PCR primers were designed to amplify the gene such that it was flanked by restriction endonuclease sites EcoRI and BamHI. The amplified gene retained its native ribosome binding site being initiated at base −29 and ending 6 bp downstream of the stop codon. The amplified fragment was cloned into the equivalent sites of the *E. coli* expression vector pSP72 (Promega, Southampton, UK) and transformed into *E. coli* JM109(DE3).

The *E. coli* 803 clones carrying the hydratase/cleavage enzyme gene, plus a putative promoter, as a PCR product in the vector pRK415 were used in a triparental patch mating experiment essentially as described earlier in relation to complementation by the cosmid clones pFI 793-6. The complemented van 10 strain was demonstrated to have recovered the ability to grow on trans-ferulic acid, confirming directly that the mutation in van 10 resided in the gene encoding the trans-feruloyl ScoA hydratase/cleavage enzyme.

The presence of a novel enzyme activity (cf. Example 4) in the *E. coli* clone was demonstrated. *E. coli* cells were grown at 37° C. for 3 h in 50 ml of L medium, containing ampicillin (50 µg/ml) with and without induction by IPTG. Extracts were prepared as described above in Example 2 for *Ps. fluorescens* AN103, but without centrifugation. The crude extract was used for assay. Enzyme activity with both HMPHP SCoA and trans-feruloyl ScoA was determined as described above in Example 4 using HPLC to determine the reaction products. The results presented in Table IX clearly demonstrate that vanillin and acetyl SCoA were produced in equimolar proportions both with trans-feruloyl SCoA and with HMPHP SCoA as substrates. In addition, HMPHP SCoA was also dehydrated to feruloyl SCoA, putatively trans-feruloyl SCoA, demonstrating the reverse of activity II. These results are closely similar to those obtained with the vanillin-forming cleavage enzyme purified from *Pseudomonas fluorescens* AN103, although the ratio of activities with trans-feruloyl SCoA and HMPHP SCoA differs slightly between the two preparations. There was no activity with either trans-feruloyl SCoA or HMPHP SCoA in extracts of an unmanipulated *E. coli* strain, whether induced or not. In the manipulated strain *E. coli* 1039 that expresses the Pseudomonas gene the specific activity was slightly lower in the exLract made following induction than in that made from uninduced bacteria. Since the assay measures only active enzyme it is conceivable that increased protein expression occurs upon induction but this may result in incorrectly folded and therefore inactive enzyme. It was not possible to detect expression of the 31 kD protein visually on Coomassie-stained, one-dimensional SDS gels because of its co-migration with the strongly expressed β-lactamase encoded by the vector ampicillin resistance marker.

TABLE IX

Expression of trans-feruloyl SCoA hydratase/aldol cleavage enzyme in *Escherichia coli*.
Enzyme was extracted as described in Example 2 and
activity determined as described in Example 4,
using trans-feruloyl SCoA (0.28 mM) and HMPHP SCoA (0.4 mM)) as substrates.
Reaction mixtures contained ca. 10 μg of protein.
n.d. - not detectable

| | Specific activity (nkat/mg of protein) | | | | |
|---|---|---|---|---|---|
| | trans-Feruloyl SCoA as substrate | | HMPHP SCoA as substrate | | |
| E. coli Cell line | Vanillin formation | Acetyl SCoA formation | Vanillin formation | Acetyl SCoA formation | Feruloyl SCoA formation |
| Control | n.d. | n.d | n.d. | n.d. | n.d. |
| Control (induced) | n.d. | n.d. | n.d. | n.d. | n.d. |
| 1039 | 1.53 | 1.80 | 1.52 | 1.80 | 3.35 |
| 1039 (induced) | 1.24 | 1.34 | 1.27 | 1.46 | 3.16 |

The DNA downstream of the gene encoding the 31 kD protein was targeted for cloning and sequencing and for analysis of additional open reading frames. A PCR-generated probe was used to identify an overlapping XhoI fragment of 1.5 kb. Sequencing from this fragment and subsequently directly from the parent cosmid clone pFI794 revealed a second open reading frame of 1449 bp beginning at base 3804. The translation of this nucleotide sequence revealed a polypeptide of 483 amino acids. Comparison with sequences in the databases revealed appreciable homology to salicylaldehyde: $NAD^+$ oxidoreductase.

In order to confirm the function of this gene, expression was determined in *E. coli* strain DH5, which contained the vector pUC18 into which the full-length open reading frame had been inserted such that expression was from the lac promoter on the vector. Vanillin: $NAD^+$ oxidoreductase activity was confirmed and was absent from a control strain bearing the unmodified pUC 18 vector. Using the enzyme assay described in Example 2, activity with vanillin as substrate was determined as 3.0 nkat/mg of protein; activity with salicylaldehyde was 2.8 nkat/mg.

Figure 17:
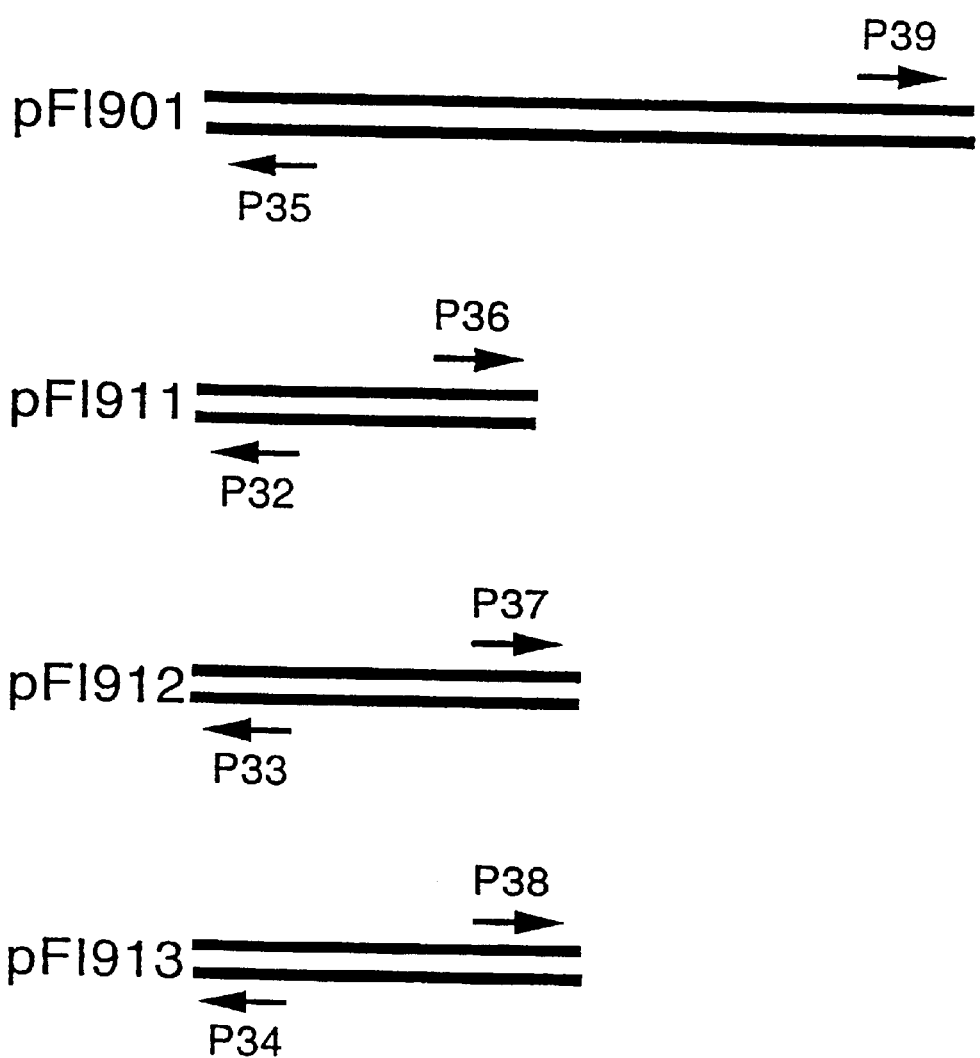
FIG. 17 is a diagrammatic representation of the outward reading primers for pFI901 (P35 and P39), pFI911 (P32 and P36), pFI912 (P33 and P37) and pFI913 (P34 and P38).
Figure 18:
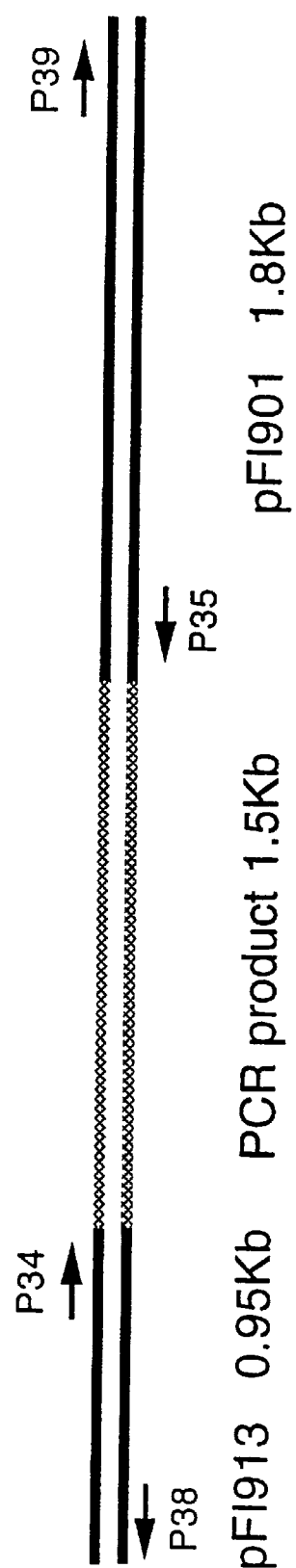
FIG. 18 is a diagrammatic representation showing the formation of the 1.5 kb PCR product, using primers P34 and P39, which spans the region in the cosmid between the inserts of pFI913 and pFI901.

Additional sequence analysis of DNA cloned from *Ps. fluorescens* AN103 was undertaken using cosmid clone pFI 793. The 1.8, 0.9 and 0.8 kb EcoRI/PstI fragments were sub-cloned into *E. coli* vector pUC18 and their nucleotide sequences were determined. Sequencing the 0.9 kb subclones revealed that there are two different fragments of the same size. The nucleotide sequences of DNA fragments of 1837 bp, 960 bp, 959 bp and 854 bp in sub-clones pFI 901, pFI 912, pFI 913 and pFI 911 respectively are presented in FIGS. 13 to 16. Outward reading PCR primers were designed from the ends of each of the four sequences as shown in FIG. 17. Use of these priners in all possible pairwise combination with pFI 793 as template showed that the 1.8 kb fragment of pFI 901 was separated from the 959 bp fragment of pFI 913 by 1.5 kb on the cosmid DNA (FIG. 18). Direct sequence analysis of this 1.5 kb PCR product enabled this together with the 1.8 kb and 959 bp fragments to be merged into one larger fragment of 4.3 kb (FIG. 19).

EXAMPLE 6

Production of Vanillin From Trans-ferulovl SCoA and Enzyme Activities II and III Trans-feruloyl SCoA was synthesised as described in Example 2, and was used as a substrate of the trans-feruloyl SCoA hydratase/aldol cleavage enzyme (ie a single polypeptide with enzyme activities II and III) as purified by the method described in Example 4. Vanillin was produced from trans-feruloyl SCoA.

EXAMPLE 7

A transgenic Tobacco Plant Which Produces Vanillin

*Nicotiana tabacum* (tobacco) is transformed using a strain of *Agrobacterium tumefaciens* which has been modified so that it transfers the *Ps. fluorescens* gene encoding enzyme activities II and III (see Example 5) to the tobacco plant. The tobacco plant produces vanillin in those parts of the plant which have trans-feruloyl SCoA present, at least in the form of a vanillin glycoside.

What is claimed is:

1. An isolated polynucleotide contained within the cosmid clone pFI 793 as deposited under the Budapest Treaty at the National Collections of Industrial and Marine Bacteria Limited, Scotland under Accession No NCIMB 40777, the isolated polynucleotide hybridizing to the complement of SEQ ID NO: 1 when incubated in an aqueous solution containing 2×SSC and at a temperature of 65° C.

2. Cosmid pFI 793 as deposited under the Budapest Treaty at the National Collections of Industrial and Marine Bacteria Limited, Scotland under Accession No NCIMB 40777.

3. An isolated polynucleotide that hybridizes to the complement of SEQ ID NO: 1, when incubated in an aqueous solution containing 2×SSC and at a temperature of 65° C., and encodes a polypeptide which, in the presence of appropriate cofactors if any, is capable of catalyzing the conversion of trans-feruloyl-S-CoA to vanillin via 4-hydroxy-3-methoxyphenyl-β-hydroxy-propionyl SCoA (HMPHP SCoA).

4. An isolated polynucleotide according to claim 3 wherein the polypeptide is a trans-feruloyl SCoA hydratase.

5. An isolated polynucleotide according to claim 3 wherein the polypeptide is a HMPHP SCoA cleavage enzyme.

6. An isolated polynucleotide according to claim 3 wherein the polypeptide comprises an amino acid sequence of SEQ ID NO: 2, or an enzymatically active fragment thereof.

7. An isolated polynucleotide according to claim 1 encoding a polypeptide comprising trans-feruloyl SCoA hydratase activity and HMPHP SCoA cleavage activity.

8. An isolated polynucleotide comprising a nucleotide sequence of SEQ ID NO: 1 or fragments thereof encoding enzymatically active polypeptides, which fragments hybridize to the complement of SEQ ID NO: 1 when incubated in an aqueous solution containing 2×SSC and at a temperature of 65° C.

9. An isolated polynucleotide according to claim 8 wherein the polynucleotide comprises the nucleotide sequence of SEQ ID NO: 1.

10. A nucleic acid vector comprising a polynucleotide according to claim 3.

11. A nucleic acid vector comprising a polynucleotide according to claim 8.

12. A host cell comprising a polynucleotide according to claim 3.

13. A host cell according to claim 12 which is a plant cell.

14. A host cell according to claim 13 wherein said plant cell is a cell from any one of Nicotiana spp., Solanum tuberosum, Brassica spp., Beta spp., Capsicum spp. and Vanilla spp.

15. A host cell according to claim 13 wherein said cell is comprised in a plant.

16. A transgenic plant comprising at least one polynucleotide that hybridizes to the complement of SEQ ID NO: 1 when incubated in an aqueous solution containing 2×SSC and at a temperature of 65° C., wherein said plant, as a consequence of the presence of said polynucleotide, expresses trans-feruloyl ScoA hydratase activity and 4-hydroxy-3-methoxyphenyl-β-hydroxy-propionyl ScoA cleavage activity.

* * * * *

SEQUENCE LISTING

<160> NUMBER OF SEQ ID NOS: 14

<210> SEQ ID NO 1
<211> LENGTH: 828
<212> TYPE: DNA
<213> ORGANISM: Pseudomonas fluorescens

<400> SEQUENCE: 1
atgagcacat acgaaggtcg ctggaaaacg gtcaaggtcg aaatcgaaga cggcatcgcg     60
tttgtcatcc tcaatcgccc ggaaaaacgc aacgcgatga gcccgaccct gaaccgcgag    120

-continued

```
atgatcgatg ttctggaaac cctcgagcag gaccctgccg ccggtgtgct ggtgctgacc      180
ggtgcgggcg aagcctggac cgcaggcatg gacctcaagg aatacttccg cgaagtggac      240
gccggcccgg aaatcctcca ggaaaaaatc cgccgcgaag cctcgcaatg caatggaaa       300 ctgctgcgca tgtacgccaa gccgaccatc gccatggtca atggctggtg cttcggcggc      360
ggtttcagcc cgctggtggc ctgcgacctg gcgatctgcg ccgacgaagc aaccttcggt      420
ctctcggaaa tcaactgggg tatcccgccg ggcaacctgg tgagcaaggc catggccgac      480
accgtgggcc accgccagtc gctctactac atcatgaccg gcaagacctt cggtgggcag      540
aaagccgccg agatgggcct ggtcaacgaa agcgtgcccc tggcgcaact gcgcgaagtc      600
accatcgagc tggcgcgtaa cctgctcgaa aaaaacccgg tggtgctgcg tgccgccaaa      660
cacggtttca acgctgccg cgaactgacc tgggagcaga acgaggatta cctgtacgcc       720
aagctcgatc agtcgcgttt gctggacacc gaaggcggtc gcgagcaggg catgaagcaa      780
ttcctcgacg acaagagcat caagcctggc ctgcaagcgt ataaacgc                   828
```

<210> SEQ ID NO 2
<211> LENGTH: 276
<212> TYPE: PRT
<213> ORGANISM: Pseudomonas fluorescens

<400> SEQUENCE: 2

```
Met Ser Thr Tyr Glu Gly Arg Trp Lys Thr Val Lys Val Glu Ile Glu
  1               5                  10                  15

Asp Gly Ile Ala Phe Val Ile Leu Asn Arg Pro Glu Lys Arg Asn Ala
             20                  25                  30

Met Ser Pro Thr Leu Asn Arg Glu Met Ile Asp Val Leu Glu Thr Leu
         35                  40                  45

Glu Gln Asp Pro Ala Ala Gly Val Leu Val Leu Thr Gly Ala Gly Glu
     50                  55                  60

Ala Trp Thr Ala Gly Met Asp Leu Lys Glu Tyr Phe Arg Glu Val Asp
 65                  70                  75                  80

Ala Gly Pro Glu Ile Leu Gln Glu Lys Ile Arg Arg Glu Ala Ser Gln
                 85                  90                  95

Trp Gln Trp Lys Leu Leu Arg Met Tyr Ala Lys Pro Thr Ile Ala Met
            100                 105                 110

Val Asn Gly Trp Cys Phe Gly Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Gln Lys Ala Ala Glu Met Gly Leu Val Asn Glu Ser Val
            180                 185                 190

Pro Leu Ala Gln Leu Arg Glu Val Thr Ile Glu Leu Ala Arg Asn Leu
        195                 200                 205

Leu Glu Lys Asn Pro Val Val Leu Arg Ala Ala Lys His Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Gly Arg Glu Gln
                245                 250                 255
```

Gly Met Lys Gln Phe Leu Asp Asp Lys Ser Ile Lys Pro Gly Leu Gln
         260                 265                 270

Ala Tyr Lys Arg
         275

<210> SEQ ID NO 3
<211> LENGTH: 1446
<212> TYPE: DNA
<213> ORGANISM: Pseudomonas fluorescens

<400> SEQUENCE: 3

```
atgctggacg tgcccctgct gattggcggc cagtcgtgcc ccgcgcgcga cggtcgaacc      60
ttcgagcgcc gcaacccggt gactggcgag ttggtgtcgc gggttgccgc cgccaccctg     120
gaagatgccg acgccgccgt ggccgctgcc cagcaagcgt tcccgcgtgg gccgcgctg      180
gcgcccaatg aacggcgcag ccgtttgctc aaggccgccg aacaattgca ggcgcgcagc     240
ggcgagttca tcgaggcggc gggcgagacc ggcgccatgg ccaactggta cgggttcaac     300
gtacggctgg cggccaacat gctgcgtgaa gcggcatcga tgaccaccca ggtcaatggt     360
gaagtgattc cctcggacgt tcccggcagt ttcgccatgg ccctgcgcca gccctgtggc     420
gtggtgctgg catcgcccc ctggaacgcc cggtgattc tcgccacccg ggcgattgcc       480
atgccgctgg cctgtggcaa caccgtggtg ctgaaggctt ccgagctgag tccggcggtg     540
catcgcttga tcgccaggt gctgcaggac gccggcctgg gcgatggcgt ggtcaacgtc     600
atcagtaatg cgccggcgga tgcggcacag attgtcgagc gcctgattgc caacccggcc     660
gtacgccggg tcaatttcac cggttcgacc cacgtcgggc gcattgtcgg cgagctctcg     720
gcgcgccacc tcaaaccggc gttgctcgag ctgggcggca aggcaccgtt gctggtgctc     780
gacgatgccg aactggaggc tgccgtgcag gcggcggcgt ttggcgccta cttcaaccag     840
ggacagatct gtatgtccac cgagcgcctg attgtcgatg ccaaggtggc cgacgccttt     900
gtcgcccagt tggcggccaa ggtcgagacc ctgcgcgccg tgatcctgc cgacccggag     960
tcggtgctcg gttcgctggt ggacgccagc gctggcacgc ggatcaaagc gttgatcgat    1020
gatgccgtgg ccaagggcgc gcgcctggta atcggcgggc aactggaggg cagcatcttg    1080
cagccgaccc tgctcgacgg tgtcgacgcg agcatgcgtt tgtaccgcga agagtccttc    1140
ggccgcgtgg cggtggtgct cgcggcggag ggcgaagaag cgctgttgca actggccaac    1200
gactccgagt tcggtttgtc ggcggcgatt ttcagtcgtg acaccggccg tgccctggcc    1260
ctggcccagc gggtcgaatc gggcatctgc cacatcaacg cccgaccgt gcacgacgaa     1320
gcgcaaatgc cttttggcgg ggtcaagtcc agcggctacg cagttttgg cggcaaggca     1380
tcgattgagc atttcactca gttgcgctgg gtcaccctcc agaatggtcc acggcactat    1440
ccgatc                                                                1446
```

<210> SEQ ID NO 4
<211> LENGTH: 482
<212> TYPE: PRT
<213> ORGANISM: Pseudomonas fluorescens

<400> SEQUENCE: 4

Met Leu Asp Val Pro Leu Leu Ile Gly Gly Gln Ser Cys Pro Ala Arg
1               5                   10                  15

Asp Gly Arg Thr Phe Glu Arg Arg Asn Pro Val Thr Gly Glu Leu Val
            20                  25                  30

-continued

```
Ser Arg Val Ala Ala Ala Thr Leu Glu Asp Ala Asp Ala Ala Val Ala
         35                  40                  45

Ala Ala Gln Gln Ala Phe Pro Ala Trp Ala Ala Leu Ala Pro Asn Glu
 50                  55                  60

Arg Arg Ser Arg Leu Leu Lys Ala Ala Glu Gln Leu Gln Ala Arg Ser
 65                  70                  75                  80

Gly Glu Phe Ile Glu Ala Ala Gly Glu Thr Gly Ala Met Ala Asn Trp
                 85                  90                  95

Tyr Gly Phe Asn Val Arg Leu Ala Ala Asn Met Leu Arg Glu Ala Ala
             100                 105                 110

Ser Met Thr Thr Gln Val Asn Gly Glu Val Ile Pro Ser Asp Val Pro
             115                 120                 125

Gly Ser Phe Ala Met Ala Leu Arg Gln Pro Cys Gly Val Val Leu Gly
         130                 135                 140

Ile Ala Pro Trp Asn Ala Pro Val Ile Leu Ala Thr Arg Ala Ile Ala
145                 150                 155                 160

Met Pro Leu Ala Cys Gly Asn Thr Val Val Leu Lys Ala Ser Glu Leu
                 165                 170                 175

Ser Pro Ala Val His Arg Leu Ile Gly Gln Val Leu Gln Asp Ala Gly
                 180                 185                 190

Leu Gly Asp Gly Val Val Asn Val Ile Ser Asn Ala Pro Ala Asp Ala
         195                 200                 205

Ala Gln Ile Val Glu Arg Leu Ile Ala Asn Pro Ala Val Arg Arg Val
     210                 215                 220

Asn Phe Thr Gly Ser Thr His Val Gly Arg Ile Val Gly Glu Leu Ser
225                 230                 235                 240

Ala Arg His Leu Lys Pro Ala Leu Leu Glu Leu Gly Lys Ala Pro
                 245                 250                 255

Leu Leu Val Leu Asp Asp Ala Asp Leu Glu Ala Ala Val Gln Ala Ala
                 260                 265                 270

Ala Phe Gly Ala Tyr Phe Asn Gln Gly Gln Ile Cys Met Ser Thr Glu
             275                 280                 285

Arg Leu Ile Val Asp Ala Lys Val Ala Asp Ala Phe Val Ala Gln Leu
     290                 295                 300

Ala Ala Lys Val Glu Thr Leu Arg Ala Gly Asp Pro Ala Asp Pro Glu
305                 310                 315                 320

Ser Val Leu Gly Ser Leu Val Asp Ala Ser Ala Gly Thr Arg Ile Lys
                 325                 330                 335

Ala Leu Ile Asp Asp Ala Val Ala Lys Gly Ala Arg Leu Val Ile Gly
             340                 345                 350

Gly Gln Leu Glu Gly Ser Ile Leu Gln Pro Thr Leu Leu Asp Gly Val
         355                 360                 365

Asp Ala Ser Met Arg Leu Tyr Arg Glu Glu Ser Phe Gly Pro Val Ala
     370                 375                 380

Val Val Leu Arg Gly Glu Gly Glu Ala Leu Leu Gln Leu Ala Asn
385                 390                 395                 400

Asp Ser Glu Phe Gly Leu Ser Ala Ala Ile Phe Ser Arg Asp Thr Gly
                 405                 410                 415

Arg Ala Leu Ala Leu Ala Gln Arg Val Glu Ser Gly Ile Cys His Ile
             420                 425                 430

Asn Gly Pro Thr Val His Asp Glu Ala Gln Met Pro Phe Gly Gly Val
         435                 440                 445

Lys Ser Ser Gly Tyr Gly Ser Phe Gly Gly Lys Ala Ser Ile Glu His
```

Phe Thr Gln Leu Arg Trp Val Thr Leu Gln Asn Gly Pro Arg His Tyr
465                 470                 475                 480

Pro Ile

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccacgtacg agggccgctg gaagac                                          26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaacgcgatg ccgtcctgga tctc                                            24

<210> SEQ ID NO 7
<211> LENGTH: 5252
<212> TYPE: DNA
<213> ORGANISM: Pseudomonas fluorescens

<400> SEQUENCE: 7
gaattctctc gcgctttgcc cagtcctacc cgctggtgca gatcgaggtg cattgcgagt      60
cgtccaagca acttctcttg cgccaggacc tcgacctgtc catcgtgacc cgcgaacccg     120
gcaacgaaat cggccagctg ttgcgcaagg agcgttttgt ctgggcccag gcccagtgct     180
acaaccctgt cgagcaatca cccttgccgc tggcgatgtt caacagtgac tgcttctgcc     240
gtctttgggc ctgtaatgcg ctggatgccg ccggacgtga ataccgcatc gcctacaaca     300
gttcgagcct gtcggcgctg atggcagtgg tcagcgccgg gctggcggtg accgctcaat     360
tggaaagcct gatcccgcag gacatgcgca tcctcggcga ggccgaaggc ctgccccaac     420
tgcccgaggc gagcatcatg ctgctgcgca atctgcataa tccgtcgccg attaccgaat     480
gtctggcgga gcacatcgtc gaaggcttca actttaaag gcgagcatca ccgcgcagag     540
caccagaaaa ccgcagaaca aaccgcgtag tagccgctcc ggcagggcgt gggcaatctt     600
cacgccccaa ctgatactga gcagaccgcc caccgccatg gcaacgcgat gtgccagtc      660
gacttgctgg tgcagggcgt aggtcgccag ggttacaccg tgctgggta aagccagtgc      720
caacgacagg ccctgggcca ccacctgggt ggtgccaaac aagctggtca ataccggcgt     780
tgcgaccaca gcgccgccca ccccgaacaa gccacccatg acgccggacg ccgcgcccag     840
caccccgagc cagggccacg aatagcgcat ctgcgcagtc ggtgccgccg cagtcatgaa     900
catgcgcatc aggttgtaga ccgacaaggc caccagaaaa ccacgaaacc cgatgcgcat     960
cacctgagcg tcgatcccca ccgcccagat cgaaccgagc caggcaaagc agaaccccat    1020
ggaggccaac ggcagcgcgt ggcgcaactc gatgcgatta cgttggtgat aacgccataa    1080
cgccagcatc acgttcggca ccaccatgac cagagctgtg ccctgggcaa gctgctgatc    1140

-continued

```
caggccaaat aacacgccca gagcgggaat ggcgatcaag ccaccgccga ttccaaacaa    1200
accacctacg gtccccaagg ctgcaccgag cagcaggtac atcgtcaact caatcacagg    1260
tcaaattccc tcacgtcaat gggtgcatcc tacgcagtcg gggctagcgg ggaaacgcac    1320
agcaacgcac aatggctatg ccaaattcgc acaagcaatc ctccatgaac cccacaacgc    1380
tcaccgatca attgggtcta ttccttgatg tcgtggaaac cggcagtttt tccgctgcgt    1440
cccgacgcca tccgctgaca ccctccgccg tcgccaggcg tatcgatagt ctggaacagg    1500
cgctcgacag ccaattgttc gtgcgcacca ctcatgctgt gcgtcctacg ccagcgggat    1560
tggcgtttgc cgagcgagcc cgacgcattg tcggcgagtt gcgcctggcg cgggccgagg    1620
tcgcctccct gagcagcgcg cctgaaggac tgattcgggt cgacgccccc gcagccttcg    1680
gccgcaggca cctggcgccg gtgatctatg actacgactt cgccgcctcc ggcgtgcccg    1740
ggctgcgggg ccggttgcgc tacctgcgcg gcgacaacat cgagttgaaa gccttcaacg    1800
ccgaagaccg caaggagcgc gagttccaga tggagctggg ctacgtggtg caaagcggtc    1860
cgctgaaaaa cgtcggcctg gtggcgcgca aggcaatcta ccgcaatgac ttccccactg    1920
gcgccgcctt ccgcgatgaa aaccagacgc ggtttctggt gacctatacc ttgccgatct    1980
ggtgagtgcg cgtgttgcgg tggggctgat ggccccatcg cgagcgggct cgctcctaca    2040
gtgggtttgg tgttaatcac agaggctgtg gagcttgcag cccctgtagg cgctggcttg    2100
ccagcgaggc gtaggcactg ctggcgcaag gctcaaggcc ccacaggccc gctcccaccc    2160
ttcagatttt ctattcctga taaatcttct tcagcagccg cagcagctcg tcgcgttcct    2220
ggtcgtccag tgccgaggtg gcgtcgaggt cgctttgggc ggcgatctgg ttcagttcct    2280
tgagcagggt ctcgccggtc ttgctgagga atatcccgta cgagcgcttg tccggcttgc    2340
agcgcacacg caccgccagc gcccggcttt ccagcttatt cagcagcggt accacctggg    2400
gcggctcgat gctcagagcc cgggccaggt cggcctgcat caggccgggg ttctgattga    2460
tgatcgccag cgccgagaat tgcgcggggc gcagatcgtg ggccgagagg cggctgatca    2520
ggttctggaa cagtttcagt tgcgcacggc gcatggcgta ccgatcaga tcattcagcg    2580
ccgaatccat gggcgcctgg gtctcggcgg gagtcgacgc agcctcgacc gactcggcga    2640
gggggggaggg cttggccatt gcggggaagt cctgaagatg gaggttaaca agactatcta    2700
gtttgccgac cttggccggt gattgctacg gccaatatcg ctcggcgcca agaccgacca    2760
gtccatcacc tgcgagaaaa ttggttaaat caattaatag ttaattgaca taactaattc    2820
gctgctttaa tttcgagtca tcttcaaaac ccagaacaag agagcatcgc catgagcaca    2880
tacgaaggtc gctggaaaac ggtcaaggtc gaaatcgaag acggcatcgc gtttgtcatc    2940
ctcaatcgcc cggaaaaacg caacgcgatg agcccgaccc tgaaccgcga gatgatcgat    3000
gttctggaaa ccctcgagca ggaccctgcc gccggtgtgc tggtgctgac cggtgcgggc    3060
gaagcctgga ccgcaggcat ggacctcaag gaatacttcc gcgaagtgga cgccggcccg    3120
gaaatcctcc aggaaaaaat ccgccgcgaa gcctcgcaat ggcaatggaa actgctgcgc    3180
atgtacgcca agccgaccat cgccatggtc aatggctggt gcttcggcgg cggtttcagc    3240
ccgctggtgg cctgcgacct ggcgatctgc gccgacgaag caaccttcgg tctctcggaa    3300
atcaactggg gtatcccgcc gggcaacctg gtgagcaagg ccatggccga caccgtgggc    3360
caccgccagt cgctctacta catcatgacc ggcaagacct tcggtgggca gaaagccgcc    3420
gagatgggcc tggtcaacga aagcgtgccc ctggcgcaac tgcgcgaagt caccatcgag    3480
ctggcgcgta acctgctcga aaaaaacccg gtggtgctgc gtgccgccaa acacggtttc    3540
```

-continued

```
aaacgctgcc gcgaactgac ctgggagcag aacgaggatt acctgtacgc caagctcgat    3600
cagtcgcgtt tgctggacac cgaaggcggt cgcgagcagg gcatgaagca attcctcgac    3660
gacaagagca tcaagcctgg cctgcaagcg tataaacgct gaaggacgac gctgcgggcg    3720
cattgcgcga aggcgagtgc gccctgaagc tgcgtttaca tcactgctaa gcattccgat    3780
aaagacgata aagaggaatc accatgctgg acgtgcccct gctgattggc ggccagtcgt    3840
gccccgcgcg cgacggtcga accttcgagc gccgcaaccc ggtgactggc gagttggtgt    3900
cgcgggttgc cgccgccacc ctggaagatg ccgacgccgc cgtggccgct gcccagcaag    3960
cgtttcccgc gtgggccgcg ctggcgccca atgaacggcg cagccgtttg ctcaaggccg    4020
ccgaacaatt gcaggcgcgc agcggcgagt tcatcgaggc ggcgggcgag accggcgcca    4080
tggccaactg gtacgggttc aacgtacggc tggcggccaa catgctgcgt gaagcggcat    4140
cgatgaccac ccaggtcaat ggtgaagtga ttccctcgga cgttccggc agtttcgcca    4200
tggccctgcg ccagccctgt ggcgtggtgc tgggcatcgc ccctggaac gccccggtga    4260
ttctcgccac ccgggcgatt gccatgccgc tggcctgtgg caacaccgtg gtgctgaagg    4320
cttccgagct gagtccggcg gtgcatcgct tgatcggcca ggtgctgcag gacgccggcc    4380
tgggcgatgg cgtggtcaac gtcatcagta atgcgccggc ggatgcggca cagattgtcg    4440
agcgcctgat tgccaacccg gccgtacgcc gggtcaattt caccggttcg acccacgtcg    4500
ggcgcattgt cggcgagctc tcggcgcgcc acctcaaacc ggcgttgctc gagctgggcg    4560
gcaaggcacc gttgctggtg ctcgacgatg ccgacctgga ggctgccgtg caggcggcgg    4620
cgtttggcgc ctacttcaac cagggacaga tctgtatgtc caccgagcgc ctgattgtcg    4680
atgccaaggt ggccgacgcc tttgtcgccc agttggcggc caaggtcgag accctgcgcg    4740
ccggtgatcc tgccgacccg gagtcggtgc tcggttcgct ggtggacgcc agcgctggca    4800
cgcggatcaa agcgttgatc gatgatgccg tggccaaggg cgcgcgcctg gtaatcggcg    4860
ggcaactgga gggcagcatc ttgcagccga ccctgctcga cggtgtcgac gcgagcatgc    4920
gtttgtaccg cgaagagtcc ttcggcccgg tggcggtggt gctgcgcggc gagggcgaag    4980
aagcgctgtt gcaactggcc aacgactccg agttcggttt gtcggcggcg attttcagtc    5040
gtgacaccgg ccgtgccctg gccctggccc agcggtcga atcggcatc tgccacatca    5100
acggcccgac cgtgcacgac gaagcgcaaa tgccttttgg cggggtcaag tccagcggct    5160
acggcagttt tggcggcaag gcatcgattg agcatttcac tcagttgcgc tgggtcaccc    5220
tccagaatgg tccacggcac tatccgatct ga                                  5252
```

<210> SEQ ID NO 8
<211> LENGTH: 1837
<212> TYPE: DNA
<213> ORGANISM: Pseudomonas fluorescens

<400> SEQUENCE: 8

```
gaattcggga tctgggctgc caaccagttg gaagaaaaga ttctcgaagt cggtgtcgac     60
aacgtcggcg ccttcattgc cgagccgatc cagggcgccg gcggcgtgat cgtgccgcca    120
gaaagctact ggccgcgcat caaggaaatc ctcgccaagt acgacatcct gttcgtcgcc    180
gatgaagtga tttgcggttt cggccgtacc ggcgagtggt tcggcagcga tttctacgac    240
ctcaagcccg acatgatgac catcgccaag ggcctgactt ccggctacat cccgatgggt    300
ggtctgatcg tgcgcgattc ggtggtcgaa gtgctgaacg aaggcggcga tttcaaccac    360
```

-continued

```
ggattcacct actccggtca cccggtagcg gcggctgttg ccctggaaaa catccgcatc      420
atgcgcgaag agaagattat cgagcgcgtc caggaagaaa cggcaccgta tttgcaaaag      480
cgtctgcgtg aactcaacga tcatccattg gtgggtgaag ttcgcggggt agggttgctg      540
ggcgctatcg aactggttca ggacaaagcc acgcgcaaac gttacgaagg caagggcgtg      600
ggcatgatct gccggcagtt ctgcttcgac aacgggctga tcatgcgcgc ggttggcgac      660
accatgatca tcgcgccgcc actggtgatt accaaggcgg aaatcgatga gctggtgagc      720
aaggcacgca gtgcctgga cctgaccctg agtgtgttgc agggctaagt gctaggctct       780
gagcgggagt tgtatgaact ttcgctcaga gcggtcagaa agcttggcct ttccttgaaa      840
gaccgccatg gatgttgcca gactagccac cgttccaaat gcccgggttc ggcgcggaac      900
aggtggttca aaaaagcaaa aatttggagc attacgcatg aaggcactcg gtaaaaagct      960
cgccggcaag acactccttg ccatgtccct gatgggcatc atggcgggcg cggttcaggc     1020
agatgacaaa gtcttgcacg tgtacaactg gtccgattac atcgcgccgg acaccatcaa     1080
gaagtttgaa gacgagtcgg gcatcaaggt ggtctacgac gtcttcgaca gtaacgaaac     1140
cctcgaagcc aagttgctgg ccggcaagtc cggttacgac atcgtggtgc cttcgaacaa     1200
cttcctggcc aagcagatca aggccggcgt ctaccagaag ctggacaagt ccaagctgcc     1260
gaactggaag aacctgaaca ccgatctgct caaggccgtt tcggtcagcg accctggtaa     1320
cgagcacgcc ttcccgtaca tgtggggctc gatcggcatc ggcttcaacg ccgagaaggt     1380
caaggccgcg ctgggtccgg atgcaccgac caattcctgg gacctgatct caaaccgga     1440 aaacgccgcc aagctgaaat cctgtggcat cagcgtgctg gattcgccaa ccgagatgat     1500
tccggtggcc ctgcactacc tgggctaccc gaccgacagc caggacaaga aacaactggc     1560
cgaggccgag gcactgttcc tcaaagttcg tccttcgatc ggttacttcc actcctccaa     1620
gtacatttcc gacctggcca acggcaacat ctgcgtggcg atcggctact cgggtgacat     1680
ctatcaggcc aagactcgcg ccgccgaagc cggtgacaag gtcaaggtca gctacaacat     1740
tcccaaagaa ggtgcaggca gcttctacga catggtcgcc atccctaaag atgccgaaaa     1800
cgtcgaaggc gcctacaagt tcatgacctt cctgcag                              1837
```

<210> SEQ ID NO 9
<211> LENGTH: 852
<212> TYPE: DNA
<213> ORGANISM: Pseudomonas fluorescens

<400> SEQUENCE: 9

```
ctgcagacct tctgccaggc gcaccggctc acgcagggtt ttgacttcct ggatcatcag       60
gcgctggttg cgtttgaccg actggccaat catcaggcga aacgcattgg agcccaggtc      120
gatagcggcg aatagcgatg cgtcttcttt cacgtgagga actcctggca acttcgtccg      180
ccgagggcaa aaaccggtt ttgccgatcc tgcacggggt agatgacatc aggatgacat       240
tggaaatttt tctgacagac gtttcgtcac cagaacgtca cagtcgcggg gctagcatcg      300
gggcttccaa tcgggtcggg agccttgaac atgctgttaa ccaacgacac cctgatgcat      360
cgcatccacc gcgagttgct cgaccacagt gacgaagagc tggaactgga gttgctggaa      420
gacgatcacg acctggcttc gctgttcgcg atcaaccgg gcgataccc ggccaaggcc        480 gagcgccgtc gttacttcag cgagttgttc cgtttgcagg gcgagttggt caagttgcaa      540
agctgggtgg tgaagaccgg gcacaaggtg gtgattctgt tcgaaggccg cgatgccgct      600
ggcaaagggg gcgtgatcaa gcgcatcacc cagcgtctta atccacgggt ctgccgggtc      660
```

```
gcggcgcttc cgcgccgag tgaccgcgag cgcacccagt ggtatttcca gcgttatgtc    720
tcgcacctgc ccgccgccgg cgagatcgtc ctgttcgacc gcagctggta caaccgcgcc    780
ggtgtcgagc aggtgatggg cttttgcaac gaggaacagt acgaagaatt tttccgcagc    840
gtgccggaat tc                                                        852
```

<210> SEQ ID NO 10
<211> LENGTH: 958
<212> TYPE: DNA
<213> ORGANISM: Pseudomonas fluorescens

<400> SEQUENCE: 10

```
ctgcagggcc tggggcatgc cgagtcggcg tcgcagaacg cctctgccta tgcgctggaa     60
cgcaagcaaa tgcgtgcgcc cgctcgcccg gtcggagtcg aagccgaagt ggccgacccc    120
attcattttc atccggccat cgccgggtg ttgctgaaac tgaggcccta tgccgagggc    180
atgcgtgcgg tcggttactg ggcggcgcat tgttggatc agtccgagca ggccgaggat    240
ctgcccactc gtcagcgcgc cttgcaactg gcggagctgc tgacgccggt gatcaaggcg    300
ttcttcaccg agcagggttt tcgcctggcc agcaacgcct tgcaggtgtt cggtggctac    360
ggctacgtca gcgagttcgc catcgaacag accctgcgcg acagccggat cgcgatgatt    420
tacgagggca gcaacgaaat ccaggccaat gacctgctgc tgcgcaaagt gctgggggat    480
gaaggtcgcc cctttggcca actgttggcg gtcatgcgcg aagaggccga actggcctgt    540
aacgacaccc gctttggcgc tgagctggtg cagctgtgcg acaaactcga gacagtgcaa    600
cttgagatag gggacctcgc cgtcacggag gcgaatacc cgtatcgagc cgctggcgat    660
ttcctgcgcc tgtgtggcgt ggcgctgttg gggttttcct gggcgagagc ggcacgggtg    720
tctcgcctgt tacctgacag cgatccactg cgtcccaaca aactggaaac cgcgcgtttc    780
ttctttgcct acctgctgcc agaagccgat caacgcctcg cagccattcg ggcggcgaga    840
gcgccgttgc cgttttgat ctgaaaaaac gcccgccagg cccaatgtgg ctcgctccca    900
caaacagcgc gaaccacatc gagccaccgc cgccacgcca gttgtacagg ccgaattc      958
```

<210> SEQ ID NO 11
<211> LENGTH: 959
<212> TYPE: DNA
<213> ORGANISM: Pseudomonas fluorescens

<400> SEQUENCE: 11

```
ctgcaggctt gccatatcag tgcgacagc ttcgtccgcg ctccaggcgc aagggccaac     60
gacctgccga cggtgccgaa taggctgtcg gcgtccgtta ttctggacgc accgcaaaaa    120
ctgttattta cccggtcttc ttccactgta gaaccttttc actatagcgg ccctgcgtgt    180
tctgcgggag ctgctcatga ttctgcacgc gattccactt ccagcccgtt gccgcgccgt    240
gctgttgcgg tttctgcacg cacggctttt gcatcaggct tgcacagcca gccacaaggg    300
caggtaagct ctagctcgca cgtcctgggc gtctcccagg tctgccaacg cgacgcggac    360
gcgtcaaaca acgcccggcc cctaatgaag ccgggacact cagcccagag gcatttatga    420
gtaacaacct cgaccagctc accgattggt tgaaagacca caagatcaca gaagtcgaat    480
gcatgattgg cgacttgacc gggatcaccc gcggcaagat ctcgccaacc aacaagttca    540
ttgccgaaaa aggcatgcgc ctgcccgaga gtgtgctgtt gcagacagtg acgggcgact    600
atgtcgaaga cgacatctat tacgaactgc tcgacccggc cgacatcgac atgatctgcc    660
```

-continued

```
gccccgacca gaacgcggtg ttcctcgtgc catgggccat cgagccgacc gcgcaggtga    720
ttcacgacac ctacgacaag cagggcaacc cgatcgagct gtcgccacgc aacgtcctca    780
agaaagtcct caaactctat tccgacaagg gctggcagcc gatcgtggcg ccggaaatgg    840
agttctacct gaccaagcgc agtgacgacc cggattaccc attgcaaccg ccggttggcc    900
gttccggacg tccggaaatc ggtcgccaat cgttctctat cgaagcggcc aacgaattc     959
```

<210> SEQ ID NO 12
<211> LENGTH: 4259
<212> TYPE: DNA
<213> ORGANISM: Pseudomonas fluorescens

<400> SEQUENCE: 12

```
ctgcaggctt gccatatcag tggcgacagc ttcgtccgcg ctccaggcgc aagggccaac     60
gacctgccga cggtgccgaa taggctgtcg gcgtccgtta ttctggacgc accgcaaaaa    120
ctgttattta cccggtcttc ttccactgta gaaccttttc actatagcgg ccctgcgtgt    180
tctgcgggag ctgctcatga ttctgcacgc gattccactt ccagcccgtt gccgcgccgt    240
gctgttgcgg tttctgcacg cacggctttt gcatcaggct gcacagcca gccacaaggg    300 caggtaagct ctagctcgca cgtcctgggc gtctcccagg tctgccaacg cgacgcggac    360
gcgtcaaaca acgcccggcc cctaatgaag ccgggacact cagcccagag gcatttatga    420
gtaacaacct cgaccagctc accgattggt tgaaagacca caagatcaca gaagtcgaat    480
gcatgattgg cgacttgacc gggatcaccc gcggcaagat ctcgccaacc aacaagttca    540
ttgccgaaaa aggcatgcgc ctgcccgaga gtgtgctgtt gcagacagtg acgggcgact    600
atgtcgaaga cgacatctat tacgaactgc tcgacccggc cgacatcgac atgatctgcc    660
gccccgacca gaacgcggtg ttcctcgtgc catgggccat cgagccgacc gcgcaggtga    720
ttcacgacac ctacgacaag cagggcaacc cgatcgagct gtcgccacgc aacgtcctca    780
agaaagtcct caaactctat tccgacaagg gctggcagcc gatcgtggcg ccggaaatgg    840
agttctacct gaccaagcgc agtgacgacc cggattaccc attgcaaccg ccggttggcc    900
gttccggacg tccggaaatc ggtcgccaat cgttctctat cgaagcggcc aacgaattcg    960
acccgctgtt cgaagacgtc tacgactggt gcgaactgca ggagctggat ctcgatacgc   1020
tgatccacga agacggcacg gcgcagatgg aaatcaactt ccgtcacggc gacgcgctgt   1080
ccctggccga ccagatcctg gtgttcaagc gcaccatgcg cgaggccgcg ctcaagcaca   1140
acgtggccgc cacgttcatg gccaagccga tgaccggcga gcctggcagc gccatgcacc   1200
tgcaccagag catcatcgat atcgagaccg caagaacgct cttctccaat gaagacggga   1260
gcatgagcca gttgttcctc aaccacatcg gcggcctgca gaaattcatc cctgaactgc   1320
tgccgctgtt cgcgcccaac gtcaactcgt tccgccgctt cctgccggac acttcggcgc   1380
cggtgaacgt cgagtggggc gaagaaaacc gtaccgtggg cctgcgggtg ccggatgccg   1440
gccctcaaaa ccgtcgggtg gaaaccgccc tgccgggtgc cgacgccaac ccgtacctgg   1500
cgattgccgc gagcctgctg tgcggctaca tcggcatggt cgaaggtatc aacccaagcg   1560
cgcctgtggt gggtcgtggt tacgagcggc gcaacctgcg tctgccgctg accatcgaag   1620 acgtctctgga acgcatggaa aacagcaaga ccatcgagaa atacctgggt cacaacttca   1680
tcactggcta cgtcgcggtc aagcgggccg agcatgaaaa cttcaagcgc gtgatcagct   1740
catgggaacg ggaattcctg ttgttcgccg tctgacacgc cgggtgcggc cctcaaaagc   1800
cgcactccaa cctcactagg agagctttat gagcaacaac ccgcaaaccc gtgaatggca   1860
```

```
gaacctgagc gccgaacacc acctggcccc cttcagtgac ttcaagcaat tgaaggaaaa    1920
aggcccgcgc gtcatcacca gcgccaaggg cgtttacctg tgggacagcg aaggcaatca    1980
gatcctcgac ggcatggccg gcctgtggtg cgtggccatc ggttacggcc gcgacgagtt    2040
ggccgaggct gccagcaagc agatgcgcga gttgccgtac tacaacctgt ttttccagac    2100
cgctcacccg cccgtcctcg agctggccaa ggcaatttcc gatatcgcgc cagcaggcat    2160
gaaccacgtg ttcttcaccg gttccggctc cgaaggcaat gacaccatgc tgcgcatggt    2220
tcgccactac tgggcgatca aggtcagcc aaacaagaaa gtcattatca gccgcaagaa    2280
cggctaccac ggttcgaccg tggccggcgc cagcctgggc ggcatgacct acatgcacga    2340
acagggcgac ttgccgatcc cgggcatcgt gcacattccg cagccgtact ggttcggtga    2400
aggcggcgac atgaccccgg aagaattcgg gatctggct gccaaccagt tggaagaaaa    2460
gattctcgaa gtcggtgtcg acaacgtcgg cgccttcatt gccgagccga tccagggcgc    2520
cggcggcgtg atcgtgccgc cagaaagcta ctggccgcgc atcaaggaaa tcctcgccaa    2580
gtacgacatc ctgttcgtcg ccgatgaagt gatttgcggt ttcggccgta ccggcgagtg    2640
gttcggcagc gatttctacg acctcaagcc cgacatgatg accatcgcca agggcctgac    2700
ttccggctac atcccgatgg gtggtctgat cgtgcgcgat tcggtggtcg aagtgctgaa    2760
cgaaggcgc gatttcaacc acggattcac ctactccggt cacccggtag cggcggctgt    2820
tgccctggaa acatccgca tcatgcgcga agagaagatt atcgagcgcg tccaggaaga    2880
aacggcaccg tatttgcaaa agcgtctgcg tgaactcaac gatcatccat ggtgggtga    2940
agttcgcggg gtagggttgc tggcgctat cgaactggtt caggacaaag ccacgcgcaa    3000
acgttacgaa ggcaagggcg tgggcatgat ctgccggcag ttctgcttcg acaacgggct    3060
gatcatgcgc gcggttggcg acaccatgat catcgcgccg ccactggtga ttaccaaggc    3120
ggaaatcgat gagctggtga gcaaggcacg caagtgcctg gacctgaccc tgagtgtgtt    3180
gcagggctaa gtgctaggct ctgagcggga gttgtatgaa cttcgctca gagcggtcag    3240
aaagcttggc ctttccttga agaccgcca tggatgttgc cagactagcc accgttccaa    3300
atgcccgggt tcggcgcgga acaggtggtt caaaaaagca aaaatttgga gcattacgca    3360
tgaaggcact cggtaaaaag ctcgccggca agacactcct tgccatgtcc ctgatgggca    3420
tcatggcggg gcgcggttcag gcagatgaca agtcttgca cgtgtacaac tggtccgatt    3480
acatcgcgcc ggacaccatc aagaagtttg aagacgagtc gggcatcaag gtggtctacg    3540
acgtcttcga cagtaacgaa accctcgaag ccaagttgct ggccggcaag tccggttacg    3600
acatcgtggt gccttcgaac aacttcctgg ccaagcagat caaggccggc gtctaccaga    3660
agctggacaa gtccaagctg ccgaactgga agaacctgaa caccgatctg ctcaaggccg    3720
tttcggtcag cgaccctggt aacgagcacg ccttcccgta catgtgggc tcgatcggca    3780
tcggcttcaa cgccgagaag gtcaaggccg cgctgggtcc ggatgcaccg accaattcct    3840
gggacctgat cttcaaaccg gaaaacgccg ccaagctgaa atcctgtggc atcagcgtgc    3900
tggattcgcc aaccgagatg attccggtgg ccctgcacta cctgggctac ccgaccgaca    3960
gccaggacaa gaaacaactg gccgaggccg aggcactgtt cctcaaagtt cgtccttcga    4020
tcggttactt ccactcctcc aagtacattt ccgacctggc caacggcaac atctgcgtgg    4080
cgatcggcta ctcgggtgac atctatcagg ccaagactcg cgccgccgaa gccggtgaca    4140
aggtcaaggt cagctacaac attcccaaag aaggtgcagg cagcttctac gacatggtcg    4200
```

```
ccatccctaa agatgccgaa aacgtcgaag gcgcctacaa gttcatgacc ttcctgcag    4259

<210> SEQ ID NO 13
<211> LENGTH: 20
<212> TYPE: PRT
<213> ORGANISM: Pseudomonas fluorescens

<400> SEQUENCE: 13

Ser Thr Tyr Glu Gly Arg Trp Lys Thr Val Lys Val Glu Ile Gln Asp
 1               5                  10                  15

Gly Ile Ala Phe
            20

<210> SEQ ID NO 14
<211> LENGTH: 7
<212> TYPE: PRT
<213> ORGANISM: Pseudomonas fluorescens

<400> SEQUENCE: 14

Ser Thr Tyr Glu Gly Arg Trp
 1               5
```